(12) United States Patent
Peacock, III et al.

(10) Patent No.: US 6,695,810 B2
(45) Date of Patent: Feb. 24, 2004

(54) ENDOLUMENAL AORTIC ISOLATION ASSEMBLY AND METHOD

(75) Inventors: James C. Peacock, III, San Francisco, CA (US); Frederick Gotha, Arcadia, CA (US); Jeffrey S. Kadan, Redondo Beach, CA (US); Ronald Coleman, Oakland, CA (US)

(73) Assignee: Advanced Interventional Technologies, Inc., Redondo Beach, CA (US)

( * ) Notice: Subject to any disclaimer, the term of this patent is extended or adjusted under 35 U.S.C. 154(b) by 16 days.

(21) Appl. No.: 09/859,884

(22) Filed: May 16, 2001

(65) Prior Publication Data

US 2002/0049402 A1 Apr. 25, 2002

Related U.S. Application Data

(63) Continuation-in-part of application No. 09/191,260, filed on Nov. 12, 1998, now Pat. No. 6,234,995, which is a continuation-in-part of application No. 08/976,250, filed on Nov. 21, 1997, now Pat. No. 5,928,181.

(51) Int. Cl.[7] .............................................. A61M 29/00
(52) U.S. Cl. .............................. 604/99.04; 604/101.05; 604/102.02
(58) Field of Search ........................... 604/96.01, 99.02, 604/99.04, 101.03, 102.02, 264, 536, 907, 917, 103.5, 101.05, 102.01; 606/191, 194

(56) References Cited

U.S. PATENT DOCUMENTS 6,045,531 A * 4/2000 Davis .................... 604/101.05

* cited by examiner

Primary Examiner—Michael J. Hayes
Assistant Examiner—Catherine Serke
(74) Attorney, Agent, or Firm—Frederick Gotha

(57) ABSTRACT

A medical device system and method allows an arterial bypass graft to be proximally anastomosed to an aorta during a beating heart procedure without substantial loss of blood by use of an endolumenal aorta isolation assembly provided along the distal end portion of an elongate catheter body. The aorta isolation assembly includes proximal and distal portions that are separated by an isolation region and that are adjustable to first and second extended positions, respectively, which are adapted to circumferentially engage the aortic wall and isolate upstream and downstream aspects of an exterior space between the elongate body and the aortic wall. The intermediate region is adapted to be positioned along the proximal anastomosis site such that the distal and proximal portions when adjusted to the first and second extended positions circumferentially engage the aortic wall on upstream and downstream sides of the proximal anastomosis site. Blood flowing within the aorta is thereby isolated from the proximal anastomosis site along the intermediate region and is shunted from an upstream region of the aorta, through the distal port into the flow lumen, proximally along the flow lumen, out from the flow lumen though the proximal port.

58 Claims, 29 Drawing Sheets

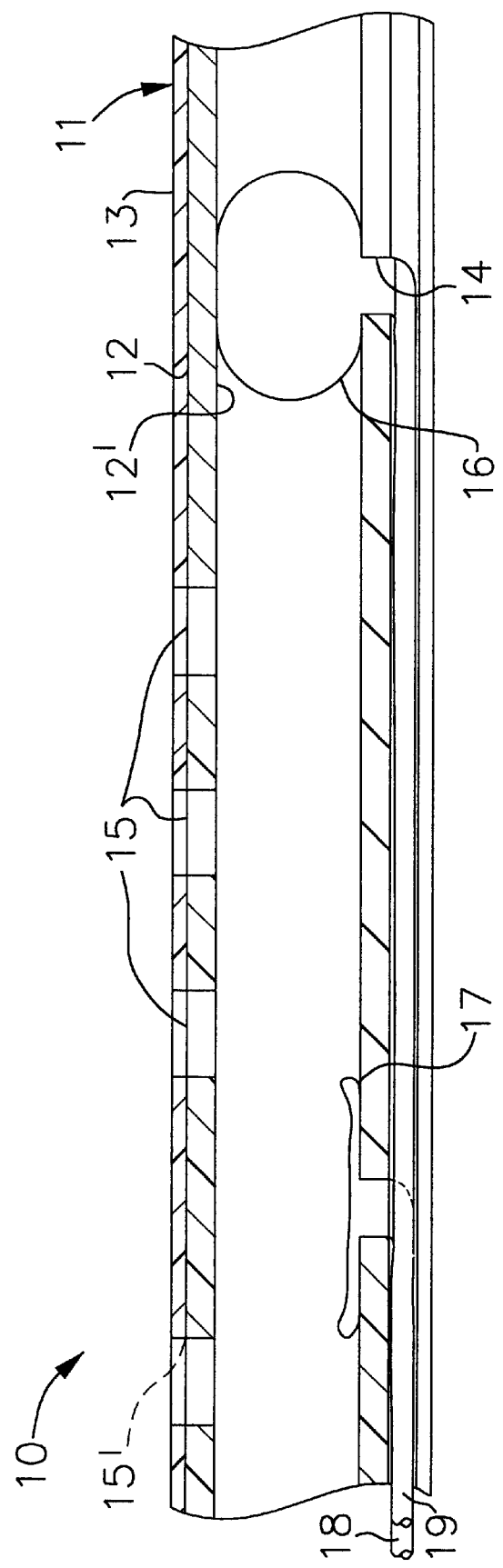

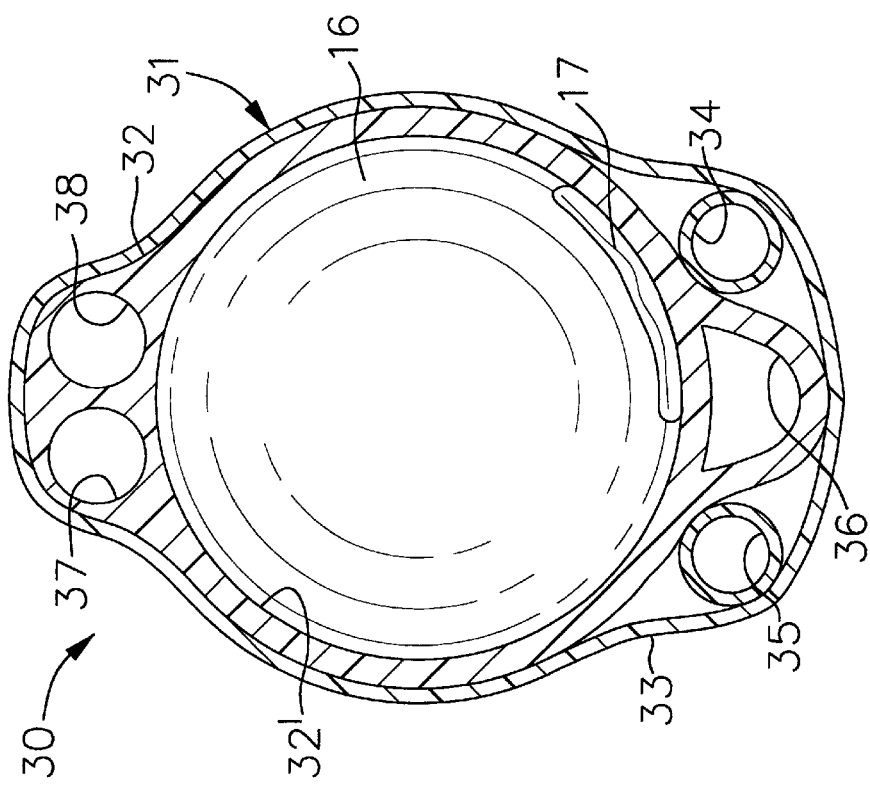
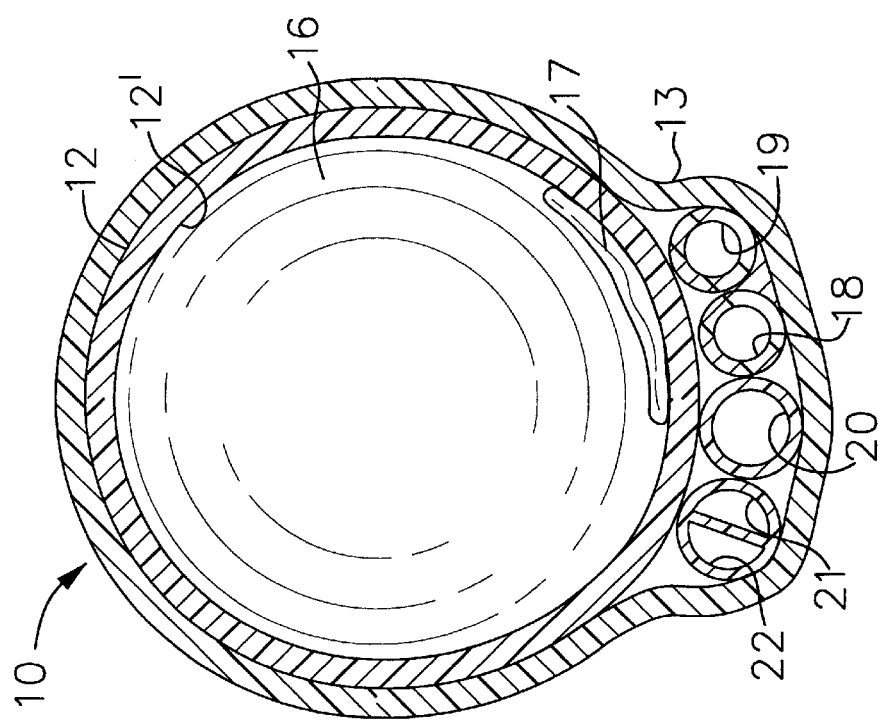

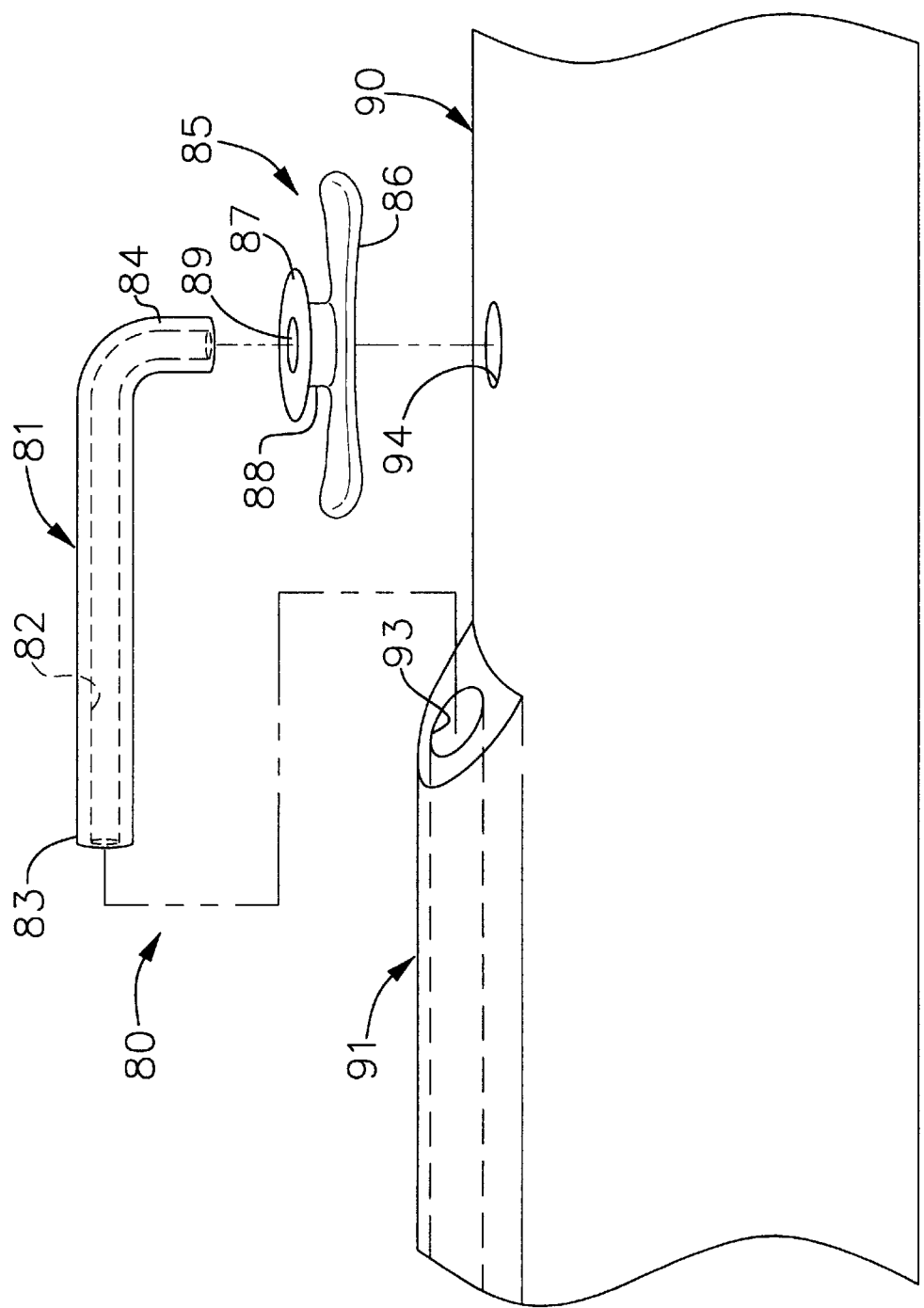

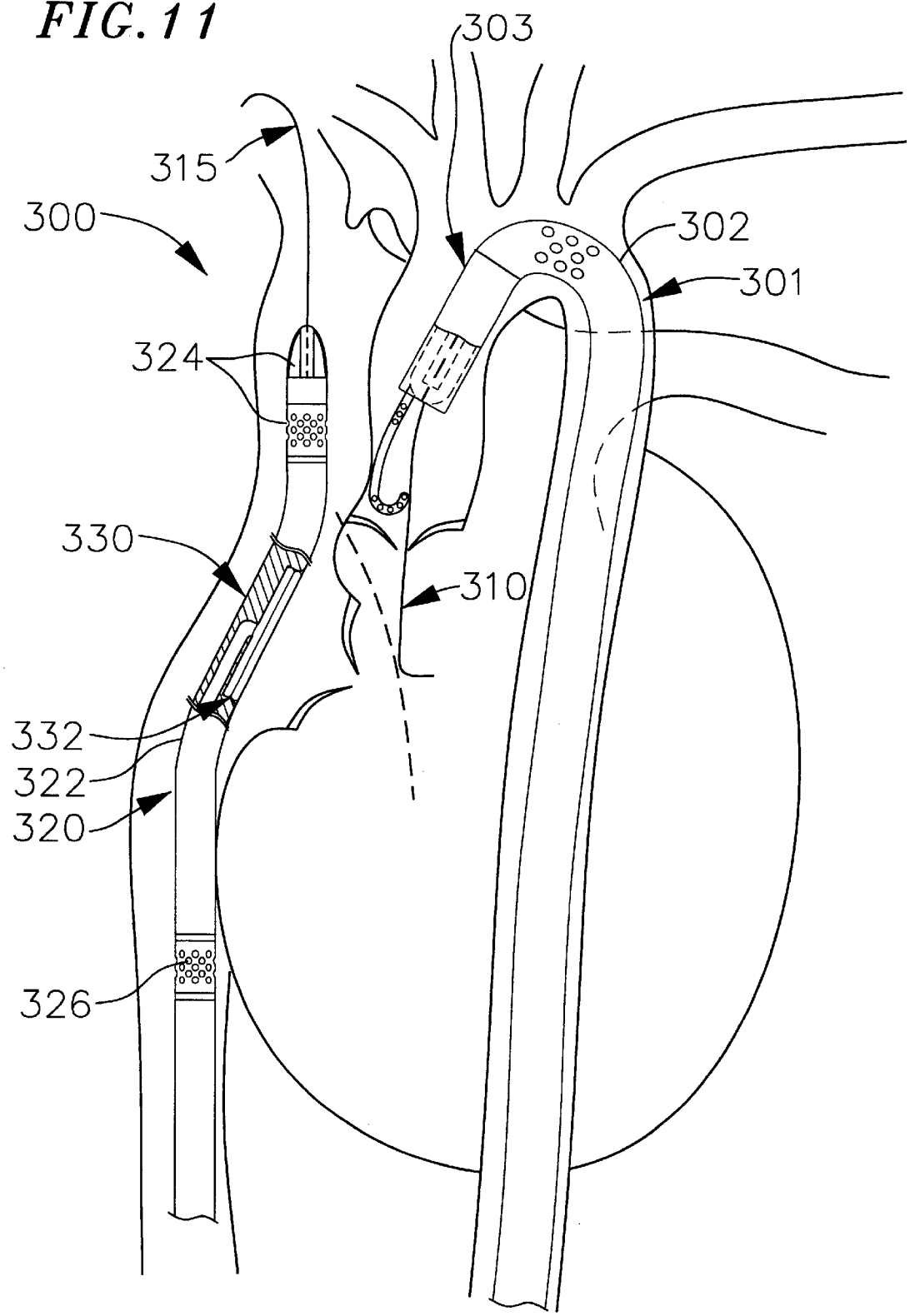

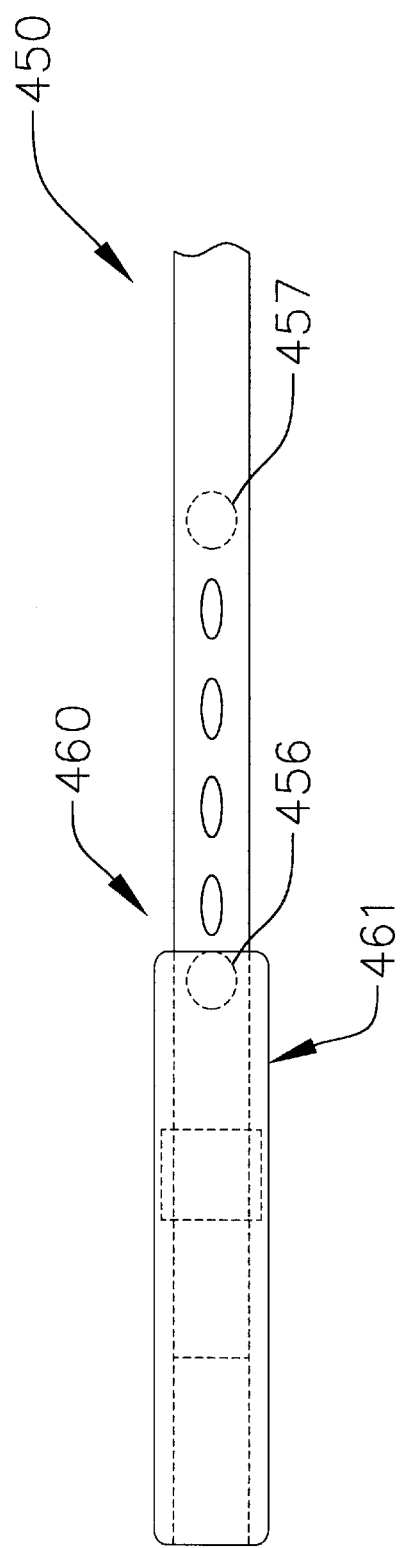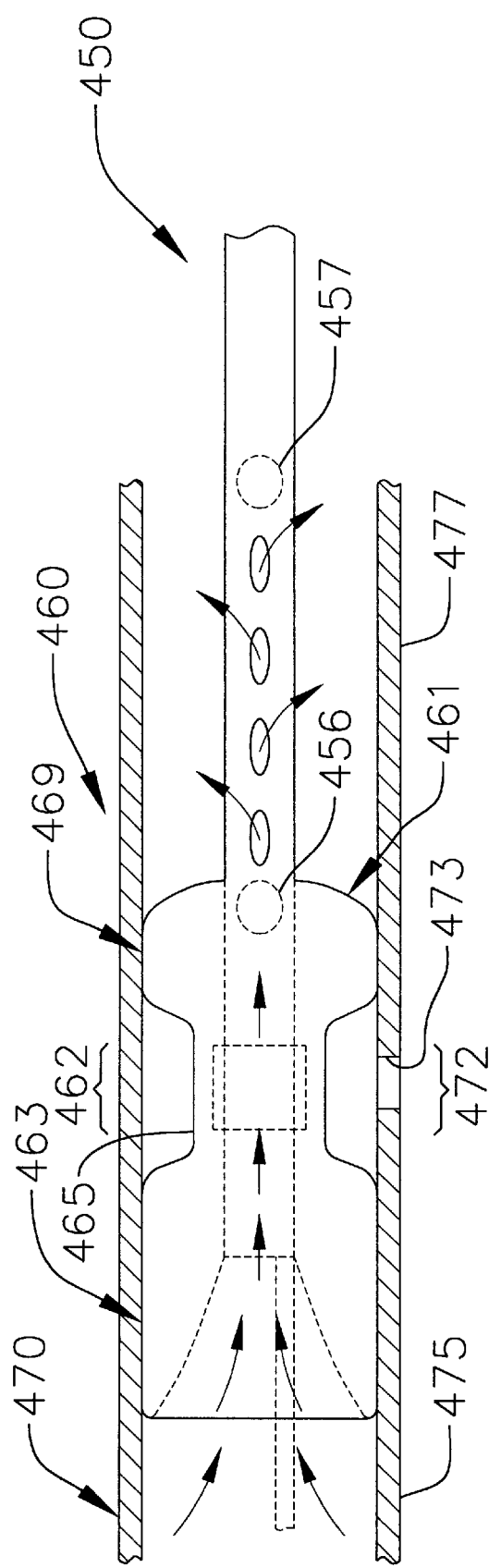

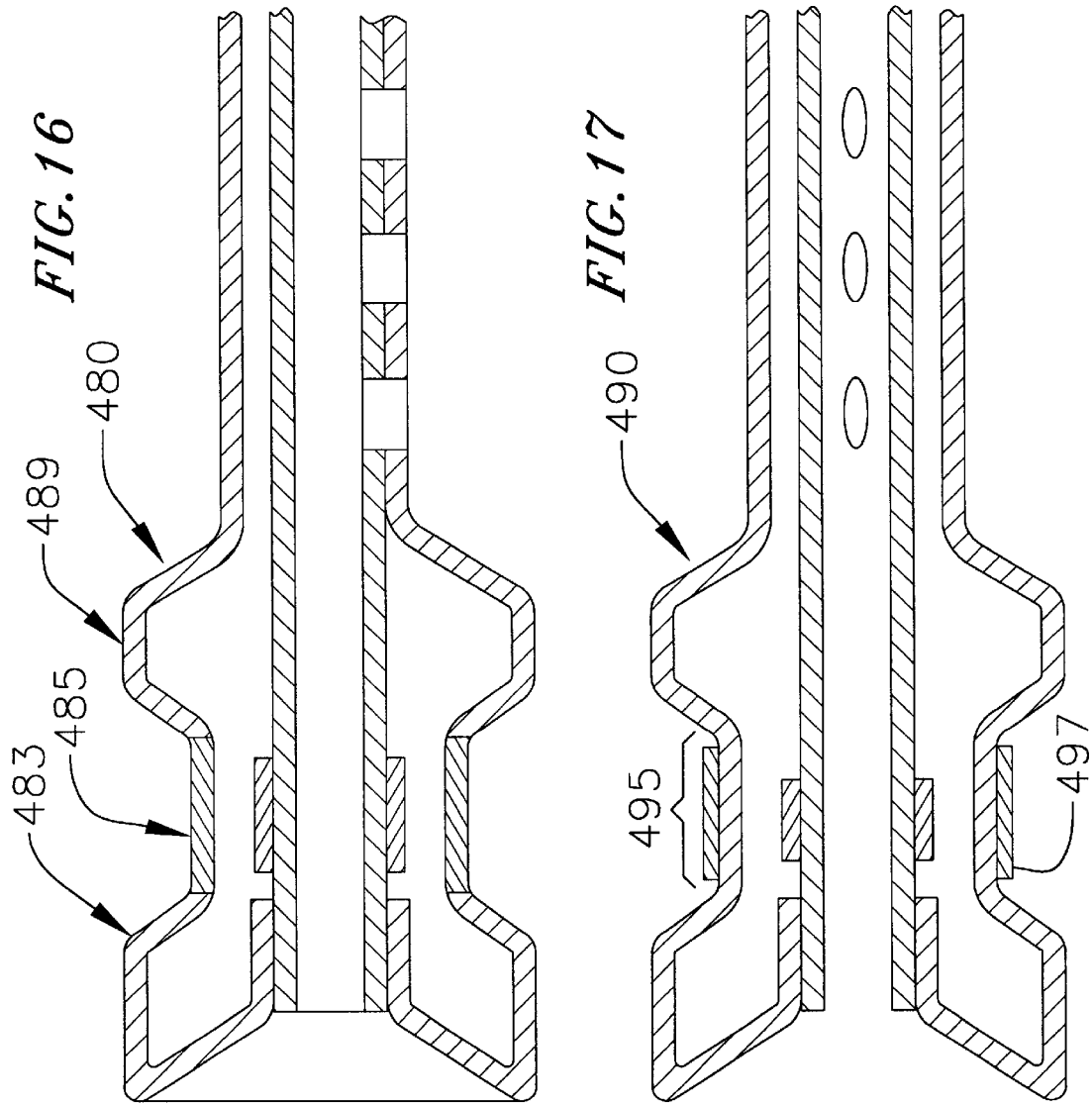

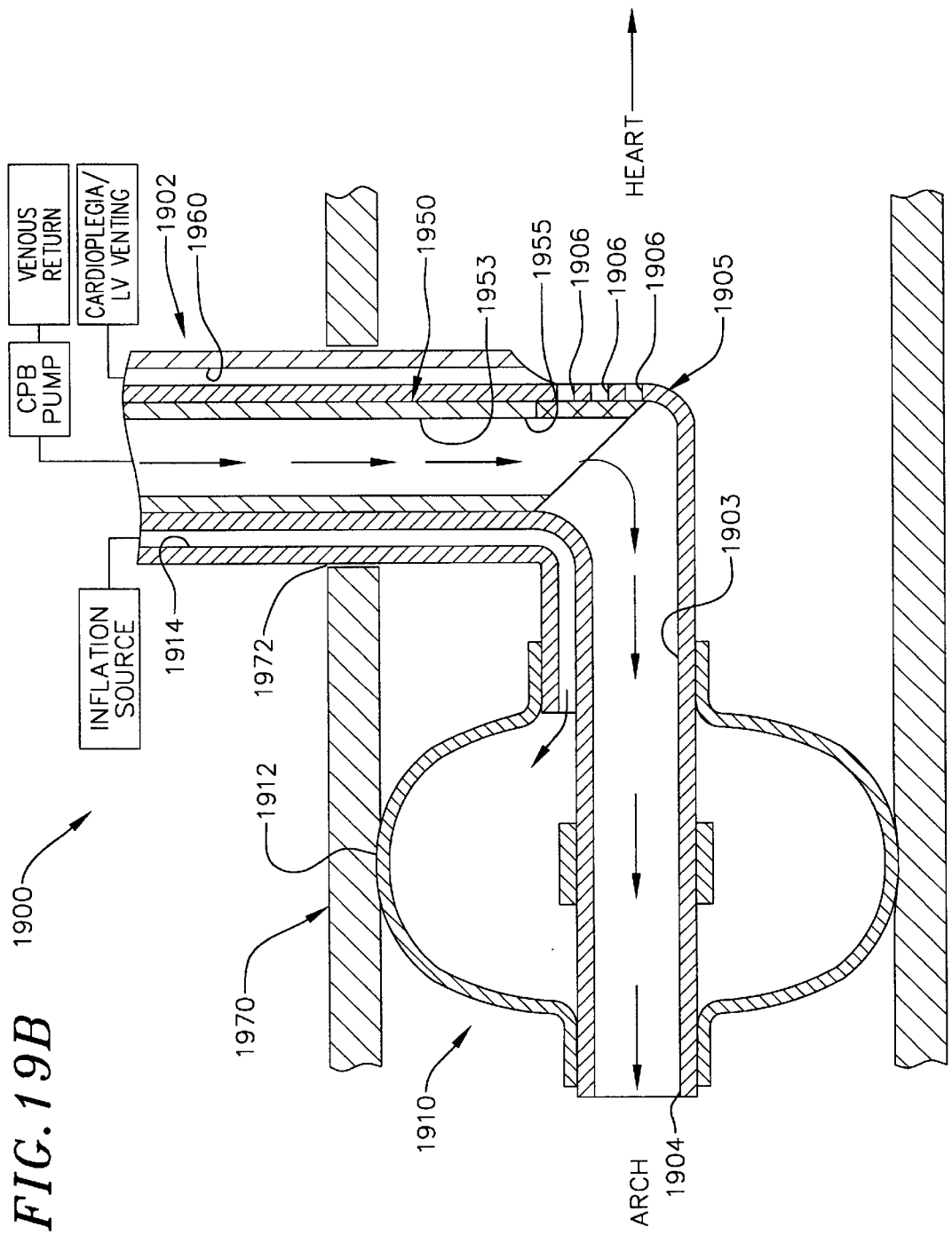

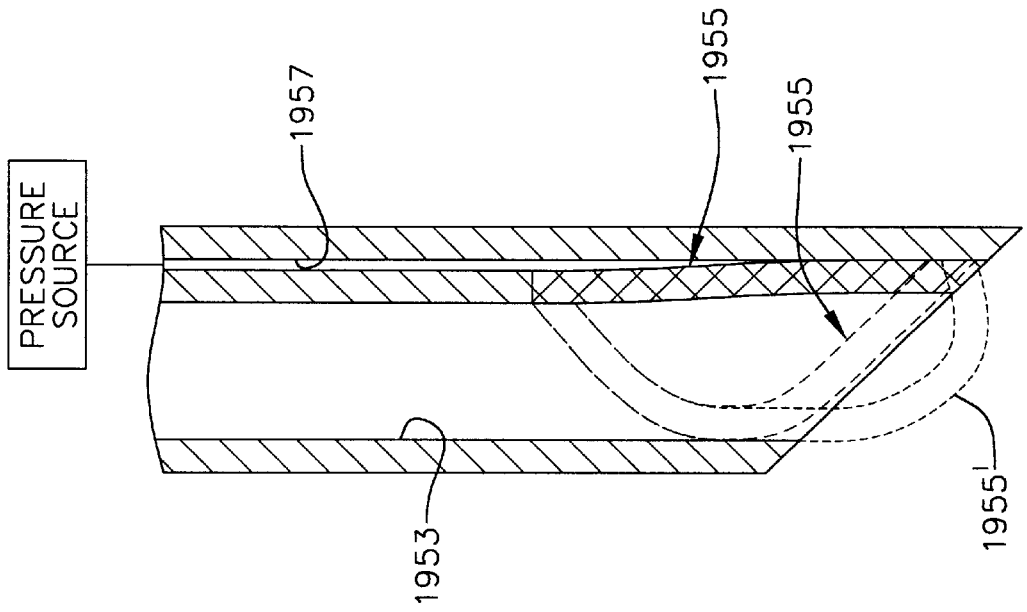
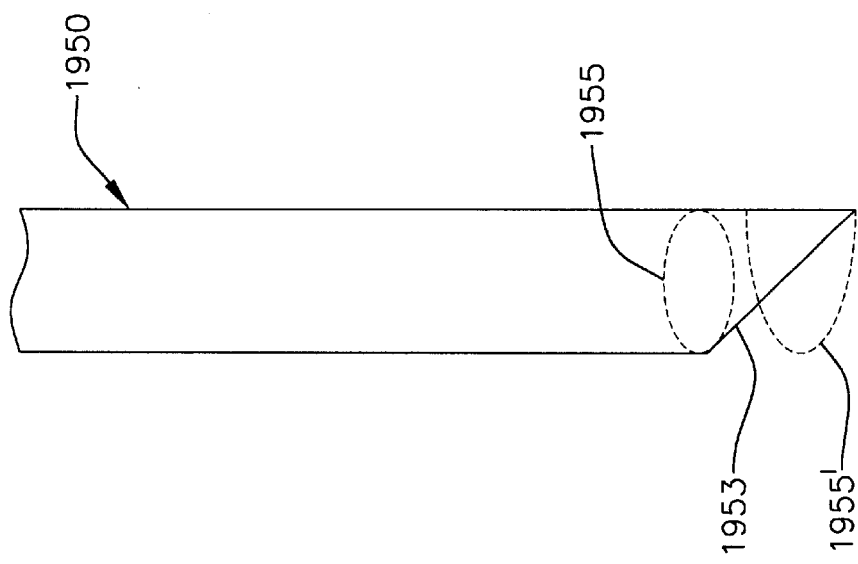

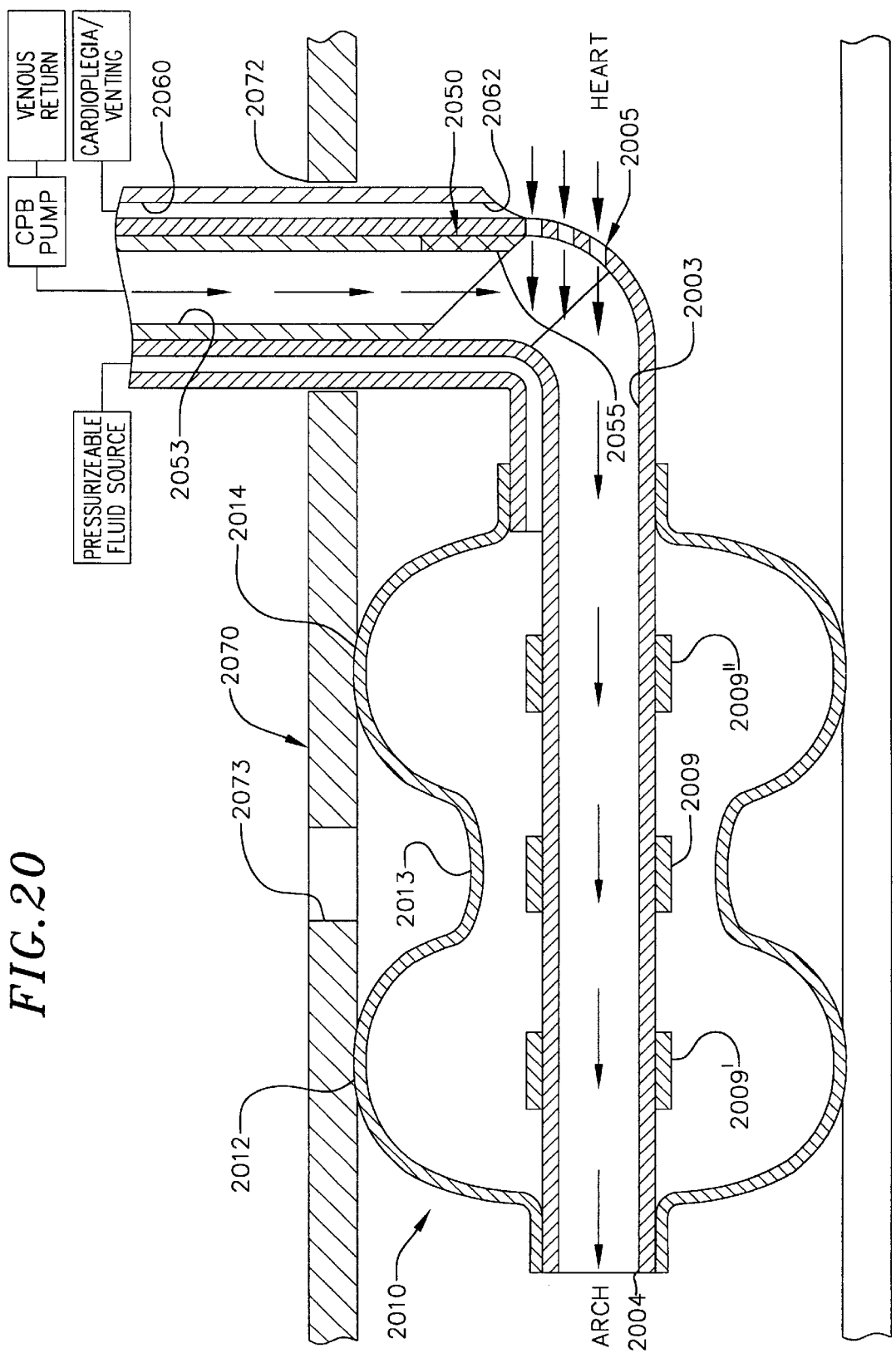

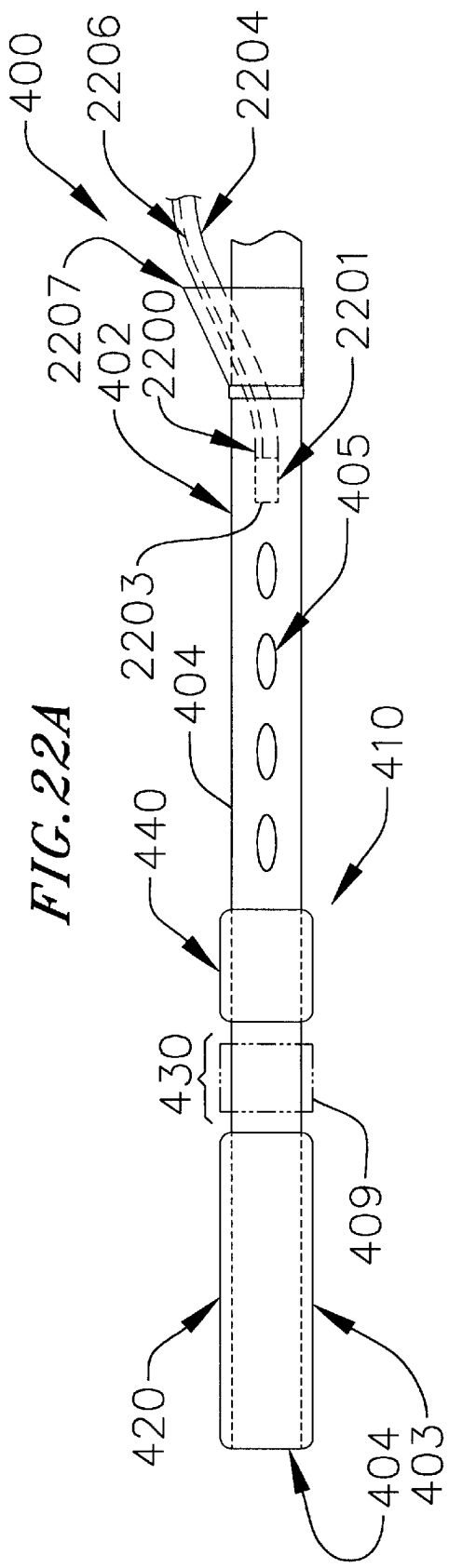
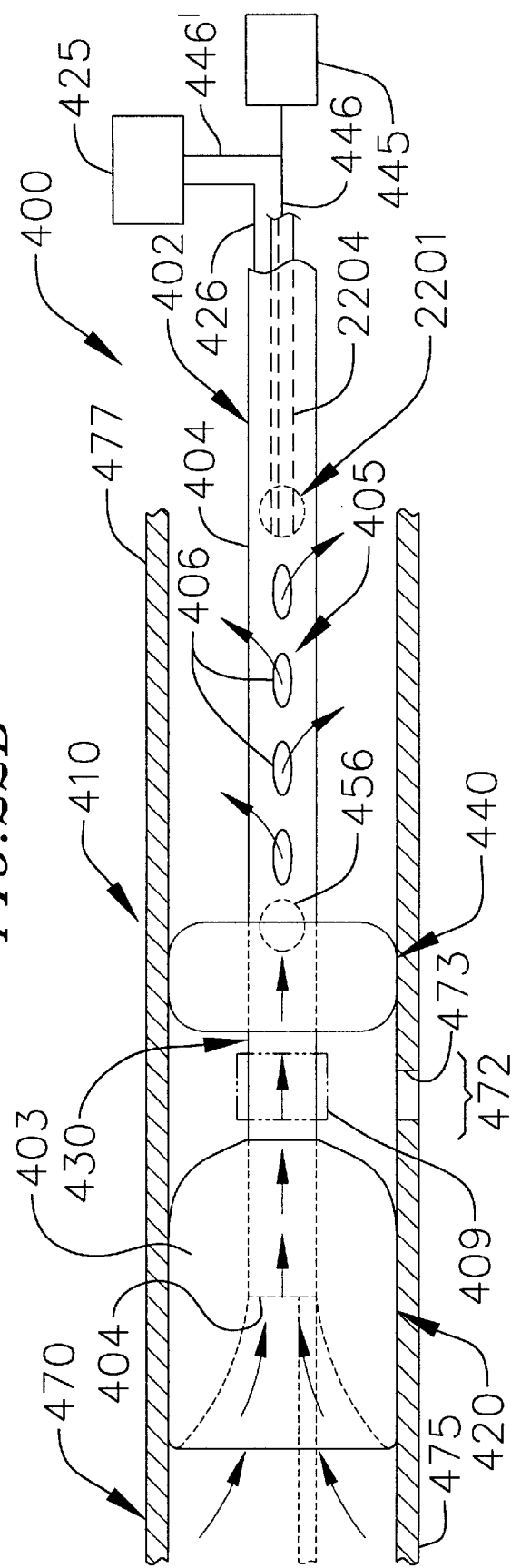
FIG.22A
FIG.22B

ENDOLUMENAL AORTIC ISOLATION ASSEMBLY AND METHOD

This application is a continuation-in-part of application Ser. No. 09/191,260 filed Nov. 12, 1998, now U.S. Pat. No. 6,234,995, which was a continuation-in-part of application Ser. No. 08/976,250, filed Nov. 21, 1997, now U.S. Pat. No. 5,928,181.

TECHNICAL FIELD

The present invention is a surgical device assembly. More particularly, it is a medical device system and method for endolumenally isolating a region of a patient's aorta from the patient's systemic arterial circulation so that surgery may be performed on the isolated portion of the aorta or the patient's heart.

BACKGROUND

Conventional "Cardiac Bypass" Procedures

Various medical procedures have been developed for treating particular abnormalities of the heart and vascular system at least in part by temporarily arresting the heart from beating, isolating the heart from systemic blood circulation, supporting the systemic blood circulation via an external cardiopulmonary bypass pump, and performing surgical operations directly on the stopped heart. This general method is herein referred to interchangeably as a "cardiac bypass" or "cardiopulmonary bypass" procedure. Examples of more particular surgical treatments which use such cardiac bypass procedures include, without limitation: coronary artery bypass graft surgery ("CABG"); valve replacement surgery; cardiac transplantation surgery; and a procedure known as the "maze" procedure wherein conduction blocks are surgically formed in the wall of one or both of the atria in order to prevent atrial fibrillation.

Conventional techniques for performing such "cardiac bypass procedures" generally cutting through the sternum in the chest cavity using well known "sternotomy" techniques, spreading open the rib cage, retracting the lungs from the region of the heart, and directly exposing the heart to the surgeon. One of various known cardioplegia agents may be used to temporarily arrest the heart from beating. Further to the bypass procedure, an external cross clamp is generally used to occlude the aorta in the region of the arch between the aortic root and the carotid arteries. With the cross-clamp in this position, both the left heart chambers and the coronary arteries into the heart are isolated from the systemic arterial circulation while the carotid arteries are fed with the blood flow from the bypass pump. In addition, flow from the superior and inferior vena cava is also temporarily diverted from the heart to the pump, usually by externally tying the vena caval walls onto venous pump cannulae. Such conventional cardiac bypass procedures as just describe which involve performing a sternotomy are hereafter referred to interchangeably as "open chest" or "open heart" procedures.

Minimally Invasive Cardiac Bypass Catheter Systems

Recent advances have been made in the field of "cardiac bypass procedures" which include the use of novel catheter assemblies which are adapted to temporarily arrest and bypass the heart without the need for direct cross-clamping or externally tying the vena cavae. Such assemblies are generally herein referred to by the terms "minimally invasive catheter bypass systems," or derivatives of these terms, and generally include an arterial catheter, which isolates the left heart chambers from systemic arterial circulation beyond the aortic root, and a venous catheter, which isolates the right heart chambers from venous circulation from the vena cavae. Further to the intended meaning, such minimally invasive catheter bypass systems may be used during open chest procedures requiring a sternotomy, as well as during other cardiac bypass procedures which otherwise alleviate the need for such sternotomies, such as for example procedures known as "port access" procedures.

One particular example of a previously known "minimally invasive cardiac bypass system" uses an arterial catheter which occludes the aorta from systemic arterial circulation with an inflatable balloon located on the outside surface of the catheter's distal end portion which is positioned within the aorta. The arterial catheter further includes a cannula with lumens and distal ports which provide for cardioplegia agent delivery and venting of the left ventricle, respectively, while the heart is isolated from systemic circulation with the inflated balloon on the outer surface of the arterial catheter. Further to this known system, a venous catheter is further provided and uses a balloon in each of the superior and inferior vena cava. The venous catheter balloons inflate to occlude these great veins and thereby isolate the right heart chambers from systemic venous blood flow. Moreover, the venous and arterial catheters which combine to form minimally invasive cardiac bypass catheter systems engage to inlet and outlet ports, respectively of a cardiopulmonary bypass pump, which pump may be further considered a part of the overall system. One such known pump which is believed to be particularly useful in cardiac bypass procedures, including minimally invasive bypass procedures, is known as the "BioPump", Model Number "BP80", which is available from Medtronic, Inc.

Further to the description for the minimally invasive cardiac bypass system example just provided above, the terms "proximal" and "distal" are herein used throughout this disclosure as relative terms. In the context of describing a device or catheter used in such a system, the term "proximal," such as in the phrase "proximal end", is herein intended to mean toward or closer to a user such as a physician, whereas the term "distal," such as in the phrase "distal end" is herein intended to mean away from or further away from the user. However, if and where the terms "proximal" and "distal" are herein used in the context of describing anatomical structures of the cardiovascular system or physiological blood flow, the term "proximal" is herein intended to mean toward or closer to the heart, whereas the term "distal" is herein intended to mean away from or further from the heart. Furthermore, the terms "upstream" and "downstream" are also relative terms which may be herein used interchangeably with "proximal" or "distal", respectively, in the anatomical or physiological context just described.

According to the known minimally invasive cardiac bypass catheter systems and methods, the heart is usually put on "partial bypass" prior to "complete bypass". The terms "partial bypass" are herein intended to mean a condition wherein the heart is beating and pumping blood throughout the body's circulation prior to inflating the balloons on the arterial and venous catheters, and wherein some blood is also aspirated from the vena cavae through the venous catheter, sent through the cardiopulmonary bypass pump, and infused into the arterial circulation through the flow ports along the arterial catheter. The terms "complete bypass" or "full bypass" or derivatives thereof are therefore herein intended to mean a condition wherein the heart is substantially isolated from systemic venous and arterial circulation by means provided by the venous and arterial catheters, respectively, such as for example by inflating balloons on the exterior surfaces of such venous and arterial catheters to thereby totally occlude the vena cavae and aorta, also respectively, as described above.

According to these definitions for partial and full bypass just provided, a patient is therefore put on partial bypass by first positioning the venous and arterial catheters at predetermined locations along the vena cavae and aorta, respectively, such that the associated flow ports may provide for the aspiration or infusion of blood, respectively, and such that balloons on the catheter outer surfaces may be thereafter inflated to isolate the right and left heart chambers, also respectively, during full bypass. The procedure for subsequently weaning a patient from partial bypass to full bypass according to the known minimally invasive cardiac bypass system example described above generally proceeds as follows.

Cardioplegia agent is delivered during partial bypass in order to begin reducing the cardiac function ultimately toward the temporarily arrested state. The external balloons are inflated to occlude the vena cavae and isolate the right heart from systemic venous circulation prior to inflating the arterial catheter's balloon to isolate the left heart from systemic arterial circulation. During this "weaning" period, the bypass pump circulates the blood aspirated from the vena cavae while the heart continues to pump a declining volume of residual blood from the coronary sinus, right heart chambers, pulmonary circulation (including lungs), and left heart chambers. As the residual volume of blood pumping through the heart declines, and as the cardiac function continues toward temporary arrest under cardioplegia effects, the balloon on the exterior surface of the arterial catheter is then inflated to occlude the aorta and finally achieve full or complete bypass.

Upon inflating the arterial balloon and totally occluding the aorta during the "weaning" period onto full bypass as just described, additional cardioplegia agent delivery continues distally of the inflated balloon. However, it has been observed that "back pressure" on the cardioplegia delivery cannula during cardioplegia agent delivery, together with the pressure from the beating heart against the totally occluded aorta, may push the arterial balloon downstream along the aorta. As a result, a user may be required to reposition the balloon at the initially desired location along the ascending aorta between the aortic root and the carotid arteries. It is believed that the repositioning of the arterial balloon in response to this pressure response may be performed while the balloon is inflated, or during subsequent iterations of positioning and then inflating in order to adjust for the observed post-inflation movement.

Still further to the known "minimally invasive cardiac bypass systems," weaning a patient off of "complete bypass" and off of the cardiopulmonary bypass pump while reestablishing physiological cardiac output generally requires deflation of the external balloon on the external surfaces of the arterial and venous catheters. However, some patients have been observed to present complications while cardiac function is being reestablished, which complications may require returning the patient back to a full bypass condition. Therefore, patients are generally kept in surgery for a prolonged period of time subsequent to deflating the balloons on the bypass system catheters and after reestablishing the cardiac function in order to observe the heart's recovery. In cases where such patients are required to be put back onto cardiac bypass, the balloons must be repositioned at their desired location and then reinflated to isolate the heart. Particularly regarding the occlusion balloon on the external surface of the arterial catheter, this reinflation while the heart is pumping may present the same repositioning issues as previously described above.

It is further believed that the arterial balloon repositioning which may be required during use of arterial catheters according to the known minimally invasive cardiac bypass systems may present a cumbersome and potentially dangerous detriment to the efficiency and safety of the overall minimally invasive cardiac bypass procedure.

"Beating-Heart" CABG Procedures

Various methods related primarily to CABG procedures have also been disclosed which are performed without placing the heart on cardiopulmonary bypass or otherwise in a pressurized blood field.

For example, even conventional open chest CABG procedures have been disclosed for forming a proximal anastomosis between a bypass graft and an aorta without isolating the pressurized blood field in the aorta from the entire region along flow path in the aorta where the anastomosis is to be formed. In particular, one such method uses a "side-clamp" surgical tool which is adapted with two apposable, curved arms that are adapted to squeeze and clamp-off only a portion of the aortic wall. This "bite" of the aortic wall is thereby isolated from the blood field by way of the side-clamp. Thus an aperture may be formed or "punched" through the aortic wall along the isolated bite and the proximal anastomosis may be completed at that aperture without significant loss of blood from the aorta. However, it is believed that such externally clamping of the aorta may present some degree of undesirable mechanical trauma to the aortic wall tissue as the aorta is in part crushed and deformed by such clamps, and furthermore that such external clamping may give rise to various procedural complications during some CABG procedures.

Recent advances have also been made also principally in minimally invasive CABG procedures which also allow a bypass graft to be anastomosed proximally to an aorta and distally to a coronary artery without the need to place the patient on cardiopulmonary bypass. One such disclosed procedure requires particular minimally invasive device assemblies and methods that are adapted to form the anastomoses while the heart is beating. One detailed device which has been disclosed for use in such procedures includes a "perfusion bridge" for use in perfusing a region of a coronary artery while substantially isolating a distal anastomosis site along that region from the perfused arterial blood. Another detailed device for use in such procedures provides a structure or "foot" for engaging and substantially securing the motion of the beating heart while a distal anastomosis is formed, such according to at least one disclosed mode by use of suction.

At least one other known procedure involves particular devices and methods which are adapted to temporarily arrest or otherwise reduce a heart beat for relatively short periods of time, without cardiopulmonary bypass support, and only while various steps for forming a distal graft anastomosis are performed in a CABG procedure. According to this method, the heart is temporarily "stunned" from beating, such as by stimulating the vagal nerve, while forming an anastomoses and rapidly recovers to resume beating quickly after the anastomosis is completed. According to this prior disclosure, it is believed that the patient tolerates such short interruptions or reductions in the heart beat sufficiently to not require cardiopulmonary bypass support. Such novel procedures as just described which either temporarily reduce or arrest the heart without cardiopulmonary bypass support are herein generally referred to as "semi-beating heart" procedures. Moreover, the terms "beating heart" in relation to the various assemblies and methods described are herein intended to generically mean any procedure operating in a pressurized aortic blood field without the heart on cardiopulmonary bypass. Therefore, such "beating heart" assemblies and methods are intended to encompass both the "semi-beating heart" assemblies and methods just specifically described, in addition to the more specific applications of devices and methods wherein a heart is substantially beating in the normal physiologic rhythm for a given patient. Moreover, such "beating heart" procedures as just described, it is appreciated that related minimally invasive catheter bypass systems and methods may be used to perform such procedures either in an "open chest" mode incorporating a sternotomy to directly expose the heart, as well in "port access" mode that otherwise alleviates the need for such sternotomies.

Further more detailed device assemblies and methods for performing at least in part beating heart or semi-beating heart CABG procedures, such as of the types just described, are variously disclosed in the following U.S. Patent References: U.S. Pat. No. 5,776,154 to Taylor et al.; U.S. Pat. No. 5,769,870 to Salahieh et al.; U.S. Pat. No. 5,727,569 to Benetti et al.; U.S. Pat. No. 5,651,378 to Matheny et al.; U.S. Pat. No. 5,730,757 to Benetti et al.

"Direct Access" Endolumenal Aortic Isolation

Other recently developed assemblies and methods are intended to allow for direct cannulation of the aorta in order to endolumenally clamp and isolate a region of the aorta so that various surgical procedures may be performed such as previously described above. According to such "direct access" procedures, an endolumenal clamp such as an endoaortic balloon catheter is positioned within the aorta through an introduction site through the aortic wall. According to at least one known specific variation, the endolumenal clamp or balloon is positioned at an endolumenal clamp site generally located between the carotid arteries and the aortic valve where it is then actuated to occlude the aorta at that site, thereby isolating the heart from the systemic arterial circulation including the carotid flow.

One more detailed example of an aorta-occluding balloon catheter which is intended for use in "direct access" aortic isolation is disclosed in U.S. Pat. No. 5,428,708 to Nanu.

SUMMARY OF THE INVENTION

BRIEF DESCRIPTION OF THE DRAWINGS

FIG. 2A shows a longitudinal cross-sectional view of one particular endolumenal aortic isolation catheter according to the schematic view shown in FIGS. 1A–B.

FIG. 2B is a distally oriented perspective view taken through a transverse cross-section of an arterial catheter similar to that shown in FIG. 2A.

FIG. 2C is a similar transverse cross-sectional view as that shown in FIG. 2B, although showing another particular lumenal construction for a catheter such as that shown in FIG. 2A.

FIGS. 3A–B show perspective views of another particular endolumenal aortic isolation catheter, wherein FIG. 3A shows a proximally oriented perspective view of the proximal end portion of the catheter and includes a perspective view of a transverse cross-section taken through the proximal end portion of the elongate body, and wherein FIG. 3B shows a distally oriented perspective view of the distal end portion of the catheter and includes a perspective view of a transverse cross-section taken through the distal end portion of the catheter's elongate body in the region of a proximal internal valve.

FIG. 3C shows a more detailed, perspective view of one particular means for constructing an internal valve according to the internal valve variation shown in FIG. 3B.

FIG. 11 shows a medical device system during one mode of use in isolating a heart from the venous and arterial systemic systems in a patient.

FIG. 15A shows a perspective view of the distal end portion of another endolumenal aortic isolation catheter adapted for use in a "beating heart" endolumenal aortic isolation procedure.

FIG. 15B shows a perspective view of the endolumenal aortic isolation catheter shown in FIG. 15A, except showing the catheter during one mode of use when isolating a proximal anastomosis site along an aorta.

FIG. 16 shows a cross-sectioned side view of the distal end portion of an endolumenal aortic isolation catheter which is similar to that shown in FIGS. 15A–B, and shows the catheter to include one specific type of isolation assembly.

FIG. 17 shows a side cross-section view of the distal end portion of another arterial catheter also similar to that shown in FIGS. 15A–B, and shows the arterial catheter to include another specific type of aorta isolation assembly.

FIG. 19B shows a similar view of the direct access endolumenal aortic isolation catheter shown in FIG. 19A, although shows the catheter during another mode of use which isolates the heart from a patient's systemic arterial circulation which is being perfused by an artificial cardiopulmonary bypass pump which is coupled to a proximal internal flow lumen along the catheter.

FIG. 19C schematically shows a partially exploded side view of the distal end portion of an internal valve assembly which is adapted for use in the direct access endolumenal aortic isolation catheter shown in FIGS. 19A–B.

FIG. 19D shows a longitudinally cross-sectioned side view of one particular internal valve assembly such as that shown schematically in FIG. 19C.

FIG. 20 shows a longitudinally cross-sectioned side view of the distal end portion of another direct access endolumenal aortic isolation catheter of the invention during a similar mode of use as shown in FIG. 19A, and shows in shadow a second position for an internal flow valve assembly during another mode of use as described above by reference to FIG. 19B.

FIG. 22A shows a perspective view of the distal end portion of another endolumenal aortic isolation catheter adapted for use in a "beating heart" aortic isolation procedure.

FIG. 22B shows a perspective view of the endolumenal aortic isolation catheter shown in FIG. 15A, except showing the catheter during one mode of use when isolating a proximal anastomosis site along an aorta.

DETAILED DESCRIPTION OF THE EMBODIMENTS

Figure 12:
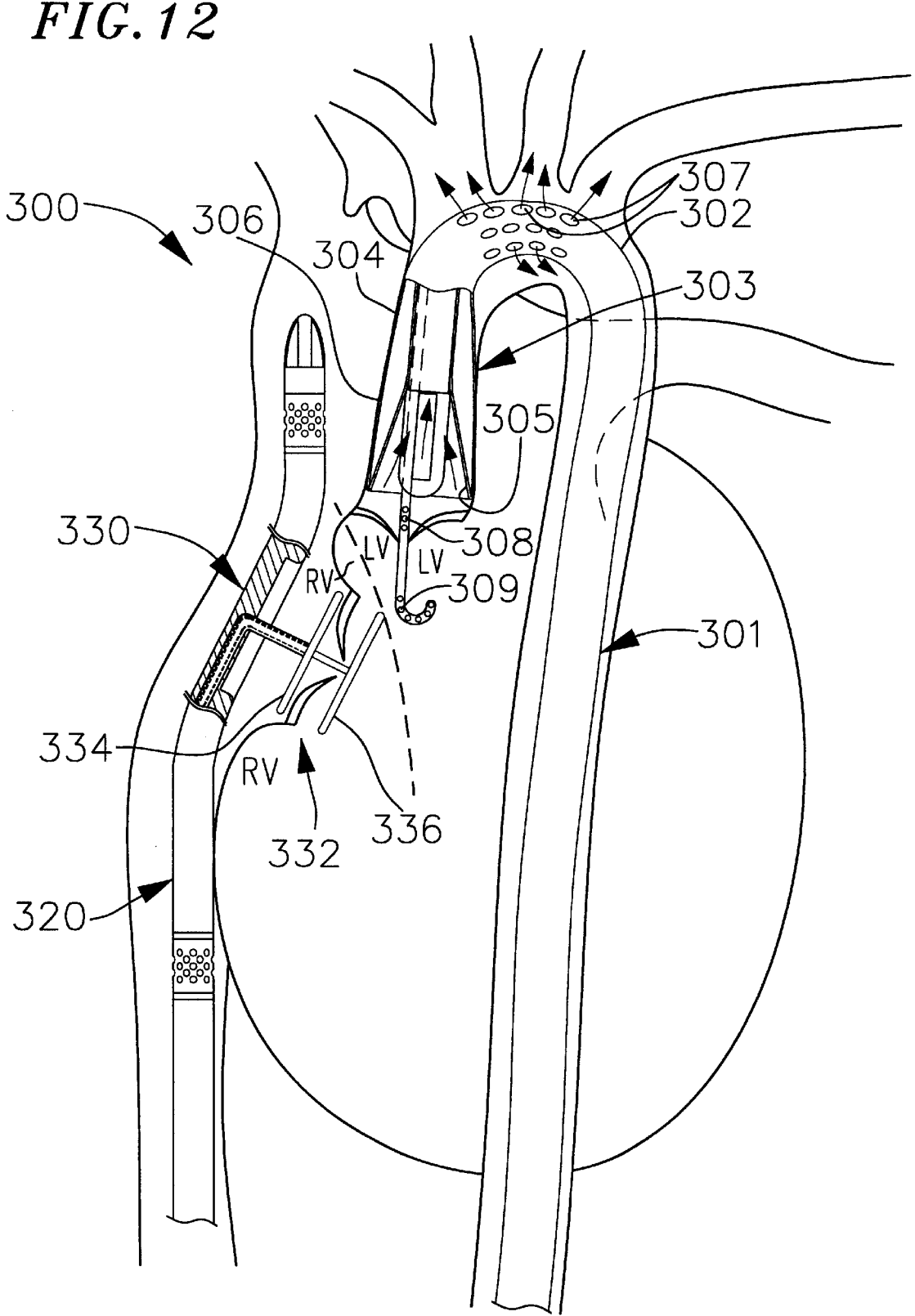
FIG. 12 shows a similar view of the medical device system shown in FIG. 11, although showing an external shunt valve during another sequential mode of use in performing a minimally invasive bypass procedure.
Figure 13:
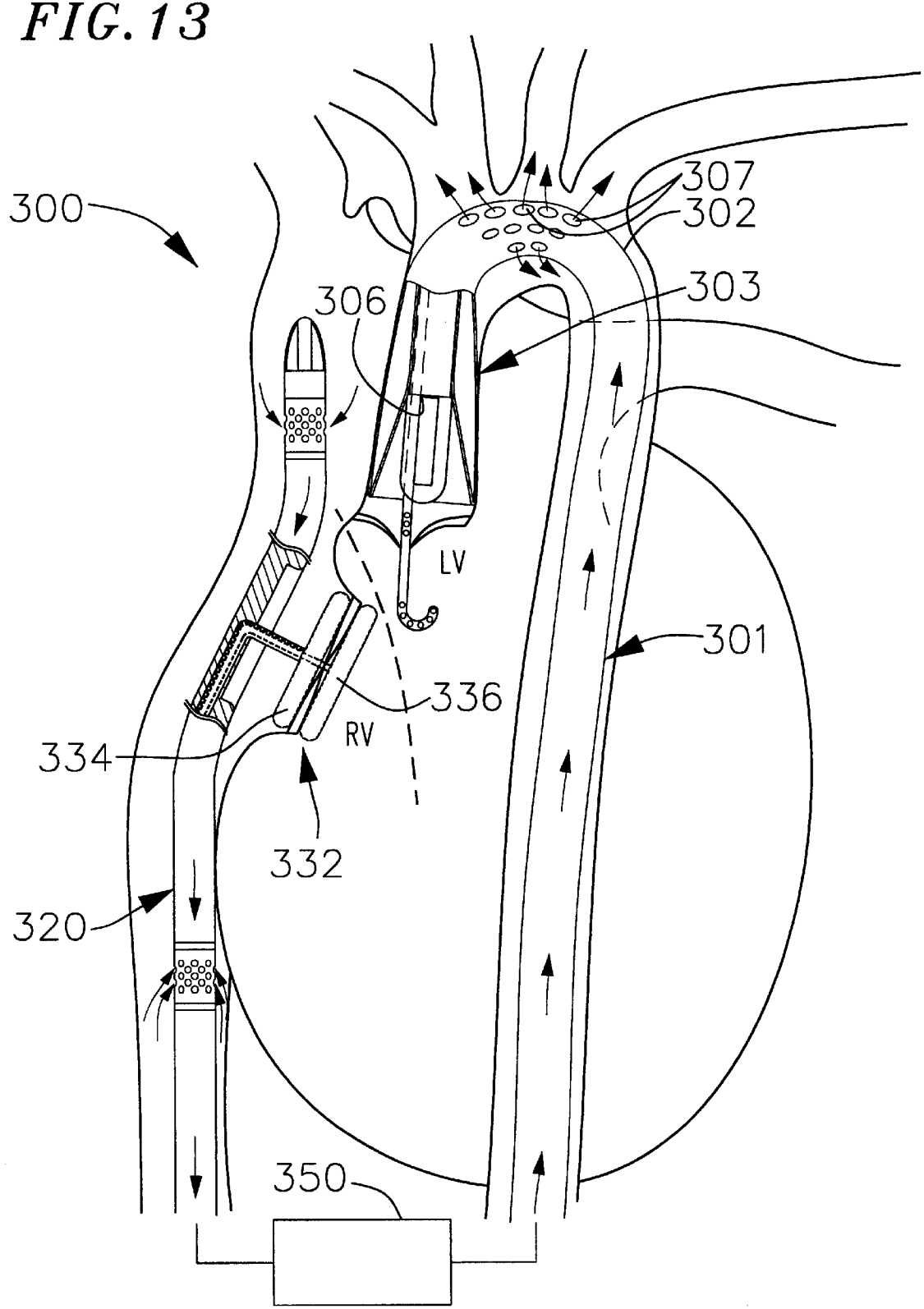
FIG. 13 shows a similar view of the medical device system shown in FIGS. 11–12, although showing the external valve during another sequential mode of use.

FIGS. 1A–8D show varied detail of particular arterial catheter variations which are adapted for use in a minimally invasive cardiac bypass system. FIGS. 9A–10D show varied detail of particular venous catheter variations which are also adapted for use in a minimally invasive cardiac bypass system. FIGS. 11–13 show a minimally invasive bypass catheter system during sequential modes of use in a cardiac bypass procedure. FIGS. 14–17 show the distal end portion of a particular endolumenal aortic isolation catheter having an endolumenal clamp assembly that is a shaped balloon which is adapted to allow a proximal anastomosis to be formed along the aorta while the heart is beating and without substantial loss of blood. FIGS. 18–22B show various modes of a direct access endolumenal aortic isolation system according to the invention.

Cardiac Bypass Arterial Catheter

According to a cardiac bypass aspect of the invention, an arterial catheter is provided which is adapted such that its distal end portion may be positioned within the aortic root adjacent to the left ventricle while its proximal end portion is coupled outside of the body to a cardiopulmonary bypass pump. An external shunt valve anchors to the aortic wall along the ascending aorta between the aortic root and the aortic arch and allows for antegrade aortic blood flow to shunt from the aortic root, through an internal flow lumen within the catheter, and out an intermediate flow port located along the catheter proximally of the external shunt valve, usually in the region of the aortic arch. Either during the cardiac output decline due to cardioplegic effects, or once the heart is substantially arrested from beating and is substantially drained of blood, a distal internal valve closes the internal flow lumen between the distal port adjacent the aortic root and the intermediate flow port in the region of the aortic arch, thereby isolating the left heart chambers from systemic arterial circulation. With the distal internal valve closed, oxygenated blood may then be perfused from the proximally coupled bypass pump, distally through the internal flow lumen, and out the intermediate flow port into the systemic circulation.

Figure 1A:
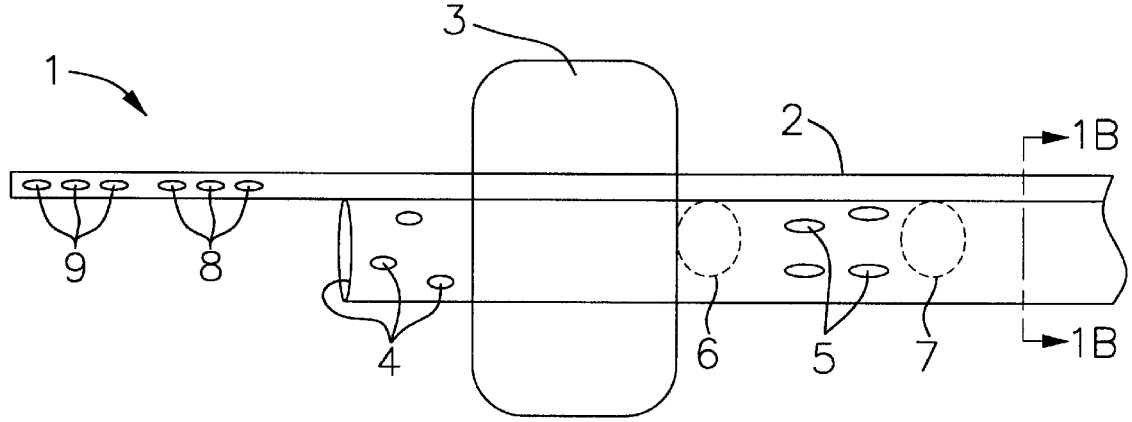
FIG. 1A is a schematic view of one endolumenal aortic isolation catheter which is adapted for use in an endolumenal aortic isolation procedure.

FIG. 1A shows a schematic representation of one arterial catheter for endolumenal aortic isolation such as according to the cardiac bypass procedure just described. Arterial catheter (1) is shown to include an elongate body (2) which includes an external shunt valve (3) on the outer surface of the elongate body's distal end portion. Elongate body (2) further includes an internal flow lumen (not shown in FIG. 1A) which communicates externally of the elongate body through a distal flow port (4), which is located distally of external shunt valve (3), and also through an intermediate flow port (5), which is located along the distal end portion of the elongate body proximally of external shunt valve (3). Each of the particular distal and intermediate flow ports (4, 5) shown in FIG. 1A includes a plurality of apertures which are adapted to allow for sufficient wall rigidity for the catheter to function in a percutaneous transluminal procedure and also to allow for sufficient blood flow to communicate with the internal flow lumen through those ports.

FIG. 1A further shows a distal internal valve (6), which is located within the internal flow lumen distally of intermediate flow port (5), and also a proximal internal valve (7), which is located within the internal flow lumen proximally of intermediate flow port (5). Each of the distal and proximal internal valves (6, 7) is adjustable from an open position, which allows for fluid flow to pass through the internal flow lumen, to a closed position, which is adapted to substantially occlude the internal flow lumen and prevent fluid flow from passing therethrough. Both distal and proximal internal valves (6, 7) are shown in their respectively closed positions in FIG. 1A for the purpose of illustrating their location in relation to intermediate flow port (5). A predetermined combination of the open and closed positions for the respective distal and proximal internal valves (6, 7) shown in FIG. 1A may be selected such that a predetermined flow pattern is provided from the internal flow lumen and through these ports. For example, the distal internal valve (6) may be adjusted to the open position while the proximal internal valve (7) is adjusted to the closed position. In that arrangement, expansion of the external shunt valve (3) within an aortic arch in the region of the aortic root isolates an exterior space between the catheter and the aortic wall from antegrade aortic blood flow while that flow is shunted into distal flow port (4), through the internal flow lumen, out intermediate flow port (5), and into a proximal region of the aorta located proximally of the external shunt valve (3). Alternatively, distal internal valve (6) may be adjusted to the closed position while proximal internal valve (7) is adjusted to the open position. In this arrangement, intermediate flow port (5) may be fluidly coupled to a cardiopulmonary bypass pump via a proximal flow port (not shown) through which the internal flow lumen communicates exteriorly of the elongate body (2) along its proximal end portion (not shown).

Further shown in FIG. 1A are cardioplegia delivery port (8) and ventricular venting port (9), which are each shown to include a plurality of apertures. These ports (8, 9) are shown located on a single, common cannula member which extends from the elongate body (2) distally of the distal flow port (4) and external shunt valve (3). It is further contemplated however that these delivery ports may also be on separate cannula members, and in either case the common or separate cannula member may be fixed relative to the elongate body (2) or may be individually slideable relative to elongate body (2), such as by being coaxially disposed within a lumen extending through the elongate body.

Regardless of the particular cannula design, however, the cardioplegia delivery port (8) is adapted to be positioned within the aortic root such that cardioplegia agent may be delivered to the heart via the coronary arteries stemming therefrom. As such, cardioplegia delivery port (8) may also be positioned adjacent to the distal flow port (4), so long as cardioplegia delivery port (8) is located distally of external shunt valve (3) in order to locally delivery the cardioplegia agent to the left heart and isolate the cardioplegia agent delivered from systemic circulation. The ventricular venting port (9) is adapted to be positioned within the left ventricle, ideally within the apex of that chamber, when the external shunt valve (3) is positioned and anchored within the aortic arch. In this manner the ventricular venting port (9) is adapted to aspirate blood from the left ventricle to create a substantially bloodless field during cardiac surgery when the heart is on bypass.

Figure 1B:
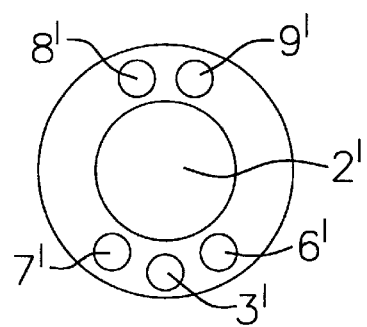
FIG. 1B is a cross sectional view taken along line 1B—1B of FIG. 1A.

FIG. 1B schematically shows the luminal structure of the apparatus of FIG. 1A. Interior flow lumen (2') extends throughout the catheters length between the distal flow port (4) shown in FIG. 1A and a proximal flow port located on the proximal end portion of the elongate body (not shown), and further communicates exteriorly of the elongate body (2) through intermediate flow port (5) shown in FIG. 1A. It is further contemplated that more than one lumen may function as internal flow lumens according to the present invention, so long as the distal and intermediate flow ports may be selectively fluidly coupled and the intermediate and proximal flow ports may also be selectively fluidly coupled. In one variation not shown, a distal internal flow lumen may extend between distal and intermediate flow ports, respectively, while a proximal internal flow lumen extends between proximal and intermediate flow ports, also respectively. According to this variation, separate intermediate flow ports may be provided in communication with the distal and proximal internal flow lumens, respectively, with the distal and proximal internal valves also positioned within the distal and proximal internal flow lumens, also respectively.

FIG. 1B further shows a schematic representation for external shunt valve actuating lumen (3'), distal internal valve actuating lumen (6'), proximal internal valve actuating lumen (7'), cadioplegia delivery lumen (8'), and left ventricular venting lumen (9'). These lumens are respectively coupled to external shunt valve (3), distal and proximal internal valves (6, 7), and cardioplegia and left ventricular venting ports (shown in FIG. 1A). Furthermore, these lumens extend along the proximal end portion of the elongate body (not shown) and are respectively adapted to couple to an external shunt valve actuator, a distal internal valve actuator, a proximal internal valve actuator, a pressurizeable cardioplegia agent source, and a decompression pump. Moreover, the present invention should not be limited to the specific luminal structures and proximal actuation means described herein in detail and modifications and improvements thereof may be suitable according to one of ordinary skill.

FIG. 2A shows an arterial catheter variation which includes one particular internal valve variation that uses an expandable member to selectively occlude flow through an internal flow lumen within the catheter. Arterial catheter (10) is shown in FIG. 2A to include an elongate body (11) which includes an inner tube (12) that forms the internal flow lumen (12'). Distal internal valve (16) and proximal internal valve (17) are expandable members, specifically shown in FIG. 2A as expandable balloons, which are positioned distally and proximally adjacent to intermediate flow port (15), respectively, within internal flow lumen (12'). Intermediate flow port (15) further includes a plurality of apertures through inner tube (12) and through which the internal flow lumen (12') communicates exteriorly of elongate body (11). Each of distal and proximal internal valves (16, 17) is adjustable from a radially collapsed position, which characterizes an open position that allows for fluid to flow through the internal flow lumen, to a radially expanded condition which characterizes the closed position, which is adapted to substantially occlude fluid flow through the internal flow lumen. For the purpose of further illustration, proximal internal valve (17) is shown in the radially collapsed condition, which is the open position, and distal internal valve (16) is shown in the radially expanded condition, which is the closed position.

FIG. 2A further shows a shadowed view of an additional flow port which is a second intermediate flow port (15') positioned proximally of proximal internal valve (17). Where multiple intermediate flow ports are provided according to this variation, a proximal internal valve is positioned proximally of the most proximally positioned intermediate flow port, and an intermediate internal valve is positioned along the internal flow lumen between each adjacent pair of intermediate flow ports. Thus, when second intermediate flow port (15') is included in the catheter shown in FIG. 2A, proximal internal valve (17) would actually be an "intermediate internal valve" and another proximal internal valve (not shown) would be provided along the internal flow lumen proximally adjacent to the second intermediate flow port (15').

Further to the multiple intermediate flow port variation just described, the distal, intermediate, and proximal internal valves may be adjusted to a predetermined combination of their respectively open and closed positions in order to provide fluid communication between either the proximal flow port or the distal flow port and a desired combination of the intermediate flow ports along the elongate body's length. For example, in the case where two intermediate flow ports (15, 15') are provided such as according to FIG. 2A, antegrade aortic blood flow may be shunted proximally through internal flow lumen (12') from the distal flow port (not shown in FIG. 2A) and through only intermediate flow port (15) by adjusting internal valves (16, 17) to their open and closed positions, respectively. Alternatively, by opening both internal valves (16, 17) and closing a proximal internal valve (not shown) located proximally of second intermediate flow port (15'), the antegrade aortic blood flow may be shunted from the aortic root and to proximal regions of the aorta adjacent to both intermediate flow ports (15, 15'). A different combination of internal valves may be adjusted to their respective open and closed positions in order to allow for the preselected distal perfusion of oxygenated blood from a bypass pump coupled to a proximal flow port (not shown) and through only intermediate flow ports (15') or both intermediate flow ports (15', 15).

The controllable perfusion of oxygenated blood along the arterial catheter's length as just described is believed to address a dichotomy of functional requirements normally placed upon a minimally invasive bypass arterial catheter. In one aspect, the arterial catheter must be have a large enough internal flow lumen to carry oxygenated blood from the bypass pump or from the aortic root and into the aortic arch at flow levels which mimic physiological circulation. In another aspect, however, the arterial catheter itself provides occlusive resistance to antegrade arterial flow around the catheter between the intermediate flow ports located within the aortic arch and the catheter's entrance site, usually at the femoral artery. With the ability to perfuse blood flow through a predetermined length of ports along the arterial catheter, much of the desired downstream blood flow may be perfused out from the catheter further down the arterial tree and thus minimize the otherwise occlusive nature of the catheter shaft.

However, the controllable perfusion along the catheter's length according to the multiple valve and port embodiment shown in FIG. 2A has limited controllability. For example, a distal flow port may communicate with a controllable length of ports going distal to proximal along the catheter, but may not communicate with a selected port or ports on a proximal end portion of the catheter at the exclusion of more distal or intermediate ports. A similar limitation is present for the proximal flow port which is adapted to couple to an outlet port of a cardiopulmonary bypass pump. By selecting a specific internal valve to close, the proximal flow port communicates with any number of intermediate flow ports along the catheter proximally of the closed valve, but is isolated from intermediate flow ports located distally of the internal flow lumen. However, it may be desirable to select only one or a few distally disposed intermediate ports for active perfusion from the pump, such as for example an intermediate flow port located proximally adjacent to the external shunt valve which is adapted to be positioned adjacent to the ostia of the carotid arteries from the aortic arch.

Therefore, it is further contemplated that a slideable external sheath may be positioned externally of the catheter shaft and which is adjustable to coaxially block and occlude selected intermediate flow ports along the catheter length. When a patient is on full or partial bypass, the slideable sheath may be positioned to a desired location distally along the catheter shaft such that a predetermined length of distally disposed intermediate flow ports is in communication with the proximal flow port, which predetermined length includes an intermediate port proximally adjacent to the external shunt valve but excludes any intermediate ports located more proximally along the catheter shaft.

Figure 3A:
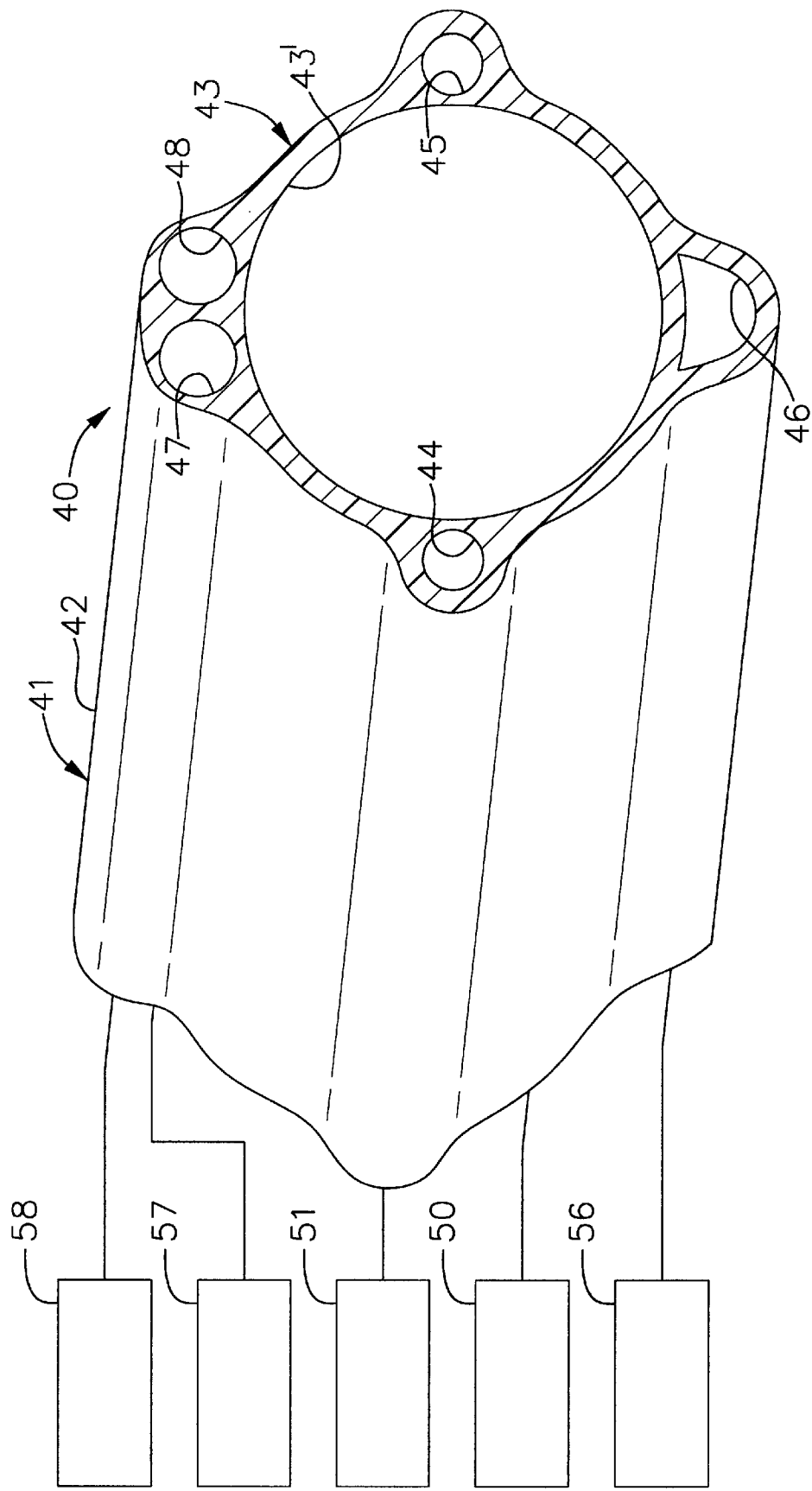

Further to the internal valve variation of FIG. 2A, distal and proximal internal valves (16, 17) are expandable balloons which are shown to be fluidly coupled to distal and proximal valve actuating lumens (18, 19), respectively, through ports formed through the wall of inner tube (12), shown for example in FIG. 2A at internal valve port (14). Various means for coupling the internal valves to their respective actuating members or lumens may be suitable according to one or ordinary skill. One particular means for providing such coupling is shown in FIG. 3C (described in detail below), which is particularly adapted for use in the elongate body variation shown in FIGS. 3A–B, but which may be suitably modified for use in the variation shown and described here by reference to FIG. 2A.

In order to actuate expansion of the balloons which form the internal valves of the FIG. 2A variation, distal and proximal valve actuating lumens (18, 19) are also fluidly coupled to an internal valve actuator at the proximal end portion of the elongate body (not shown). The internal valve actuator may include one common actuator which includes a switch to selectively adjust each valve to its respective open or closed position, or may include separate, individual proximal and distal valve actuators, each coupled to one of the internal valves to adjust it between the respective valving positions. In either the common actuator or individual actuator case, the internal valve actuator generally includes a pressurizeable source of fluid for the balloon internal valve variation shown in FIG. 2A.

The expandable balloons used for internal valves (16, 17) shown in FIG. 2A may be constructed as follows. In one variation, the balloon is constructed from a relatively compliant material which stretches when pressurized, such as for example a latex rubber, polyurethane, or silicone material. In this compliant balloon variation, the balloon may form a simple tubular member or otherwise a relatively small bladder when in the radially collapsed condition which characterizes the open position for the valve. Preferable to the small bladder variation and when placed within the internal flow lumen, the balloon is generally maintained under negative vacuum pressure when in the open position so as to minimize the occlusive nature of the balloon within the flow lumen. Upon pressurizing the relatively compliant balloon, the balloon material stretches and expands to form a balloon-like shape in the radially expanded condition which characterizes the closed position and blocks the internal flow lumen.

In another internal valve variation, the balloon is constructed from a relatively non-compliant material which is preformed into its desired shape in the radially expanded condition and is then subsequently folded into the radially collapsed condition which characterizes the open position for the valve. Such a relatively non-compliant balloon may be comprised of for example a radiated polyethylene material such as linear low or high density polyethylene, polyester terepthalate (PET), polyimide, Nylon, or polyolefin copolymer. Upon pressurization the folded, relatively non-compliant balloon is filled and unfolds to its radially expanded condition which characterizes the closed position and blocks the internal flow lumen.

While the particular internal valve variation shown in FIG. 2A places expandable balloons within the internal flow lumen (12'), other internal valve variations may also be suitable so long as the valve is adjustable from an open position, which allows fluid to flow through the internal flow lumen, to a closed position, which substantially occludes the internal flow lumen and blocks flow therethrough. For example, expandable members such as the balloons shown in FIG. 2A may be positioned adjacent to an inner tube which forms the internal flow lumen, rather than within the flow lumen. According to this variation, expansion of the expandable valve member to the radially expanded condition collapses the adjacent inner tube to create the closed position. By adjusting the expandable valve member to the radially collapsed condition, the inner tube distends to the open position for flow. This variation beneficially removes the expandable member of the internal valve from the flow lumen, which is believed to provide improved hemodynamics through a smoother surface within that lumen.

Further to the "adjacent" expandable valve member variation, the inner tube may be in one aspect a relatively thin-walled, flaccid member such as a thin polyethylene or a TeflonTM tubing such as those used in forming artificial graft members. The thin, flaccid inner tubing which forms the internal flow lumen according to this particular variation may be provided as follows. The thin, flaccid inner tubing which forms the internal flow lumen is a first inner tubing which has a diameter that approximates the inner diameter of a second inner tubing. The expandable balloon resides between the first and second inner tubings which are coaxial. With the internal valve in the radially collapsed condition which characterizes the open position, the first inner tubing distends from pressure within the internal flow lumen and fills the inner confines of the second, coaxial inner tubing. This pressure is provided for example by blood flowing either from the aorta and between the distal and intermediate flow ports or from the cardiopulmonary bypass pump and between the proximal and intermediate flow ports. However, when the internal valve is adjusted to the radially expanded condition which characterizes the closed position, the region of the first inner tubing adjacent to the internal valve is collapsed and the flow lumen is closed.

In a further variation (not shown) of the "adjacent" expandable valve member, the inner tube is a resilient tubular member, such as for example a polyurethane or silicone tubing. According to this variation, the resilient tubing elastically returns to the tubular state upon adjusting the valve to the open position after collapsing the tubing with the valve in the closed position.

In still another expandable internal valve member embodiment (not shown), a mechanically expandable member may be employed to selectively open and close the lumen, as opposed to the hydraulic actuation mechanism of the previously described balloon variations. In one such mechanical valve variation, an expandable cage constructed of coiled or braided metal ribbon or wires may be substituted for the inflatable balloons. In a more detailed embodiment where the cage is positioned within the flow lumen, such a cage would preferably include a distensible polymeric skin in a composite construction in order to substantially occlude flow therethrough during the expanded, closed position. In an alternative embodiment which places the expandable cage member adjacent to the internal flow lumen, however, such a composite skin might not be required.

In another further mechanical valve variation (also not shown), a stop-cock may be placed along the internal flow lumen. The open position for the stopcock variation is characterized a stopcock lumen being registered and aligned with the internal flow lumen. The stopcock's closed position is characterized by the stopcock lumen being out of alignment from the internal flow lumen such that a wall of the stopcock blocks flow through the flow lumen. Adjustment of the stopcock between the open and closed positions may be accomplished mechanically, such as for example by keying a longitudinally adjustable actuating member to a curved surface of the stopcock in a ratchet-and-pawl mechanism to rotate the stopcock.

Still a further mechanical internal valve variation (also not shown) includes a cam assembly with a cam surface that biases a longitudinally adjustable member radially into the internal flow lumen or against an inner tubing to collapse the flow lumen when the longitudinally adjustable member is advanced against the cam surface.

In addition to the several internal valve variations just previously described, other further variations not herein specifically described may also be suitable for use according to the described embodiments, as would be apparent to one of ordinary skill from this disclosure. Further to the shaft construction shown in the arterial catheter embodiment of FIG. 2A, outer tubing (13) is shown surrounding inner tubing (12) as well as the internal valve actuating lumens (18, 19) to form elongate body (11). Alternative variations of acceptable luminal structures for use in forming the elongate body of the FIG. 2A arterial catheter variation are provided in detail in FIGS. 2B–C, each showing a proximal end view through a cross section taken through a catheter's elongate body similar to that shown in FIG. 2A, and each showing an end perspective view of internal valves (16, 17) in their closed and open positions, respectively, within the internal flow lumen.

One specific catheter shaft construction wherein each individual lumen is formed by a separate, individual tubing is shown in FIG. 2B. According to the FIG. 2B shaft variation, a bundle of inner tubings is coaxially surrounded and bound by an outer tubing (13) to form one, overall composite structure. Included within the bundle formed by outer tubing (13) are inner tubing (12), internal valve actuating lumens (18, 19), external shunt valve actuating lumen (20), and cardioplegia delivery and ventricular venting lumens (21, 22).

Unlike the other lumens shown in FIG. 2B, cardioplegia delivery and ventricular venting lumens (21, 22) are shown in FIG. 2B to be formed by a dual lumen extrusion. This particular design is believed to be particularly useful in the bundled composite shaft variation because these particular lumens are preferably extended distally beyond the structures along the elongate body's distal end portion to which the other lumens couple and terminate. For example, the internal valve actuating lumens (18, 19) terminate distally in the internal valves, such as at valves (16, 17) shown in FIG. 2A or at valves (6, 7) shown in FIG. 1A. Furthermore, external shunt valve actuating lumen (20) terminates distally where it is fluidly coupled to the external shunt valve, such as is shown at external shunt valve (3) in FIG. 1A. Still further, the internal flow lumen formed by inner tubing (12) terminates distally at a distal flow port such as distal flow port (4) shown in FIG. 1A.

Another acceptable luminal variation for use in forming the elongate body of an arterial catheter according to the variation shown in FIG. 2A is shown in FIG. 2C. In this variation, a single, four lumen extrusion (32) forms internal flow lumen (32'), an external shunt valve actuating lumen (36), and cardioplegia delivery and ventricular venting lumens (37, 38). Separate, individual internal valve actuating lumens (34, 35) are also shown bundled together with four lumen extrusion (32) within an outer tubing (33) to form the composite shaft of this variation.

The positioning of the separate lumens in the four lumen extrusion (32) of FIG. 2C enhances the ability for those separate lumens to be cut away from the rest of the extrusion where an adaption is to be desirably formed. For example, the portion of four lumen extrusion (32) which forms external shunt valve actuating lumen (36) may be removed distally to where external shunt valve actuating lumen (36) is to be fluidly coupled and adapted to the external shunt valve (not shown), thereby extending a three lumen extrusion containing internal flow lumen (32'), cardioplegia delivery lumen (37), and ventricular venting lumen (38) distally from that adaption. Similarly, the three lumen extension of four lumen extrusion (32) may be further modified distally of the external shunt valve adaption, such that a two lumen extension which forms cardioplegia delivery and ventricular venting lumens (37, 38) may be carried distally of the cut-away portion forming the internal flow lumen (32'). However, in a further variation to the latter example (not shown), the three lumen extension of the four lumen extrusion (32) may alternatively terminate at one location, wherein cardioplegia delivery and ventricular venting lumens (37, 38) may be adapted to a separate dual lumen cannula (or two separate tubings) which carry the lumens further distally where they terminate in their respective distal ports (not shown). One suitable assembly method and material construction for the individual tubings used in the bundled composite shaft variations just shown and described by reference to FIGS. 2B–C may be provided as follows. The outer tubing, such as outer tubing (13) in FIG. 2B or outer tubing (33) in FIG. 2C, is preferably a heat shrinkable polymer which may be comprised of for example irradiated polyethylene, polytetrafluoroethylene (PTFE), fluoro ethyl propylene (FEP), polyester terepthalate (PET), or polyimide. In general, such a heat shrinkable polymer is heated and then expanded from a memory state to an expanded state. In the expanded state, the heat shrink tubing is loaded coaxially over the other inner tubings. During subsequent reheating, the outer, expanded, heat shrink tubing recovers toward the smaller diameter memory state and thus shrinks around the inner tubings to form the composite.

The inner tubings according to the bundled construction just described are preferably adapted to resist deformation and also to retain their luminal integrity under the elevated temperatures of the heat shrink process just described. To that end, placement of mandrels through the bundled tubings is one method which is believed to assist in maintaining these interior lumens during the heat shrink process. In the alternative or in addition to providing mandrels within the respective lumens, one or all of the inner tubings may also be made of an irradiated polymer, which may be similar to that used for the outer heat shrink tubing, although such inner radiated tubings are preferably at their memory state and are collapsed such that they maintain their lumens during the heat shrink step. In a further variation, the inner tubings may be made of a material with a melt temperature or glass transition temperature which is higher than the temperature required to shrink the outer tubing. In still a further variation, one or all of the inner tubings may include a reinforcing member such as a metallic coil or braid imbedded within or laminated with a polymeric tube which assists in maintaining the tubular shape when the polymer might otherwise flow and reconfigure when the bundle is heated with the outer tubing. Further to the heat shrink-bundling variations just described, one or more additional polymeric members may also be provided between or around the individual inner tubings as they are bundled and heated to form the composite. Such additional polymeric members preferably are comprised of a material which melts and flows at the temperatures used to shrink the outer heat shrink tubing. For example, non-irradiated low density polyethylene tubings or beading mandrels may be included around or between the inner tubings, respectively. When the bundle is heated during the heat shrink-bundling process, this additional polymeric tubing or mandrel melts and flows between the inner and outer tubings and provides a binding agent therebetween. Further to this variation, a flexible epoxy or other adhesive material may also be provided between the interior tubings as a binding agent during the heat shrink process.

Figure 3B:
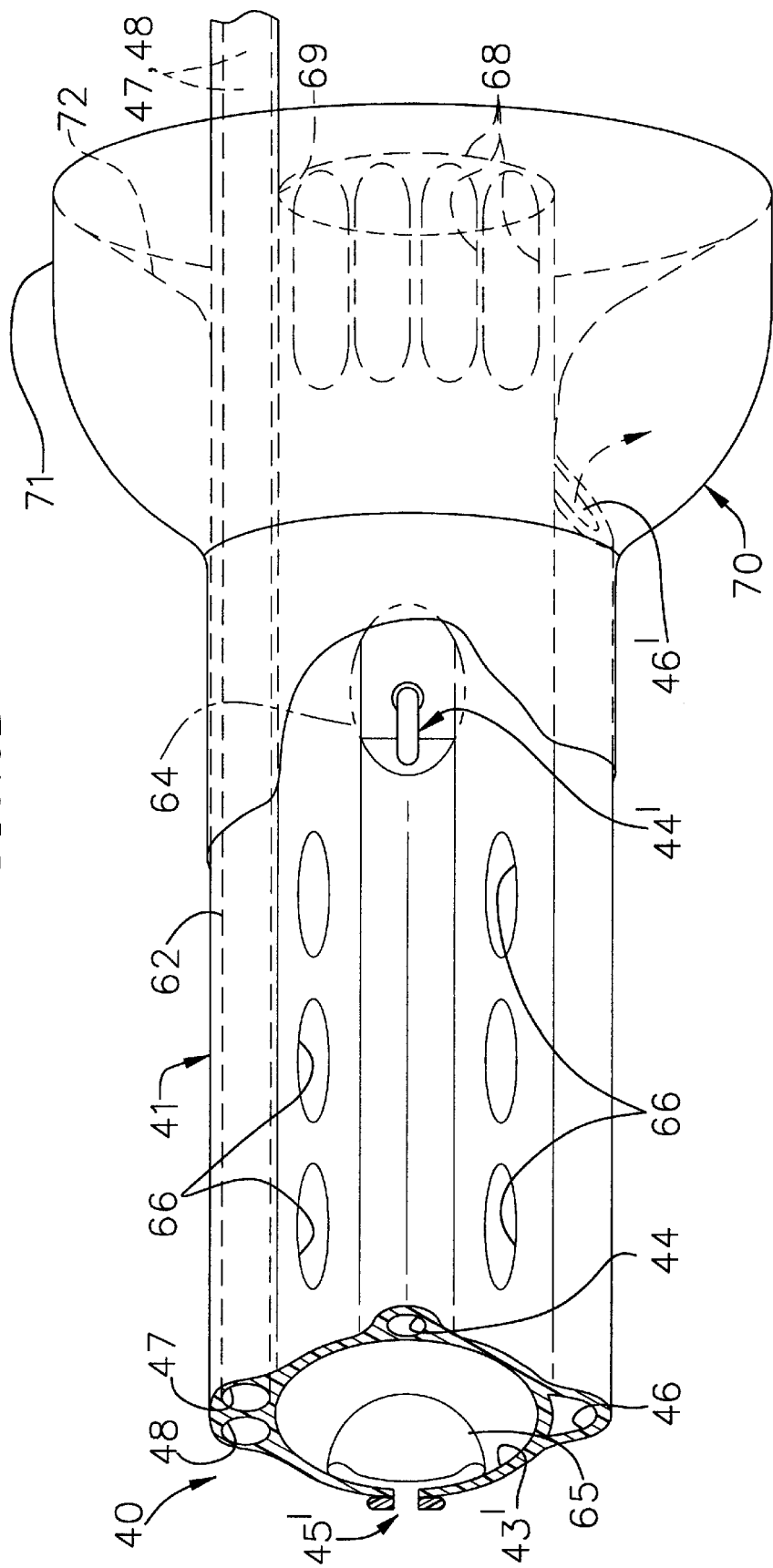

Another particular arterial catheter for use in a cardiopulmonary bypass procedure is shown in two cut-away perspective views in FIGS. 3A–B. FIG. 3A shows proximal end portion (42) of elongate body (41) of arterial catheter (40) in a proximally oriented perspective view which includes a transverse cross section taken through the tubing (43) which forms the elongate body (41). FIG. 3B shows the distal end portion (62) of the same elongate body (41) in a distally oriented perspective view which includes a transverse cross section through a region of the distal end portion (62) which includes proximal internal valve (67). The particular variation shown in FIGS. 3A–B for tubing (43) which forms elongate body (41) includes a single, six lumen extrusion that includes all the lumens of the catheter shaft.

Tubing (43) forms internal flow lumen (43') which includes a proximal flow port that is schematically shown in FIG. 3A as it is proximally coupled to cardiopulmonary bypass pump (50). Internal flow lumen (43') is further shown in FIG. 3B along the distal end portion (62) of the catheter where it communicates externally of the elongate body through distal flow port (68) and intermediate flow port (66). Each of distal flow port (68) and intermediate flow port (66) are shown in FIG. 3B to include a plurality of apertures, wherein those forming distal flow port (68) include apertures along the circumference of a distal extension of tubing (43) beyond external shunt valve (70) and also an end port which terminates the lumen along the longitudinal axis. For the purpose of clarity, however, general reference to "distal flow port" in regards to the internal flow lumen is intended to herein refer to the end port and may optionally include the circumferential apertures shown in FIG. 3B. Further to the end port forming at least in part distal flow port (68), that port may also provide a means for coaxially engaging and tracking over a guidewire, as will be described in some more detail below by reference to FIGS. 11–13. Distal and proximal internal valve actuating lumens (44, 45) are shown in FIG. 3A schematically coupled to an internal valve actuator (51) along proximal end portion (42) of elongate body (41). Internal valve actuator (51) may include a common actuator or two separate individual actuators as was previously described for the FIG. 2A variation. Distal internal valve actuating lumen (44) is further shown in FIG. 3B as it is coupled to the distal internal valve (64), shown in shadow within internal flow lumen (43') via valve coupling means (44') in the distal end portion (62) of elongate body (41). Proximal internal valve actuating lumen (45) is distally coupled to proximal internal valve (65) along the distal end portion of the elongate body via valve coupling means (45'), which is shown in cross-section through proximal internal valve (65) in FIG. 3B.

External shunt valve actuating lumen (46) is also shown in FIG. 3A as it is proximally coupled to an external shunt valve actuator (56), and is further shown in FIG. 3B as it terminates distally in inflation port (46') where it is in fluid communication with external shunt valve (70). External shunt valve actuator (56) is thus adapted to actuate expansion of external shunt valve (70) from a radially collapsed position to a radially expanded position via external shunt valve actuating lumen (46). In the expandable balloon variation shown for external shunt valve (70) in FIG. 3B, external valve actuator (56) shown in FIG. 3A is a pressurizeable fluid source which is adapted to inflate the expandable balloon by filling the balloon with fluid through external shunt valve actuating lumen (46) and inflation port (46').

Further to the expandable balloon which forms external shunt valve (70) shown in FIG. 3B, the balloon is shown to have a shape when in the radially expanded condition which forms an anchor (71) and a funnel (72). More specifically, anchor (71) is formed by a region of external shunt valve (70) which has an outer diameter when expanded that is adapted to engage an interior wall of an aorta in the region of the ascending aorta. Funnel (72) is shown in shadow to have a tapered inner surface with a proximally reducing inner diameter from a relatively large inner diameter portion, which approximates the inner diameter of the aortic root where the external shunt valve (70) is to be positioned, to a relatively small inner diameter portion, which is adjacent to and approximates the outer diameter of distal flow port (68), which may also have a plurality of apertures as shown in FIG. 3B.

Cardioplegia delivery lumen (47) and ventricular venting lumen (48) are also proximally coupled to a pressurizeable cardioplegia agent source (57) and to a decompression pump (58), respectively, as is also shown schematically along the proximal end portion (42) of elongate body (41) in FIG. 3A. These lumens are further shown in FIG. 3B as they extend distally of the distal flow port (68) where they terminate in a common cannula member in cardioplegia delivery and ventricular venting ports (not shown), also respectively.

FIG. 3C shows a more detailed, perspective view of one particular means for coupling an internal valve actuating lumen to an internal valve located within the internal flow lumen according to the various embodiments described, and is shown particularly adapted for use as proximal and distal valve coupling means (44', 45') shown in FIG. 3B for the purpose of illustration.

In more detail, FIG. 3C shows elongate body (90) to include an internal valve actuating lumen (91) which has been cut-away along its distal portion such that the lumen terminates in a valve coupling port (93). An internal valve port (94) is also shown along the cut-away portion of elongate body (90) and communicates with the internal flow lumen (not shown). Internal valve (85) is adapted to the internal flow lumen and also to the internal valve actuating lumen (91) via adaption member (81).

Further detail shown in FIG. 3C for internal valve (85) includes a valve bladder (86), a valve neck (88), a lip (87), and a valve inflation port (89) which communicates with the internal cavity formed by valve bladder (86). This internal valve variation shown is of the relatively compliant type such as that described previously with reference to FIG. 2A, and preferably the individual valve components just described are formed of a uniform material, such as one molded construction.

Valve bladder (86) may be positioned within the internal flow lumen of the catheter as follows. First, a stiffening mandrel (not shown) is inserted into valve bladder (86) through valve inflation port (89) until valve bladder is stretched and distended with a sufficiently narrow width to fit within the internal valve port (94). The stiffening mandrel is then used to insert the stretched valve bladder (86) through the internal valve port (94) until lip (87) acts as a stop around the outer surface of internal valve port (94). Valve neck (88) is thereby coaxially seated within internal valve port (94) and preferably has an outer diameter which is adapted with a tight tolerance to the inner diameter of internal valve port (94), although an adhesive may also be applied to the interface in order to provide a fluid tight seal. Upon removing the stiffening mandrel, valve bladder (86) reconforms to its resting shape in the radially collapsed condition which characterizes the open position within the internal flow lumen, which shape is shown in FIG. 3C and is preferably adapted to optimize hemodynamics for blood flow therearound. Adaption member (81) includes an adaption lumen (82) extending between a proximal adaption port (83) and a distal adaption port (84). Proximal adaption port (83) is adapted to couple to valve coupling port (93), as is shown by a schematic arrow in FIG. 3C. This adaption may be formed by potting the proximal end portion of adaption member (81) which includes proximal adaption port (83) in adhesive within internal valve actuating lumen (91). Alternatively, adaption member (81) may be comprised of an irradiated polymer, preferably an irradiated polyethylene, or still more preferably irradiated high density polyethylene, which is necked to a reduced outer diameter, then advanced within the internal valve actuating lumen (91) through port (93), and subsequently reheated and expanded to engage the interior surface of that lumen (and perhaps melt to that surface where the polymers are of compatible melt temperature).

Adaption member (81) is adapted to couple to internal valve (85) by inserting distal end portion of adaption member (81) which includes distal adaption port (84) into valve inflation port (89). Preferably a seal at this adaption is accommodated with a suitable adhesive between adaption member (81) and the interior surface of internal valve (85) within valve inflation port (89) and neck (88), particular in the case where internal valve (85) is comprised of a material which is not heat compatible with the heatshrink temperatures necessary for reconfiguring a heat memory polymer.

Figure 4A:
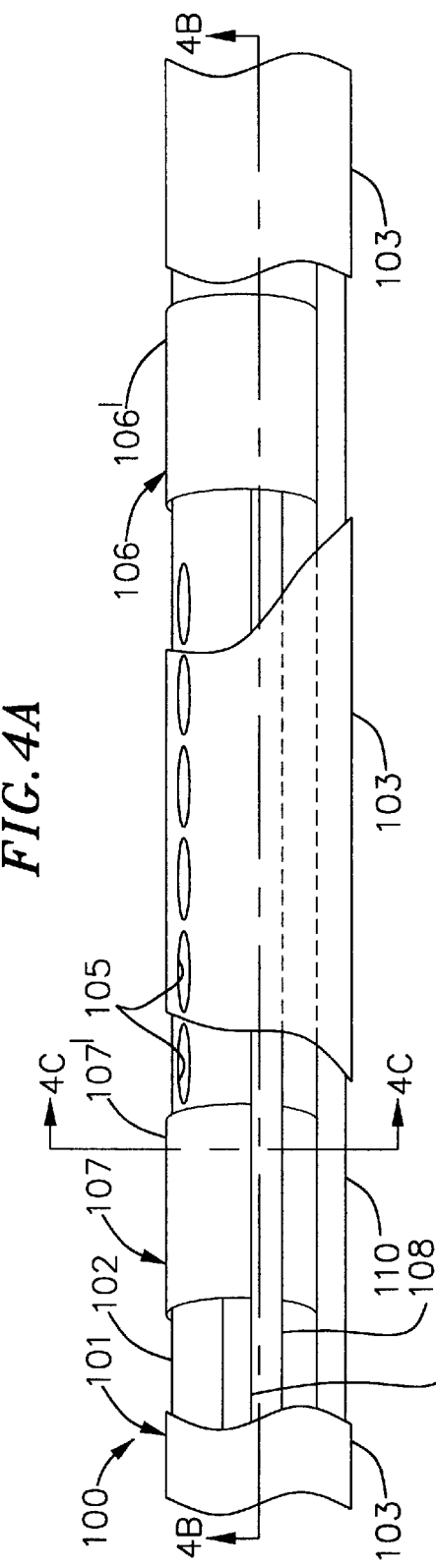
FIG. 4A shows a sectional perspective view of another particular endolumenal aortic isolation catheter, and includes a sectional perspective view of another particular internal valve design for use in selectively occluding an internal flow lumen through the catheter.
Figure 4B:
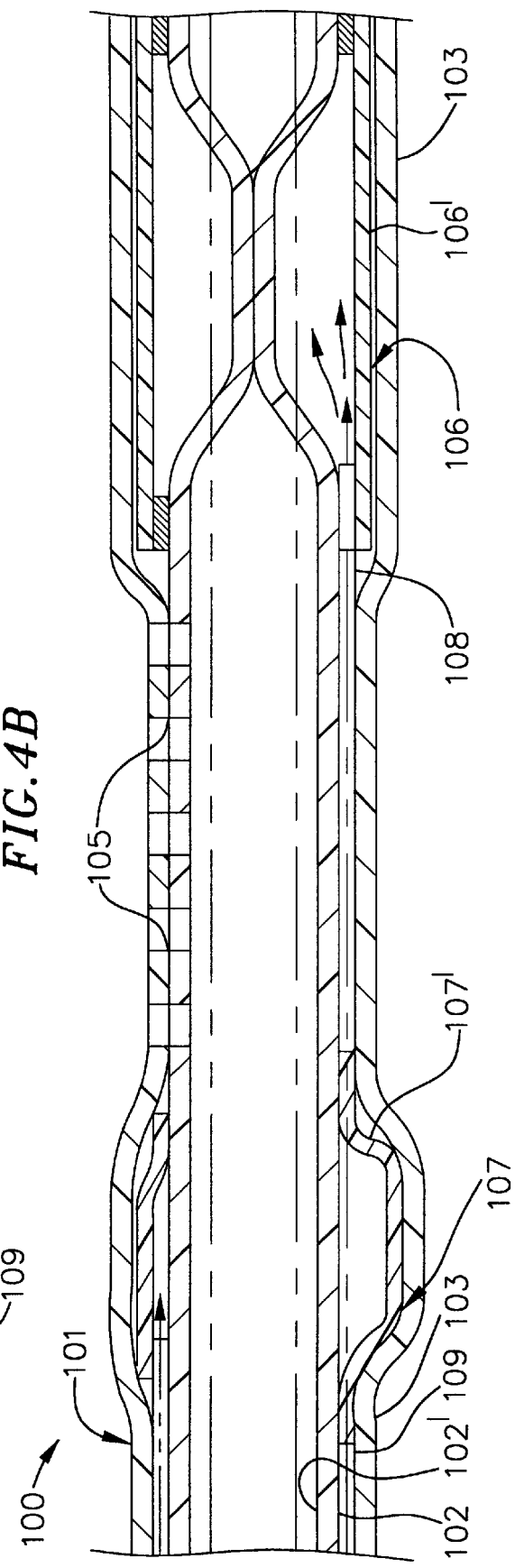
FIG. 4B shows a longitudinal cross-sectional view taken along line 4B—4B through the arterial catheter shown in FIG. 4A.
Figure 4C:
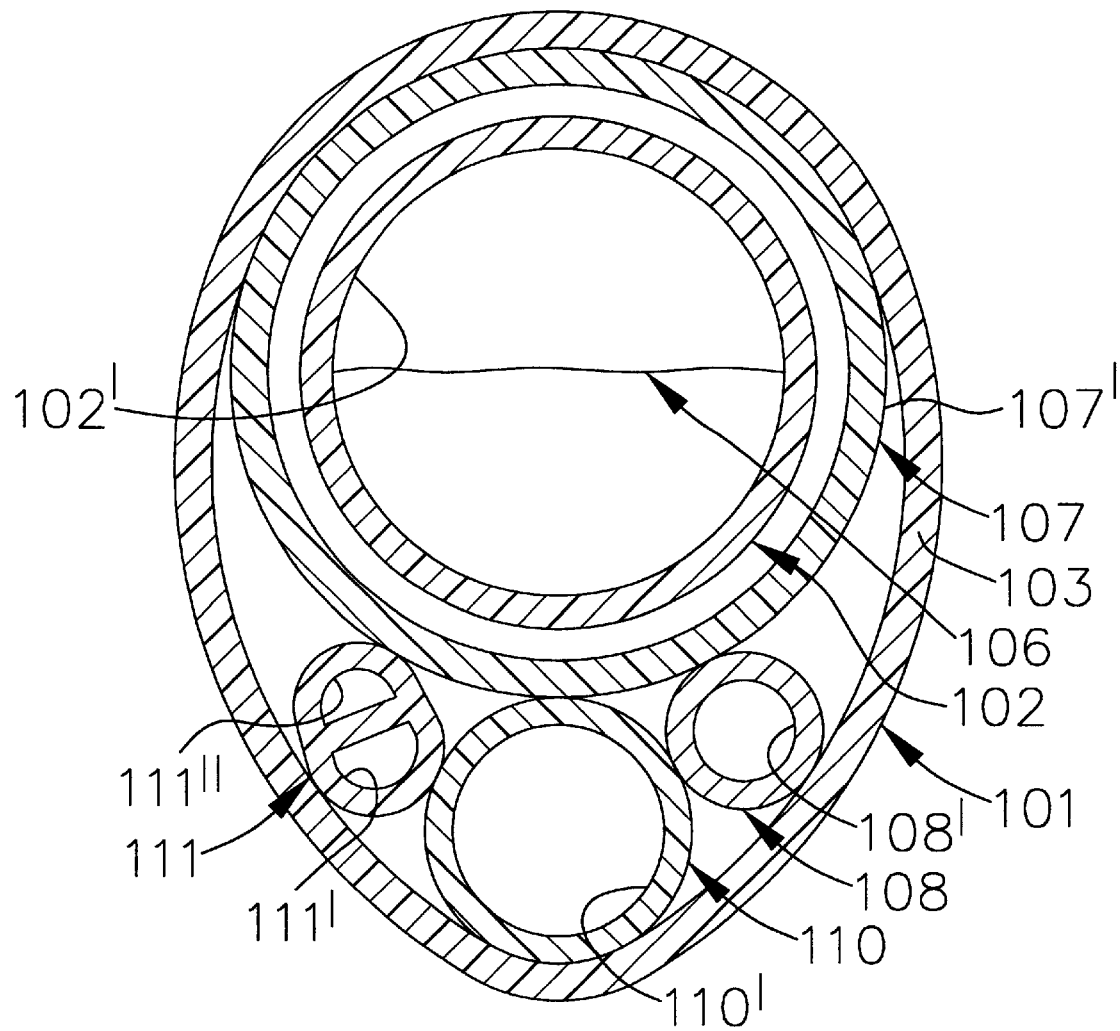
FIG. 4C shows a distally oriented transverse cross-sectional view taken along line 4C—4C through the elongate body shown in FIG. 4A.

Another arterial catheter which includes a further internal valve variation is shown in varied detail throughout FIGS. 4A–C. According to this further variation, an expandable member coaxially surrounds the inner tubing which forms the internal flow lumen and expands inwardly to collapse the internal flow lumen to the closed position. In more particular detail, the distal and proximal internal valves shown in FIGS. 4A–C are formed by coaxially securing pressure cuffs (106, 107), respectively, around inner tubing (102) and distally and proximally adjacent to intermediate flow port (105), which is further shown to include a plurality of apertures extending between those pressure cuffs. Distal internal valve actuating lumen (108) and proximal internal valve actuating lumen (109) are shown distally coupled to the distal and proximal internal valves, respectively, and extend proximally therefrom to a proximal end portion of the elongate body (101) where they are adapted to couple to a pressurizeable fluid source (not shown).

Further to the detail show in FIG. 4B, inner tube (102) is collapsible within the pressure cuffs (106', 107') to form distal and proximal internal valves (106, 107) such that the collapsed walls within those cuffs substantially occlude internal flow lumen (102') at those locations. More particularly regarding distal internal valve (106), the coaxial space between pressure cuff (106') and inner tube (102) is shown potted at each end of pressure cuff (106') with a suitable adhesive to create a seal. Further to the variation shown for proximal internal valve (107), pressure cuff (107') is comprised of a heat shrink tubing, such as has been previously herein described, which has been expanded and then shrunk at its ends to form the seal around the inner tubing. In either the adhesive or heat-shrink seal variation, the relatively coupled actuating lumen is engaged within the outer pressure cuff prior to sealing the ends of the cuff to the inner tubing, such that the final sealed internal valve is in fluid communication with a pressurizeable fluid source as a valve actuator.

For the purpose of further illustration, each of FIGS. 4B–C shows distal internal valve (106) after being pressurized and adjusted to a radially expanded condition which characterizes the closed position, wherein inner tube (102) is shown collapsed to occlude flow through internal flow lumen (102'). Proximal internal valve (107) is alternatively shown in the open position wherein internal flow lumen (102) is open and patent for fluid flow. Moreover, to the extent that the coaxial space between the inner tube (102) and the outer cuff at either internal valve is expanded inwardly into internal flow lumen (102') during pressurization, this internal valve variation is herein considered a coaxial balloon variation.

One particular luminal design for the "coaxial balloon" internal valve embodiment just described is shown in various sectional perspective and transverse cross-sectional views, respectively, in FIGS. 4A and 4C. In general, outer tubing (103) coaxially surrounds and bundles inner tube (102) which forms internal flow lumen (102'), pressure cuffs (106', 107') which form internal valves (106, 107), distal and proximal internal valve actuating members (108, 109) which form distal and proximal internal valve actuating lumens (108', 109'), external shunt valve actuating member (110) which forms external shunt valve actuating lumen (110'), and cardioplegia delivery and ventricular venting member (111) which forms cardioplegia delivery lumen (111') and left ventricular venting lumen (111") (actual lumens formed by the individual tubing members are shown only in FIG. 4C).

This bundled construction just described for the arterial catheter of FIGS. 4A–C may be formed according to the heat shrink bundling process variations previously described herein. Moreover, the particular valve structures described and shown by reference to FIGS. 4A–4C should not be limited to the specific luminal construction shown in variously throughout those Figures.

Figure 5A:
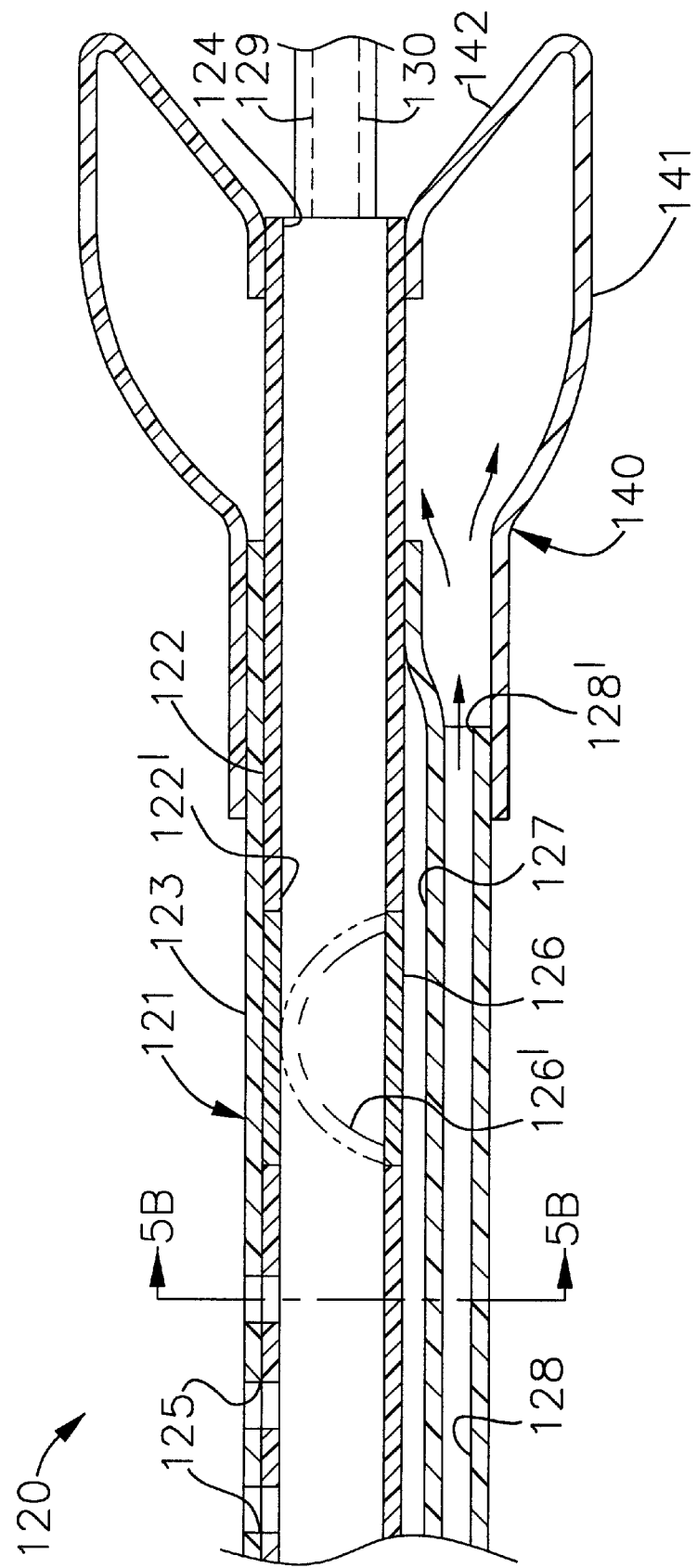
FIG. 5A shows a longitudinal cross-sectional view of another endolumenal aortic isolation catheter for use in an endolumenal aortic isolation procedure.

Still a further arterial catheter variation is shown in FIG. 5A, wherein only one distal internal valve (126) is shown within the internal flow lumen (122') distally of intermediate flow port (125). This variation shown is exemplary of one aspect wherein fluid within internal flow lumen (122') proximally of intermediate flow port (125) is believed to function as a virtual proximal internal valve in the closed position. According to this variation, antegrade aortic blood flowing proximally through internal flow lumen (122') from distal flow port (124) is not allowed to pass through the internal lumen proximally of intermediate flow port (125) when there is a static head of fluid within that proximal lumen. That static head is provided when the proximal lumen is filled with the fluid and the proximal flow port (not shown) is closed. Rather, the shunted antegrade aortic flow travels out of the catheter through intermediate flow port (125). Further to the single internal valve aspect of the FIG. 5A variation, the fluid used to fill the proximal portion of internal flow lumen (122') is preferably an isotonic and non-thrombogenic fluid, and more preferably is an isotonic saline or ringer's lactate solution. To the extent that such solution passively mixes with aortic blood near intermediate flow port (125), it may be desirable to periodically flush the proximal flow lumen through intermediate flow port (125) with additional, fresh fluid in order to clear that mixed blood component from the static column in the lumen proximally of intermediate flow port (125).

FIG. 5A also shows a particular variation for external shunt valve (140) which, similar to the particular variation shown previously in FIG. 3B, is a relatively non-compliant variation of an expandable balloon which is reverted at its distal adaption to inner tube (122) which forms internal flow lumen (122'). In one method of forming the everted adaption, a balloon subassembly (not shown in detail in FIG. 5A) includes an expandable working length bordered on either end by two outwardly extending cuffs of reduced outer diameter. One of the outwardly extending cuffs is sealed around the distal end portion of the inner tube (122), thereby forming a first adaption, such that the balloon's working length extends distally therefrom. The majority of the balloon's working length is thereafter turned inside out and rolled proximally over the first adaption, until the second outwardly extending cuff is inside-out and faces proximally over the catheter shaft. The portion of the balloon's working length which is not turned inside out or rolled proximally over the first adaption is ultimately the region which forms at least a portion of funnel (142), and at least the everted, proximally extending portion of that working length forms anchor (141). A second adaption is then made between the second cuff and the inner tube (122), although proximally of an inflation port (128') through which external shunt valve actuating lumen (128) communicates with the interior chamber formed by external shunt valve (140). The construction for elongate body (121) which forms the luminal configuration for catheter (120) is also shown in FIG. 5A, and also in additional detail in the transverse cross-sectional view through elongate body (121) in FIG. 5B. In this variation, elongate body (121) includes a multi-lumen extrusion which forms internal valve actuating lumen (127), external shunt valve actuating lumen (128), and cardioplegia delivery and ventricular venting lumens (129, 130), respectively. The particular variation shown for external shunt valve actuating lumen (128) actually includes two lumens which are positioned side-by-side along the circumference of the extrusion which forms larger internal valve actuating lumen (127). This particular variation is believed to optimize total luminal cross-section in order to rapidly fill and evacuate external shunt valve (140) of fluid for rapid inflation and deflation, respectively, while further minimizing the contribution of the total luminal cross-section to the outer diameter of the overall shaft assembly. Further to the multi-lumen extrusion, the individual lumens formed thereby may be cut-away for suitable adaptions where desired according to the other previous described multilumen extrusion embodiments.

Figure 5B:
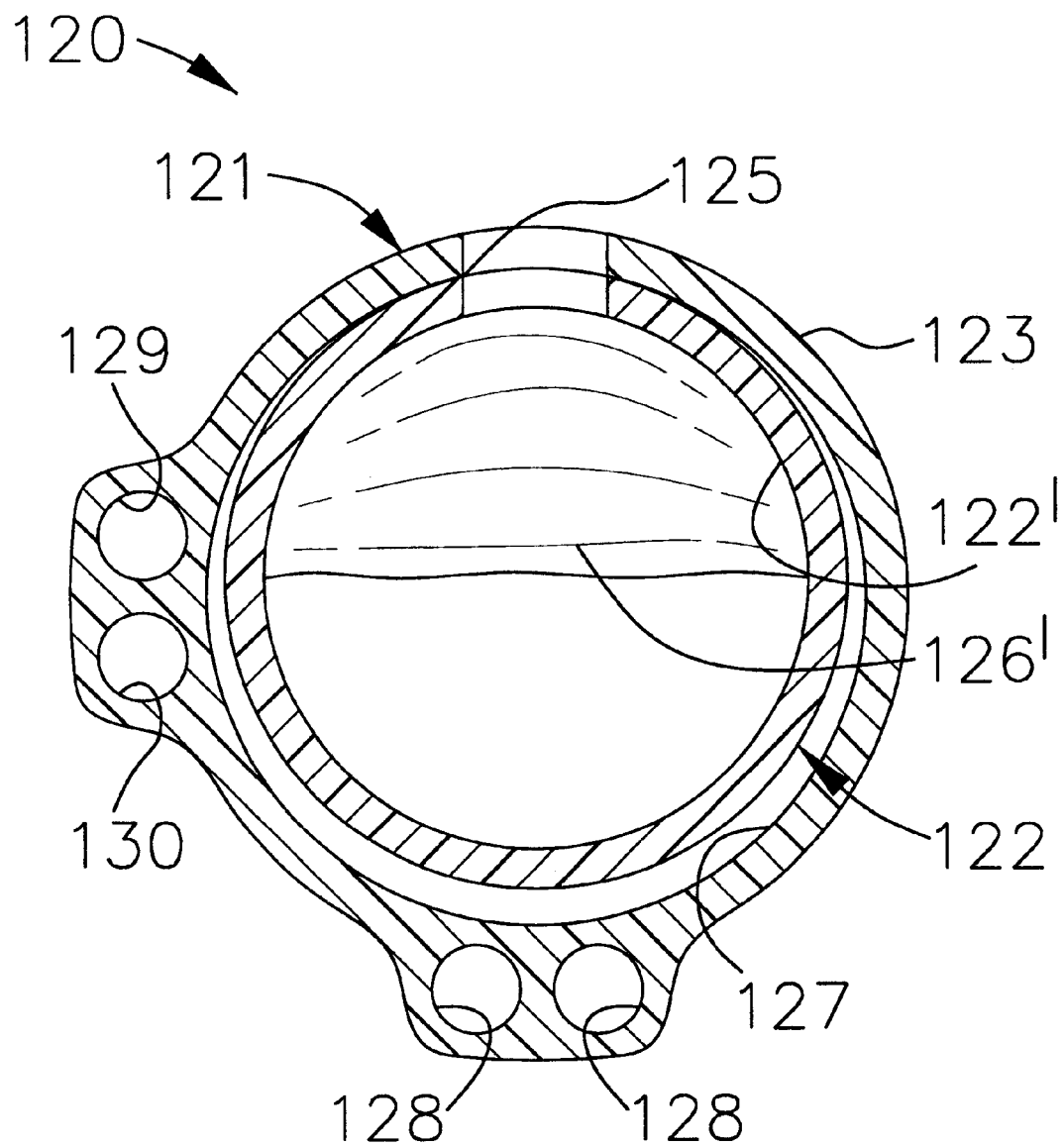
FIG. 5B shows a distally oriented transverse cross-sectional view taken through the elongate body of an arterial catheter similar to that shown in FIG. 5A.

FIGS. 5A–B further show inner tube (122) as it is housed coaxially within internal valve actuating lumen (127) and extends distally therefrom where it terminated in distal flow port (124). Inner tube (122) is also laminated along a relatively thin-walled interior surface of a large round lumen of the multilumen extrusion at a region along the circumference of elongate body (121) opposite external valve actuating lumen (128). This lamination may be formed, for example, by placing an electrically conductive mandrel (not shown), such as a teflon coated stainless steel mandrel, through inner tube (122), forcing inner tube (122) with the mandrel to press against the relatively thin-walled interior surface, and then heating the mandrel such as by induction heating in order to melt the inner tube (122) to that relatively thin-walled inner surface. In this manner, a continuous space is left open between inner tube (122) and the coaxial lumen within which inner tube (122) is housed to thereby form internal valve actuating lumen (127). Further to the resultant actuating lumen, a seal is required in its distal end portion in order to pressurize that lumen for closing internal valve (126), and is shown as a heat seal in FIG. 5A at the distal region of the actuating lumen within external shunt valve (140). However, it is also further contemplated that that seal may be formed in other manners, such as for example by potting the lumen in adhesive.

Figure 6:
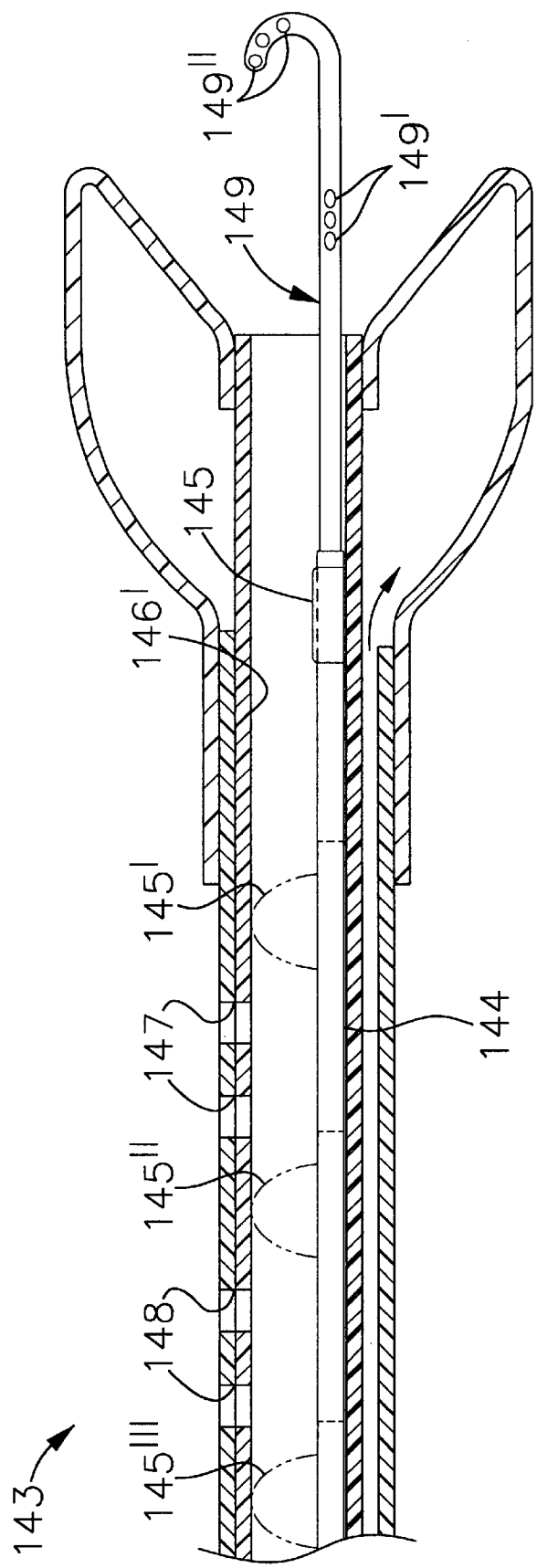
FIG. 6 shows a longitudinal cross-sectional view of another endolumenal aortic isolation catheter for use in performing an endolumenal aortic isolation procedure.

Internal valve (126) is further shown in FIG. 5A to be a relatively collapsible portion of inner tube (122) and may be constructed according to several variations. In one particular variation for internal valve (126), inner tube (122) has variable thickness and is thinner at the region forming internal valve (126) where it is collapsible at a lower pressure than the rest of inner tube (122). In another variation, inner tube (122) has variable material construction along its length, wherein a more flexible and collapsible material is provided in the region forming internal valve (126). Further to this variation, inner tube may be formed generally of a high density polyethylene tubing but for the region forming internal valve (126), wherein a more collapsible tubing such as a low density polyethylene tubing is spliced into continuous member forming inner tube (122). Still further to the variable flexibility version, inner tube may be a fiber reinforced composite, such as one containing a wire reinforcing coil or braid within a polymeric matrix, again but for the region forming internal valve (126) which is void of the reinforcing member and is therefore more amenable to collapsing under pressure. FIG. 6 shows still a further internal valve variation, wherein cannula (144) is slideably engaged within internal flow lumen (146') and provides internal valve (145) internally of that flow lumen (146'), rather than integrating the internal valve in a fixed arrangement along the elongate body of arterial catheter (143). According to this arrangement, the internal valve has variable positioning along internal flow lumen (146') and can be positioned for example at the following locations: distally of flow port (147), as shown at (145'); between flow port (147) and flow port (148), as shown at (145"); or proximally of flow port (148), as shown at (145'").

Still further to FIG. 6, internal valve (145) is further shown in this variation as an expandable balloon which is adjustable from a radially collapsed condition, which characterizes the open position and which allows the cannula (144) to be slideably positioned and repositioned within internal flow lumen (146'), to a radially expanded condition which characterizes the closed position. Moreover, the balloon which forms internal valve (145) is also adapted to radially expand to one side of cannula (144). This design biases cannula (144) toward one side of the tubing which forms internal flow lumen (146'), thereby closing the internal flow lumen (146') with the balloon while maintaining cannula (144) in a relatively straight condition along the side of the internal flow lumen (146') in order to minimize hemodynamic affects that cannula may have on the flow through that flow lumen. Furthermore, it is believed that the internal flow lumen according to this design may be required to have a larger internal diameter in order to make up for the presence of cannula (144) and accommodate the required amount of flow therethrough. However, while internal flow lumen (146') may be enlargened for this purpose, the valve and actuating structures for the internal valve are no longer built into the elongate body of the arterial catheter and therefore the overall profile of the assembly may not be detrimentally increased. Still further to the particular design shown in FIG. 6 for internal valve (145), other designs than a balloon may also be interchangeably constructed according to the other previously described internal valve embodiments as appropriate, such as for example according to other expandable member designs.

Moreover, cannula (144) according to the FIG. 6 embodiment may be one fixed cannula which provides the left ventricular venting lumen and cardioplegia lumen, in addition to an inflation actuating lumen for internal valve (145). Or, in the alternative, cannula (144) may provide an inflation actuating lumen for internal valve (145) and another through lumen through which one or two separate slideably cannulas, such as cannula (149) shown in FIG. 6, may be engaged in order to provide the ventricular venting and cardioplegia delivery functions. According to this last arrangement, the internal valve may be desirably positioned within the internal flow lumen in order to provide the desired flow through the predetermined port or ports, while the cardioplegia delivery and left ventricular venting ports, such as ports (149', 149"), respectively shown in FIG. 6, may be separately positioned through the other slideably engaged cannula or cannulas.

In a further embodiment (not shown) to the "internal valve on a slidable cannula" variations just shown and described by reference to FIG. 6, the slidable cannula with the expandable member of the internal valve may alternatively be positioned within a passageway or lumen which is adjacent to the tubing which actually forms the flow lumen through the catheter, rather than actually positioning these elements within the flow lumen itself. According to this further variation, the tubing forming the internal flow lumen may be a flacid material which distends for relatively unrestricted flow under blood pressure while the valve is in the open position, and which is otherwise collapsible to occlude flow when the valve is in the closed position. Still further, the tubing forming the flow lumen may be an elastomeric tubing which elastically adjusts between collapsed and open conditions for flow according to the respective closed and open positions for the valve. These alternative constructions according to this variation are further developed above.

A further alternative external shunt valve variation to that shown and described by reference to FIG. 5A is shown in various detail and modes of operation throughout FIGS. 7A–D. According to this variation, the expandable balloon is comprised of a fiber reinforced composite which includes a predetermined, patterned mesh of relatively non-compliant fibers which are imbedded or laminated within a matrix of a relatively compliant polymeric material. A controlled and varied pattern of the reinforcing fibers along the length of the balloon is used to vary the longitudinal compliance along the balloon's length such that the funnel for the balloon valve is formed during inflation of the balloon.

Figure 7A:
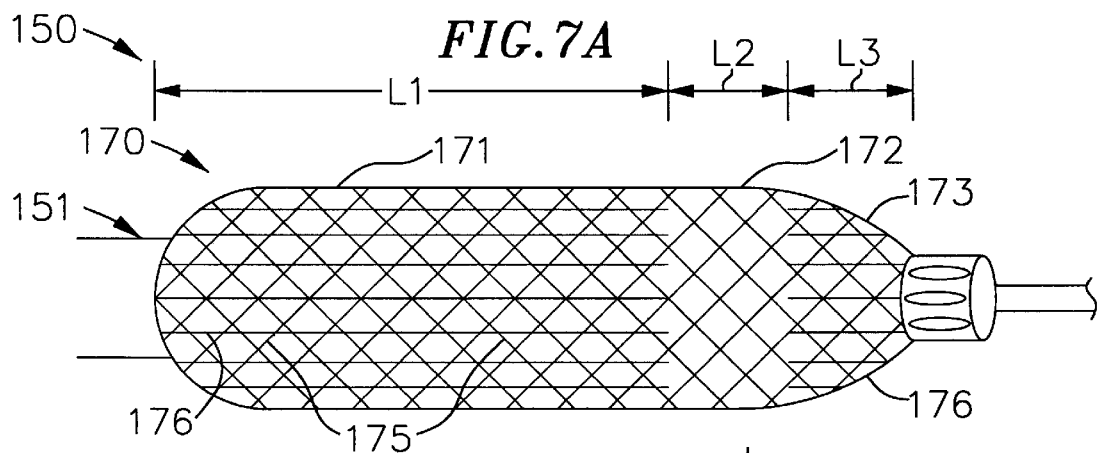
FIG. 7A shows a perspective view of the distal end portion of another endolumenal aortic isolation catheter for use in performing an endolumenal aortic isolation procedure.
Figure 7B:
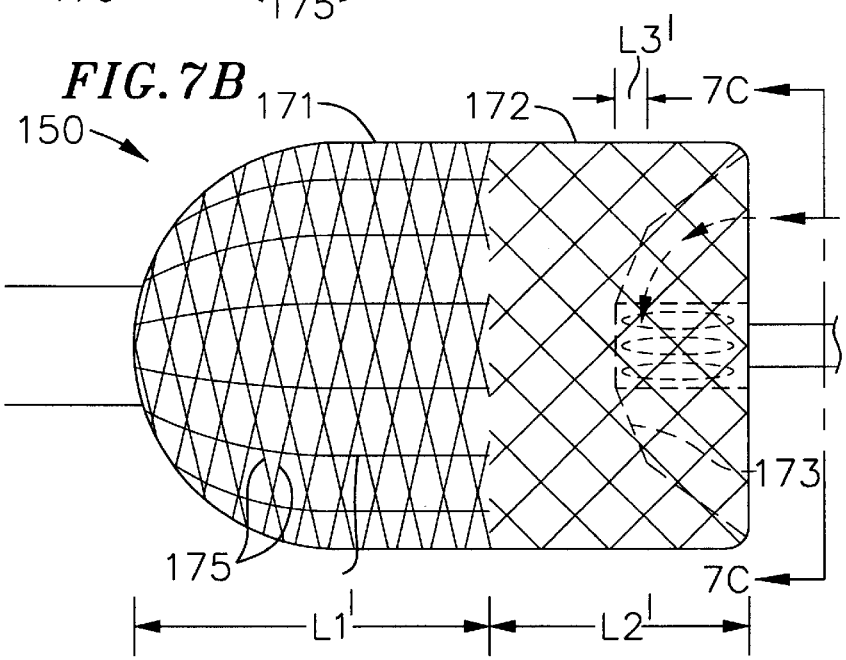
FIG. 7B shows a perspective view of the same distal end portion of the endolumenal aortic isolation catheter shown in FIG. 7A, although showing the external shunt valve in a radially expanded condition which characterizes a shunting position.
Figure 7C:
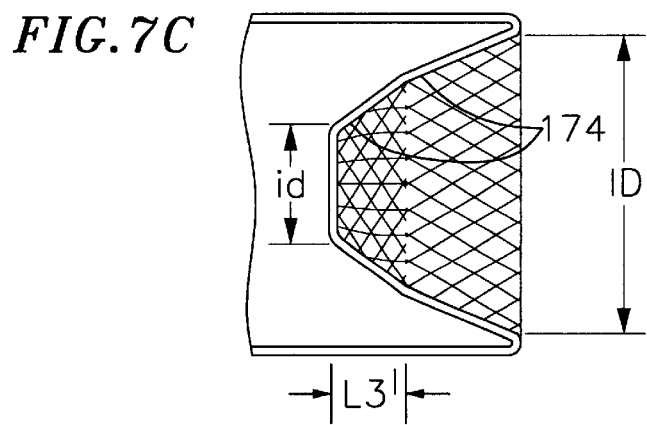
FIG. 7C shows a sectional longitudinal cross-section taken along line 7C—7C through the funnel formed by the external shunt valve shown in FIG. 7B.

More specifically, FIG. 7A shows external shunt valve (170) in a radially collapsed condition along the distal end portion of elongate body (151) of arterial catheter (150). External shunt valve (170) includes a proximal portion (171), a distal shoulder (172), and a distal taper (173). Proximal portion (171) and distal taper (173) each include similar radially oriented fibers (175) and also longitudinal fibers (176), whereas distal shoulder (172) includes similarly radially oriented fibers (175) and does not include longitudinal fibers. The longitudinal fibers (176) in proximal portion (171) and distal taper (173) are relatively non-compliant and allow for little or no longitudinal compliance to the composite balloon skin in those regions during inflation. The radially oriented fibers (175) are also relatively non-compliant, but have both a longitudinal and also a radial component to their angled orientation. Due to this angled orientation for radially oriented fibers (175), some of both the radial and also the longitudinal compliance of the matrix polymer is maintained for the composite balloon skin despite the presence of these fibers. A progression of balloon expansion for the engineered composite variation just described is shown by comparing FIG. 7A, which shows the radially collapsed condition for exterior shunt valve (170), to FIG. 7B, which shows external shunt valve (170) in the radially expanded condition for the valve. This progression further illustrates the fiber reinforced composite variation as it forms the funnel in the shunting position according to external shunt valve of the present invention. As is shown in FIG. 7A, proximal portion (171), distal shoulder (172), and distal taper (173) have lengths L1, L2 and L3, respectively when the external shunt valve (170) is in the radially collapsed condition. Observing the relative lengths L1', L2', and L3' for the radially expanded condition shown in FIG. 7B, only distal shoulder length L2' is longer than distal shoulder length L2 due to the unique ability for distal shoulder (172) to strain longitudinally under the stress of the inflation pressure within the balloon. This variable longitudinal strain between the distal shoulder (172) and distal taper (173) produces the funnel, which is shown in further cross-sectional detail in FIG. 7C. However, because all regions of the balloon have substantially the same radial or circumferentially oriented fiber reinforcement from fibers (175), including distal shoulder (172), it is believed that a relatively constant radial compliance and therefore expanded outer diameter is provided along the working length of the balloon between the tapers, as is further shown in FIG. 7B.

Figure 8A:
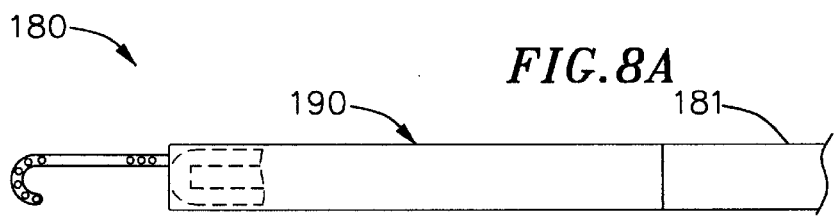
FIGS. 8A–B show perspective views of another endolumenal aortic isolation catheter, wherein an external shunt valve is shown in radially collapsed and radially expanded conditions, respectively, which characterized the open and closed positions, respectively, for the valve.
Figure 8B:
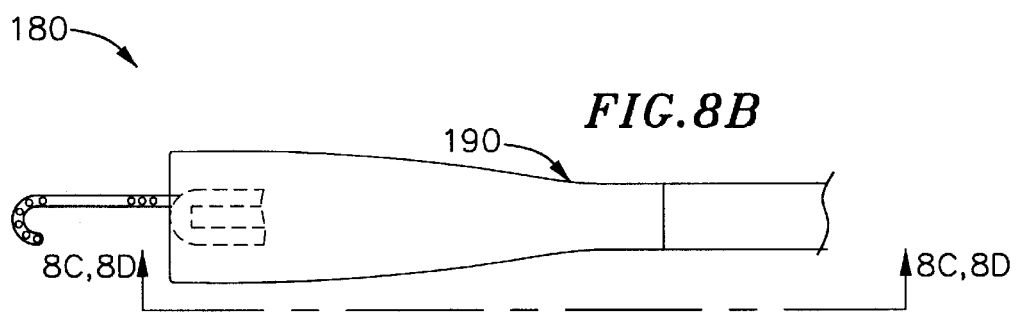
Figure 8C:
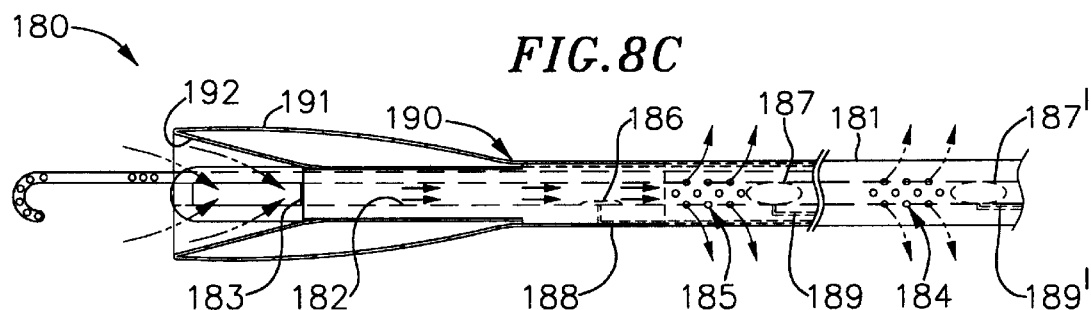
FIG. 8C shows a longitudinal cross-section taken along line 8C—8C through the endolumenal aortic isolation catheter shown in FIG. 8B, and shows internal valves adjusted to a predetermined combination of their respective open and closed positions.
Figure 8D:
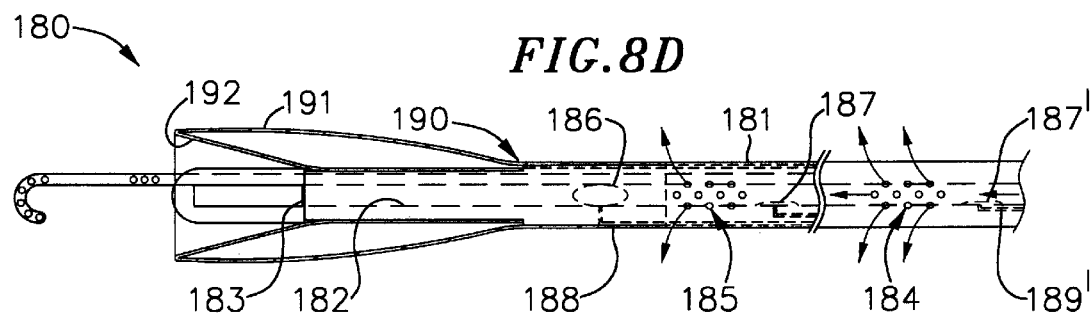
FIG. 8D shows a similar longitudinal cross-section as FIG. 8C and taken along line 8D—8D of the catheter shown in FIG. 8B, although showing the internal valves adjusted to a different predetermined combination of their respective open and closed positions.

For the purpose of further illustrating the broad functional aspects of the various particular arterial catheter embodiments just provided with reference to FIGS. 2A–6C, various views of one particular arterial catheter variation is shown throughout FIGS. 8A–D during various modes of use. FIG. 8A shows arterial catheter (180) with an external shunt valve (190) in a radially collapsed condition which characterizes the open position for the valve. FIG. 8B provides a perspective view of arterial catheter (180) with the external shunt valve (190) adjusted to the radially expanded condition which characterizes the closed position for the valve. Detailed modes for adjusting the internal valves within arterial catheter (180), during radial expansion of external shunt valve (190) in the closed position, are shown in FIGS. 8C–D.

FIG. 8C shows arterial catheter (180) during one operational mode which is adapted to shunt antegrade aortic blood flow from the aortic root (distally to the expanded external shunt valve), through an internal flow lumen within the catheter, and out of that flow lumen and into the systemic arterial circulation at a proximal region of the aortic artery. According to this mode, distal internal valve (186) is in the open position and proximal internal valve (187) is in the closed position. Antegrade aortic blood is depicted by arrows as it enters the funnel (192) formed by external shunt valve (190), through distal flow port (183), along internal flow lumen (182), and out intermediate flow port (185) proximally of external shunt valve (190). The same arterial catheter (180) is further shown in FIG. 8D after adjusting the external and internal valves to another predetermined combination of their respectively open and closed positions such that the catheter is adapted to isolate the systemic arterial circulation from the aortic root distally to the external shunt valve (190) and also distally of the distal internal valve (186) within internal flow lumen (182). The valving configuration of FIG. 8D further adapts arterial catheter (180) to provide retrograde flow of oxygenated blood from a cardiopulmonary bypass pump (not shown), distally through the internal flow lumen (182), and into the systemic circulation proximally of the external shunt valve (190). This combination of valve adjustments is shown to include adjusting external shunt valve (190) to the shunting position, distal internal valve (186) to its closed position, and proximal internal valve (187) to its open position.

A second intermediate flow port (184) is also shown in shadow in FIGS. 8C–D and is optionally provided according to the arterial catheter modes herein described. Concomitant with the inclusion of second intermediate port (184), proximal internal valve (187) becomes an intermediate internal valve by virtue of its position between the adjacent pair of intermediate flow ports (185, 184). Proximal internal valve (187') is thus provided proximally of second intermediate flow port (184), as is shown in shadow in FIGS. 8C–D. The inclusion of second intermediate flow port (184) in the perfusion of oxygenated blood through the catheter is shown in both the antegrade aortic flow and retrograde bypass flow scenarios with dashed lined arrows in FIGS. 8C–D, respectively. As was previously described, the antegrade aortic flow through both intermediate flow ports as shown in FIG. 8C is achieved by closing proximal internal valve (187') and opening distal internal valve (186) and proximal internal valve (187), which in this case is actually an intermediate internal valve. The alternative blood perfusion from the bypass pump as shown in FIG. 8D is permitted through the second intermediate flow port by opening proximal internal valve (187') and either closing proximal internal valve (187), which isolates perfusion flow through only the second intermediate flow port (184), or opening internal valve (187) and closing distal internal valve (186), which perfuses the blood from the pump through both the intermediate flow ports (185, 184).

Venous Catheter

The venous catheter modes herein described are generally adapted to isolate the right heart from vena caval blood flow and to aspirate that flow into a cardiopulmonary bypass pump without circumferentially engaging the interior wall of the vena cavae. Specific embodiments are shown and described in detail in FIG. 9 and FIGS. 10A–D.

Figure 9:
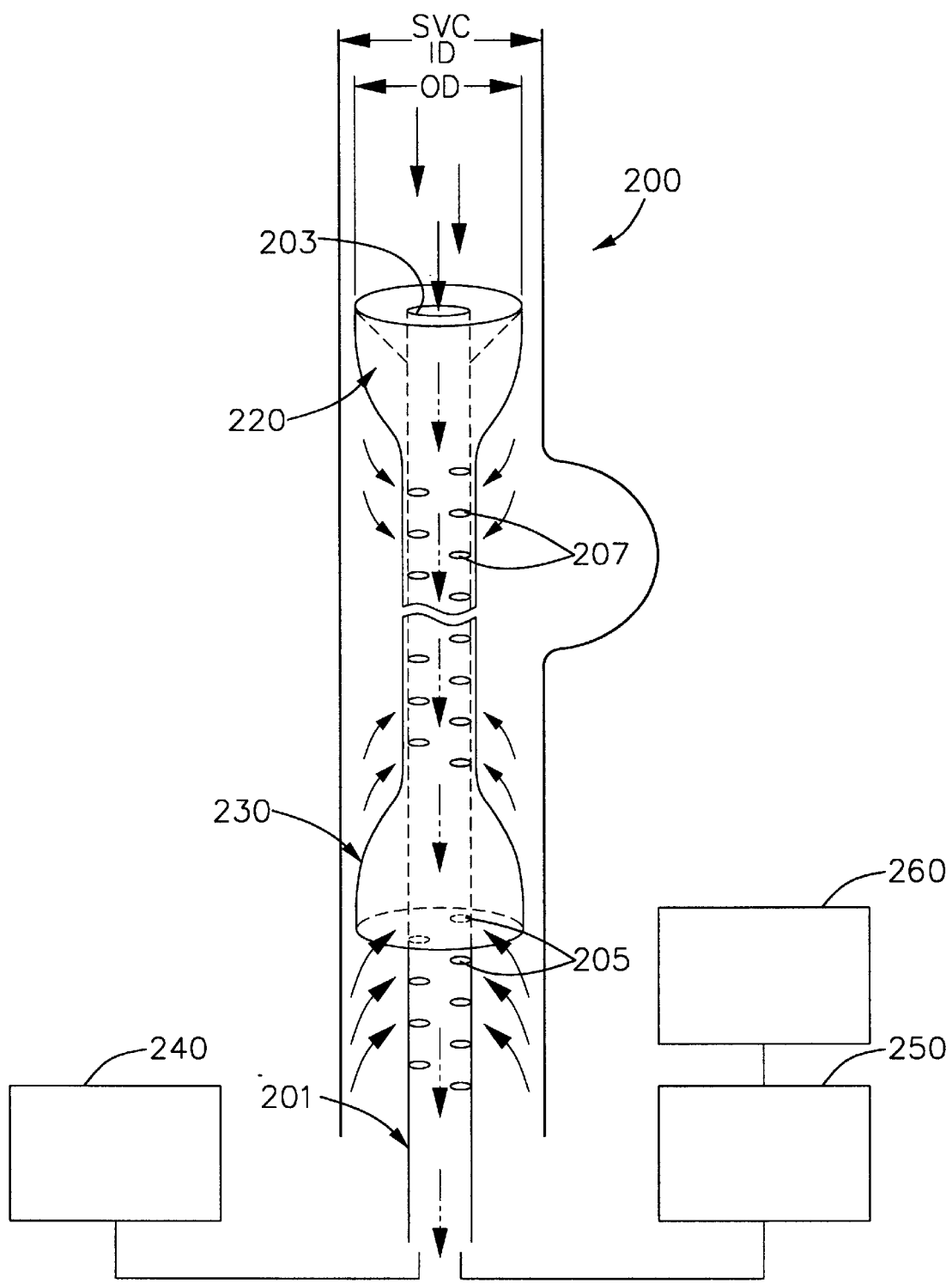
FIG. 9 shows a perspective view of a endolumenal venous isolation catheter assembly during use in isolating a right ventricle from the vena cavae and while aspirating venous blood from the vena cavae.

One venous catheter variation which is adapted to substantially isolate the right heart chambers from the venous flow in the vena cavae and which achieves this isolation without engaging the walls of the vena cavae is shown during use in a vena cavae in FIG. 9. More specifically, venous catheter (200) includes an elongate body (201) which includes a distal flow port (203) located along the elongate body's distal end portion and an intermediate flow port (205) located along the distal end portion proximally of distal flow port (203). A distal external valve (220) is located along the distal end portion proximally adjacent to distal flow port (203), while an intermediate external shunt valve (230) is positioned distally adjacent to intermediate flow port (205).

Each of the distal and intermediate external valves (220, 230) shown in the FIG. 9 variation is adjustable from a radially collapsed condition, which characterizes an open position, to a radially expanded condition, which characterizes a closed position. The respective open positions for these valves are adapted to allow for percutaneous transluminal delivery of the elongate body's distal end portion into the region of the vena cavae adjacent to the sinus venarum in the right heart, and is also adapted to allow for venous blood flow to pass from the superior and inferior vena cava and into the right heart chambers through the sinus venarum or vena caval inlet where the vena cavae communicate with the right atrium. The alternatively closed positions for the distal and intermediate external valves (220, 230) is adapted to substantially isolate the right heart chambers from vena caval blood flow and aspirate that flow into a cardiopulmonary bypass pump, as is described in more detail below.

FIG. 9 shows each of the distal and intermediate external valves (220, 230) in the radially expanded condition which characterizes its respective closed position. Each of the valves in the radially expanded condition has a working length with an outer diameter which is slightly less than the inner diameter of the superior vena cava, in the case of distal external valve (220), or the inferior vena cava, in the case of intermediate external valve (230). This relationship is shown for example in FIG. 9 by comparing distal external valve outer diameter OD with superior vena cava inner diameter SVC ID. The closed position for the valves therefore does not completely occlude the relative vena cava, but instead only substantially occludes the vessel lumen and thereby increases the pressure upstream of the respective valve. By positioning each valve downstream and adjacent to a flow port into an internal lumen of the catheter, the increased pressure due to the valve expansion thereby increases the pressure adjacent to the adjacent flow port and enhances aspiration of blood through that port and into the respectively coupled internal flow lumen. The aspirated blood further travels proximally along the flow lumen, out of the lumen through a proximal flow port (not shown), and into a cardiopulmonary bypass pump, shown schematically at cardiopulmonary bypass pump (250), which may be any suitable pump such as the "BioPump" described above, according to one of ordinary skill.

The external valves shown and described for the venous catheter variation of FIG. 9 therefore do not completely isolate the right heart chambers from vena caval blood, but instead do so only substantially by creating a significant occlusion to flow into those heart chambers and aspirating the blood with suction from an external pump at a location opposite that artificial occlusion from the heart. However, it is contemplated that the "substantial" aspiration of blood and "substantial" isolation of the heart may still provide some degree of leakage of vena caval blood around the external valves and into the heart.

Further to the external valve leakage just described, a leakage flow port (207) is further shown in FIG. 9 between distal external valve (220) and intermediate external valve (230). Leakage flow port (207) enhances additional aspiration of the blood which might leak around the distal and intermediate external valves (220, 230) and into the region of the vena cava adjacent to the sinus venarum.

It is believed that each of the distal, intermediate, and leakage flow ports (203, 205, 207) preferably communicate proximally to the cardiopulmonary bypass pump via independent and separate flow lumens. For example, a distal flow lumen (not shown) may fluidly couple a distal flow port (203) to a proximal flow port (not shown) which is coupled to cardiopulmonary bypass pump (250)(proximal flow port coupling shown schematically), an intermediate flow lumen (not shown) may fluidly couple intermediate flow port (205) to cardiopulmonary bypass pump (250), and a leakage flow lumen (not shown) may couple leakage flow port (207) to cardiopulmonary bypass pump (250). Further to such a multiple venous aspiration luminal design, it is further believed that a higher negative pressure may be desirable at the the distal flow port (203) than the other ports. Moreover, another acceptable variation provides a common internal flow lumen (not shown) between distal and intermediate flow ports (203, 205), with a separate independent flow lumen (not shown) coupled to leakage flow port (207).

According to this latter variation, the blood which leaks around and between distal and intermediate external valves (220, 230) and which is adjacent to leakage flow port (207) is at a significantly lower pressure than the blood adjacent the distal and intermediate flow ports (203, 205) on the upstream side of either of external valves (220, 230), respectively. If leakage flow port (207) were coupled to the same internal flow lumen as distal or intermediate flow ports (203, 205), such a coupling may provide a shunt around the external valves and cause an undesirable flow of blood from the high pressure zones adjacent to distal and intermediate flow ports (203, 205), through the common internal flow lumen, and outwardly into the low pressure zone through leakage flow port (207). By segregating the internal flow coupled to leakage flow port (207) from the internal flow lumen coupled to the other high pressure flow ports, the relatively low pressure flow is isolated from the relatively high pressure flow.

Further to the FIG. 9 variation, it is further contemplated that distal external valve (220) may be provided at the exclusion of intermediate internal valve (230). The venous blood pressure in the inferior vena cava is lower than that in the superior vena cava, and it is believed that the blood in the inferior vena cava may be sufficiently aspirated merely through applied suction from the external pump at intermediate flow port (205). In the higher pressure zone at the superior vena cava, however, it is believed that at least a partially occlusive cuff such as distal external valve (220) may be required in order to prevent unacceptably high volumes of blood from flowing past the distal flow port (203) and entering the right heart chambers.

For the purpose of further illustrating the use of venous catheter (200) in a minimally invasive cardiac bypass system, FIG. 9 further shows cardiopulmonary bypass pump (250) schematically coupled to arterial catheter (260) via an outlet port (not shown) on the pump. Arterial catheter (260) is generally adapted to isolate the left heart chambers from systemic arterial circulation while perfusing oxygenated blood from the cardiopulmonary bypass pump (250) into that circulation. Furthermore, arterial catheter (260) may comprise one of several conventionally known catheters for this purpose, or may include one of the several arterial catheter embodiments previously described above. In addition, FIG. 9 also schematically shows the proximal end portion of venous catheter (200) as it is proximally coupled to an external valve actuator (240). External valve actuator (240) is adapted to adjust the external valves along the distal end portion of the catheter between their relative open and closed positions. External valve actuator (240) may be specifically adapted as one pressurizeable fluid source adapted to switch actuation between the external valves, in the case of expandable balloon variations provided at the external valves, or alternatively as two such fluid sources, as has been previously described above for adjusting multiple balloons as internal valves.

The present invention according to the FIG. 9 variation further contemplates other designs for external valves along the venous catheter body which are adapted to substantially isolate the right heart chambers from vena caval blood flow without circumferentially engaging the interior wall of the vena cavae. For example, in one further vena caval example (not shown), regions along the distal end portion of the elongate body for the venous catheter may include suction ports which are adapted to provide sufficient negative pressure adjacent to the vena caval wall that the wall collapses down around the elongate body at that region. This "suction region" may have a larger outer diameter than the other portions of the venous catheter in order to minimize the extent to which the vena caval wall must collapse. Furthermore, such a "suction region" may also be expandable to an expanded outer diameter which approaches the inner diameter of the vena caval wall, although falling short of actually engaging the wall. Upon collapsing the vena caval wall onto the body surface adjacent to the ports along the suction region, the expandable section may remain at the expanded outer diameter, or may alternatively be reduced in its outer diameter, bringing the vena caval wall further downward to a reduced diameter.

The endolumenal venous isolation catheter (200') shown in FIG. 9B includes distal and proximal external valves (220', 230') which are adjustable relative to each other's position along catheter (200'). In particular, distal external valve (220) is provided on inner member (201') whereas proximal external valve (230) is provided on outer member (201") that is slideably disposed over internal member (201'). By providing indicia of the relative positions of distal and proximal external valves (220', 230'), their spacing may be adjusted to match a particular patient's anatomy. In particular, a physician may adjust this spacing based upon the observed anatomy at the interface between the vena cavae and the right atrium, such as for example according to an X-ray, magnetic resonance, ultrasonic or optical views of this area. According to this adjustable valve variation, blood may be aspirated from the superior and inferior vena cavae through ports (203', 205'), respectively, and transported into a cardiopulmonary bypass system via separate aspiration lumens (not shown) provided along inner and outer members (201', 201"), also respectively. Exterior valves (220', 230') may be adapted to substantially occlude the great veins without expanding and engaging the wall of the veins, as previously described above, in which case an intermediate port may also be provided for venous blood aspiration between the external valves, as shown at (207'). However, it is also further contemplated that such valves may be expandable members such as balloons which actually engage the walls of the great veins during use, as shown in FIG. 9B.

Another alternative venous catheter variation to that shown in FIG. 9 is shown in FIGS. 10A–D, wherein venous catheter (250) is shown in various modes of operation as it is adapted to isolate a right ventricle from vena caval flow without engaging the interior walls of the vena cavae.

Figure 10A:
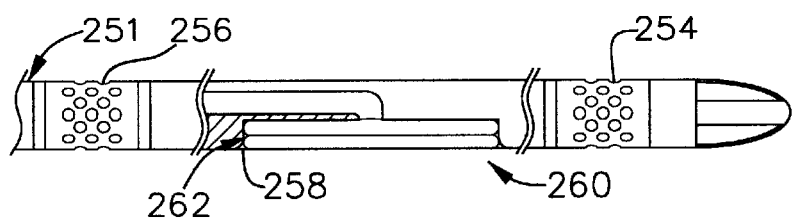
FIG. 10A shows a perspective view of another endolumenal venous isolation catheter for use in isolating a right ventricle from the vena cavae, and shows a longitudinally cross sectioned side view through the catheter in the region of an external valve.

As shown in FIG. 10A, venous catheter (250) includes an external valve (260) along the distal end portion of elongate body (251) between distal and proximal flow ports (254, 256). External valve (260) includes a valve member (262) which is positioned at a discrete location around the circumference of elongate body (251) and is shown in FIG. 10A in a first radial position which characterizes the open position for external valve (260). In the particular variation shown, valve member (262) in the first radial position is housed within a recess (258) provided at the discrete location along the elongate body's circumference. In this open position, external valve (260) is therefore adapted to facilitate percutaneous transluminal delivery of the distal end portion of elongate body (251) into the region of the vena cavae adjacent to the sinus venarum, and is further adapted to allow for venous flow to perfuse around the elongate body's distal end portion and into the right heart chambers.

Figure 10B:
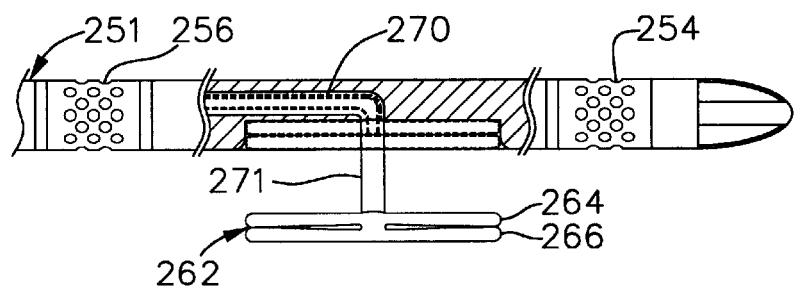
FIG. 10B shows a similar view of the venous catheter shown in FIG. 10A, although showing the valve member of the external valve after being actuated from a first radial position to a radially displaced position which is adjacent to the elongate body.

Distal and intermediate flow ports (254, 256) are coupled to at least one internal flow lumen which extends through the catheter and terminates proximally in a proximal flow port which couples to an inlet port of a cardiopulmonary bypass pump (not shown). Any one of several variations for coupling these ports to the proximal pump may be suitable, as was previously described by reference to the prior venous catheter shown in FIG. 9. FIG. 10B shows venous catheter (250) in a further operational mode, wherein valve member (262) has been adjusted from the first radial position to a radially displaced position which is adjacent to the outer surface of elongate body (251). When the discrete location of valve member (262) is positioned within the vena cavae and adjacent to the sinus venarum into the right atrium, the radially displaced position for valve member (262) is adapted to place valve member (262) within the right atrium, preferably at or adjacent to the tricuspid valve which separates the right atrium from the right ventricle.

Valve member (262) is further shown in FIGS. 10A–B to include two expandable members (264, 266), which are each adjustable from a radially collapsed condition (shown in FIGS. 10A–B) to a radially expanded condition. Expandable members (264, 266) are further shown in FIG. 10C to be coupled to expandable member actuators (271, 272). In the particular variation shown variously throughout FIGS. 10A–B, expandable members (264, 266) are balloon members which are adjusted to the radially expanded position by pressurizing their inner chamber with fluid. Such balloon construction may be of the relatively compliant type or of the relatively non-compliant type, as have been described previously above. According to the expandable balloon variation, expandable member actuators (271, 272) therefore comprise luminal passageways which are adapted to couple to at least one pressurizeable fluid source (not shown) for inflating the respectively coupled balloon or balloons. It is contemplated that either one such pressurizeable fluid source may be coupled to both expandable members (264, 266), or separate such sources may be provided for individually actuating each expandable member (264, 266), respectively.

Figure 10C:
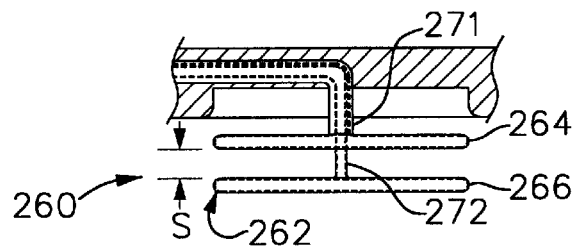
FIG. 10C shows a longitudinally cross-sectioned side view of the external valve shown in FIGS. 10A–B, although further showing two expandable members of the valve member which are separated by a space.

FIG. 10C further shows expandable members (264, 266) separated by a space S. This separation may be a fixed relationship between the members, or may be adjustable. One variation of the latter adjustable arrangement is shown in FIG. 10C, wherein expandable members (264, 266) are independently adjustable and movable relative to the other by manipulating the respectively coupled expandable valve actuator. One suitable construction for this adjustable separation variation for the expandable members may provide a groove through or around expandable member (264) so that expandable member actuator (272) may slideably extend through the groove to adjust the positioning of the more distally disposed expandable member (266). In another construction, expandable member actuator (272) may be coaxially disposed within expandable member actuator (271) and also within and through expandable member (264).

In one more particular variation of this latter construction (not shown), expandable member actuator (271) is preferably constructed of an inner member coaxially disposed within and extending distally beyond an outer member. Expandable member (264) is sealed at its proximal end upon the outer member and at its distal end upon the inner member. The coaxial space between the inner and outer member provides the inflation lumen for expanding expandable member, whereas the inner lumen formed by the inner member forms an inner conduit through which expandable member actuator (272) may slideably extend through and distally beyond for coupling to expandable member (266).

Figure 10D:
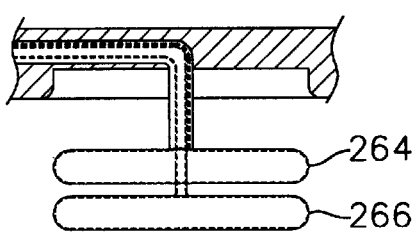
FIG. 10D shows a similar longitudinally cross-sectioned side view of the external valve shown in FIG. 10C, although showing each of the two expandable members further adjusted to a radially expanded condition.

The distal end portions of expandable member actuators (271, 272) must advance along and bend through a substantial angle while adjusting the valve member (262) from the first radial position shown in FIG. 10A to the radially displaced position shown in FIGS. 10B–D. Therefore, these actuators are preferably highly flexible, and comprise for example highly flexible polymeric tubing for the expandable member balloon variation shown. Examples of acceptable materials for constructing these actuator tubings include for example: low modulus polyurethane, PEBAX, low or linear low density polyethylene, nylon, and polyvinyl chloride. In order to achieve the requisite pushability and remote maneuverability of the distal end portions, however, the proximal end portions of expandable member actuators (271, 272) (not shown) may be preferably constructed of stiffer materials, such as for example high density polyethylene, high modulus polyurethane, polyester terepthalate, polyimide, or metal hypotube materials, in order to allow for distal advancement of those members through elongate body (250) such that expandable members (264, 266) for valve member (262) may be adjusted to the relatively displaced positions described.

FIG. 10D shows expandable members (264, 266) during still a further mode of operating venous catheter (250) and after being adjusted from the radially collapsed condition shown in FIGS. 10A–C to a radially expanded condition. This radially expanded condition of expandable members (264, 266) substantially reduces or closes the space S between those members (shown in FIG. 10C), and is adapted to engage the tricuspid valve when positioned within that space prior to expanding the expandable members.

Therefore, according to the progressive modes of operation shown for particular venous catheter (250) in FIGS. 10A–D, the closed position for the external valve (260) is characterized by: (1) aligning the discrete location of valve member (262), while in the first radial position within recess (258), with the sinus venarum in the right atrium; (2) adjusting valve member (262) from the first radial position to the radially displaced position adjacent to elongate body (251) and at least in part within the right atrium and adjacent to the tricuspid valve between the right atrium and the right ventricle; and (3) adjusting at least a portion of the valve member (262) from a radially collapsed condition to a radially expanded condition which engages the tricuspid valve and substantially isolates the right ventricle from the vena cava.

It is further contemplated that other venous catheter variations than those just shown and described by reference to FIGS. 9–9D may suitably function as the venous catheter which is broadly adapted to: (a) substantially isolate the right ventricle from the venous blood flow; and (b) substantially aspirate the vena caval blood into a cardiopulmonary bypass pump; and wherein both the isolation and the aspiration functions are performed without circumferentially engaging the interior wall of the vena cavae.

For example, in a further variation (not shown) of the external valve shown variously throughout FIGS. 10A–D, the valve member in the radially displaced position expands within the right atrium and fills that atrium to such an extent that either no blood or a negligible volume of venous blood is allowed to flow between the vena cavae and the right ventricle. In a further variation of the discretely located and radially displaced valve member, the valve member in the radially expanded condition circumferentially engages a circumferential path of atrial wall tissue which defines that atrium, thereby transecting the atrium such that the sinus venarum is isolated from the right ventricle by the expanded valve member. In still a further variation, the two expandable members are substantially provided as previously shown and described by reference to FIGS. 10A–D, although are modified to instead engage the internal valve and thereby isolate the right ventricle simply by adjusting the individual members toward each other—in other words, the expandability of the expandable members may not be completely required.

Minimally Invasive Bypass Catheter System

FIGS. 11–13 show one minimally invasive cardiac bypass system which includes one combination of particular arterial and venous catheter embodiments previously described above for the purpose of further illustrating the sequential modes of use of a combination assembly in performing a minimally invasive cardiac bypass procedure. For example, venous catheter (320) shown throughout FIGS. 11–13 is constructed according to the particular embodiment previously shown and described by reference to FIGS. 10A–D. However, other venous catheter embodiments such as that previously described by reference to FIG. 9 may be alternatively suitable for use in the overall assembly shown in FIGS. 11–13.

FIGS. 11–13 further show highly schematic representations for the aortic artery, superior and inferior vena cavae, and heart within which the catheters of the overall assembly are shown in various operable modes. For example, there is no particular depiction of the left or right atria or ventricle, although the salient structures regarding the operable catheter modes shown are provided schematically, including the sinus venarum and tricuspid valve in the right heart and the aortic valve in the left heart.

More specifically, FIG. 11 shows the arterial and venous catheters (301, 320) which make-up minimally invasive cardiac bypass catheter system (300) during placement within their respectively desired target vessels. Such percutaneous transluminal catheter placement may be performed in-part according to the standard "Seldinger" technique or according to a direct "cutdown" method including an arteriotomy, as would be apparent to one of ordinary skill. For the purpose of further illustration, however, the general access method according to the "Seldinger" technique is performed as follows.

First, a puncture is first made in the desired vessel for introducing the subject catheter. Such an introduction site for the arterial catheter may be for example in a femoral or a subclavian artery, although preferably in the femoral artery, and for the venous catheter may be for example in a femoral or jugular vein, although preferably in a femoral vein. A guidewire is then advanced through the bore of the needle, after which the needle is withdrawn and a dilator is advanced coaxially over the guidewire. By advancing a tapered distal end of the dilator through the puncture site, that wound is dilated open by the taper until reaching a desired predetermined diameter. An introducer sheath with a hemostatic valve is then advanced either over the dilator or the guidewire or both, after which either the dilator or the guidewire or both are removed from the introducer. The subject device is then advanced into the relative vessel coaxially through the introducer sheath and hemostatic valve.

Each of the venous and arterial catheters is also adapted to track over a steerable, radiopaque guidewire which is adapted to steer and select desired branched vessels under X-Ray visualization in percutaneous transluminal procedures. Therefore, FIG. 11 shows arterial catheter (301) and venous catheter (320) while tracking over guidewires (310, 315), respectively, and into the aortic arch and the region of the vena cavae adjacent to the sinus venarum of the right heart, also respectively. Each of guidewires (310, 315) may be coaxially positioned within the internal flow lumen and through the proximal and distal flow ports of the respectively engaged catheter. Alternatively, each of these guidewires may be slideably engaged within a common internal flow lumen which extends between and fluidly couples with a distal and intermediate flow port along the distal end portion of the respective catheter, such as for example in "rapid-exchange" or "monorail" catheter designs which are previously disclosed for use in angioplasty catheters. In still another alternative variation, the guidewires may be slideably disposed within separate guidewire tracking members extending throughout the respective arterial and venous catheters. Regardless of the particular catheter coupling, however, any one of several known guidewire designs may be suitable for use in positioning the catheters herein described, as would be apparent to one of ordinary skill.

Further to the positioning mode of operation shown in FIG. 11, both external shunt valve (303) and external valve (330) are shown in their respectively closed positions which allow for the arterial or venous blood to flow around the distal end portion of the respective arterial and venous catheters (301, 320) and which also allow for the percutaneous transluminal placement according to this mode. Further to the placement of arterial catheter (301), the distal end portion of elongate body (301) is placed within the aortic arch such that external shunt valve (303) is positioned between the aortic root and the carotid arteries. The distal end portion of elongate body (322) for venous catheter (320) is positioned such that distal flow port (324) and intermediate flow port (326) are positioned within the superior and inferior vena cavae, respectively, and such that valve member (332) for external valve (330) is aligned with the sinus venarum in the right atrium.

In order to facilitate accurate positioning as just described for the relative components along the distal end portions of the arterial and venous catheters, radiopaque markers may be provided at or adjacent to these catheter structures in order to use X-ray or fluoroscopic visualization when guiding the catheters into place. In the alternative or in addition to such radiopaque markers, markers or other indicia may also be provided on the proximal end portions of these catheters such that the catheters in vivo position is determinable when the catheter is observed to advance a predetermined distance beyond an introducer sheath or guiding catheter according to the positioning of such proximal indicia relative to the introducer or guiding catheter. Moreover, other positioning means may be used in order to accurately place the relative valves and flow ports of the arterial and venous catheters. For example, ultrasound visualization may be used to aid in accurate placement of these structures. In one ultrasound variation, an ultrasonic probe may be used externally of one or both of these catheters, either along side and adjacent to the catheter or even further removed location such as in the esophagus in a transesophageal approach. Still further, direct fiber optic imaging may be employed for visualizing the position of the respective catheter structures in relation to the particular anatomical structures of interest.

FIG. 12 shows a further mode of operation for each of arterial and venous catheters (301, 320) during use within minimally invasive cardiac bypass system (300).

More specifically to arterial catheter (301) as shown in FIG. 12, exterior shunt valve (303) is shown in a radially expanded condition which characterizes a shunting position for that valve within the aortic arch. Exterior shunt valve (303) in the shunting position forms anchor (304), which circumferentially engages the interior surface of the aortic wall, and also forms funnel (305) which directs antegrade aortic blood flow into distal flow port (306), proximally through an internal flow lumen (not shown) and out an intermediate flow port (307) which is located along elongate body (302) proximally of external shunt valve (303). In this operable mode, arterial catheter (301) is thus adapted to secure the distal end portion of elongate body (302) into position while allowing the heart to continue beating and perfusing the systemic arterial circulation proximally of anchor (304). This shunted antegrade flow may be further facilitated by adjusting a distal internal valve (not shown) within the flow lumen distally to intermediate flow port (307) and a proximal internal valve (not shown) within the flow lumen proximally of intermediate flow port (307) to open and closed positions, respectively, as has been previously described above by reference to the particular arterial catheter embodiments.

Further to the operable mode of arterial catheter (301) shown in FIG. 12, a distal cannula member is shown extending from elongate body (302) distally from external shunt valve (303) and distal flow port (307), and includes cannula delivery port (308) and ventricular venting port (309). Cannula delivery port (308) is positioned within the aortic root in the region of the sinus of valsalva and is fluidly coupled to a pressurizeable cardioplegia agent source (not shown) via a cardioplegia delivery lumen (also not shown), such as has been described previously above. Ventricular venting port (309) is positioned through the aortic valve and into the left ventricle where it is adapted to aspirate residual blood from that ventricle during the cardiac bypass procedure.

Specifically regarding venous catheter (320) as shown in FIG. 12, valve member (332) is shown adjusted to a radially displaced position adjacent to the elongate body (322) and within the right heart chambers. In more detail, two expandable members (334, 336) which comprise at least in part valve member (332) are separated by a space which houses the tricuspid valve located between the right atrium and ventricle.

FIG. 13 shows still a further operable mode for each of the arterial and venous catheters (301, 320) as they are used to bypass the heart subsequent to temporarily arresting the heart according to the overall assembly herein described.

Arterial catheter (301) is shown in an operable mode where it is adapted to isolate the heart from systemic arterial circulation and provide artificial flow of oxygenated blood into the systemic circulation from the cardiopulmonary bypass pump (not shown). According to this mode, cardioplegia agent is delivered into the coronary arteries via cardioplegia delivery port (308) and the heart is thereby temporarily arrested. With external shunt valve (303) still anchored in the aortic arch in the shunting position, the internal lumen is selectively occluded with a distal internal valve (not shown) located within the lumen between the distal and intermediate flow ports (306, 307) according to the operable mode shown in FIG. 13. Thus, the left heart chambers are isolated from systemic arterial circulation proximally of external shunt valve (303) and the distal internal valve within the internal flow lumen. Arrows exiting intermediate flow port (307) are thus used in FIG. 13 to depict the artificial flow of oxygenated blood distally through the internal flow lumen from a cardiopulmonary bypass pump.

Venous catheter (320) is shown in FIG. 13 in an operable mode which is adapted to substantially isolate the right heart chambers from the vena cavae and also to aspirate the venous blood in the vena cavae into the inlet port of the cardiopulmonary bypass pump. According to this mode, the two expandable members (334, 336) are shown adjusted to a radially expanded condition which narrows the space of separation therebetween and engages the tricuspid valve, thereby isolating the right ventricle from the right atrium and vena cavae. Arrows show venous blood as it is aspirated into the at least one internal flow lumen of the venous catheter and into a cardiopulmonary bypass pump (not shown).

Endolumenal Proximal Anastomosis Isolation Assembly

Figure 14A:
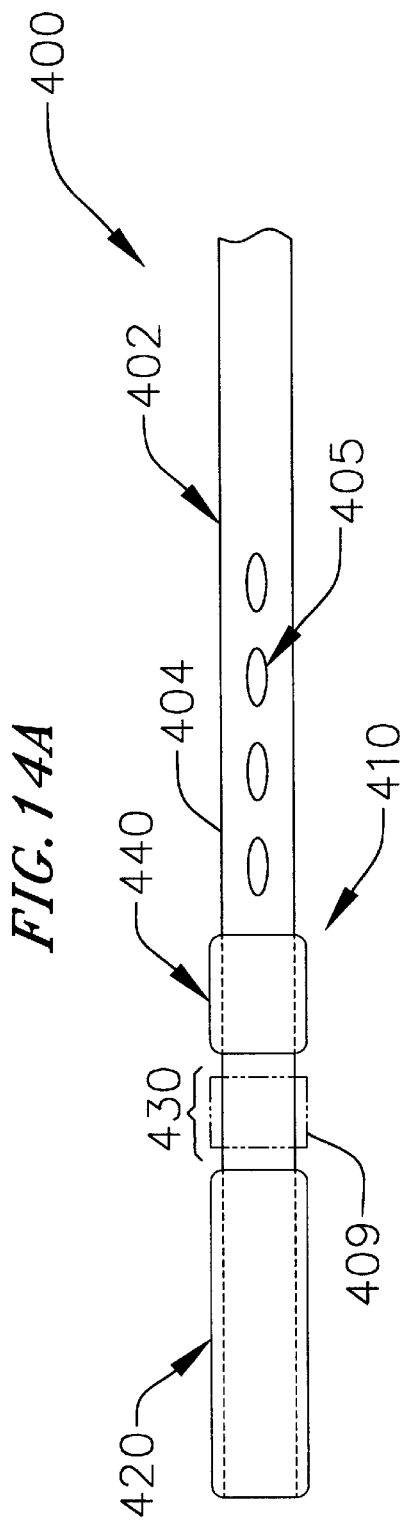
FIG. 14A shows a perspective view of the distal end portion of another endolumenal aortic isolation catheter adapted for use in a "beating heart" aortic isolation procedure.

FIGS. 14A–23B variously show an endolumenal proximal anastomosis isolation assembly which is adapted to endolumenally isolate a proximal anastomosis site from a pressurized aortic blood field. As will be described in more detail below, by use of this assembly a proximal anastomosis may be formed between a bypass graft and the aorta during a beating heart CABG procedure without significant loss of blood at the proximal anastomosis site. By general reference to FIGS. 14A–B, and FIGS. 22A–B, arterial catheter (400) is shown to include an elongate body (402) with an aortic isolation assembly (410) along its distal end portion (404). Aortic isolation assembly (410) includes distal and proximal balloons (420, 440) which are spaced along the longitudinal axis of the elongate body by an isolation region (430). Distal and proximal balloons (420, 440) are shown in FIG. 14A in first and second radially collapsed positions, wherein these balloons have outer diameters that are adapted to facilitate delivery of arterial catheter (400) into the aorta (470).

Figure 14B:
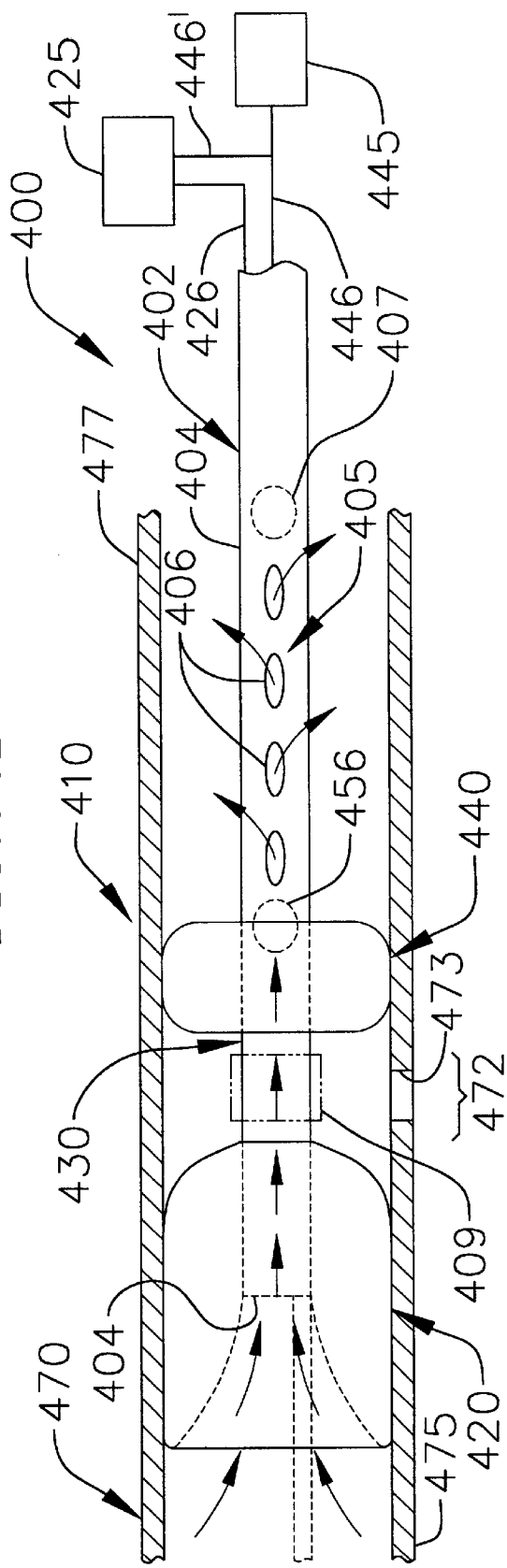
FIG. 14B shows a perspective view of the endolumenal aortic isolation catheter shown in FIG. 14A, except showing the catheter during a mode of use for isolating a proximal anastomosis site along an aorta, and schematically showing an expansion actuator assembly as a part of an overall medical device system.

With isolation region (430) positioned along anastomosis site (472), as shown in FIGS. 14B and 22B, distal and proximal balloons (420, 440) are adjustable to first and second radially expanded positions, respectively, which are shown to have expanded outer diameters which are sufficient to engage upstream portion (475) and downstream portion (477), also respectively, of aorta (470). As further shown in FIGS. 14B and 22B, elongate body (402) further includes a flow lumen (shown schematically by way of flow arrows) which extends at least in part between a distal port (404) and a proximal port (405) which is further shown as a plurality of apertures (406). Distal port (404) is provided along the distal end portion (403) of elongate body (402) distally of distal balloon (420), whereas proximal port (405) is provided along distal end portion (403) proximally of proximal balloon (440).

According to this construction for catheter (400) and the deployed configuration shown in FIG. 14B and FIG. 22B, proximal anastomosis site (472) and isolation region (430) are substantially isolated from pressurized aortic blood in upstream and downstream regions (475, 477) by means of radially expanded distal and proximal balloons (420, 440). With this isolation established, aperture (473) is also shown after being formed along the proximal anastomosis site (472). By further reference to the positioning of distal and proximal ports (404, 405) relative to distal and proximal balloons (420, 440), respectively, the pressurized aortic blood is also shown schematically by way of flow arrows as it is shunted from the upstream region (475), into the flow lumen through distal port (404), proximally along the flow lumen, out from the flow lumen through proximal port (405), and into downstream region (477).

Accordingly, a proximal anastomosis may thus be formed at aperture (473) during a beating heart CABG procedure without substantial loss of blood and without externally clamping the aorta. In addition, it is believed that the expandable balloons (420, 440) which provide the isolation along the anastomosis site furthermore provide a benefit in substantially "stenting" the aorta into a distended, substantially physiologic shape while the proximal anastomosis is being formed.

FIGS. 15A–B and 23A–B, show another arterial catheter (450) which is adapted to isolate a proximal anastomosis site (472) during a beating heart procedure, and illustrates another specific design for aorta isolation assembly (460). By contrast to the assembly shown in FIGS. 14A–B and 22A–B, arterial catheter (450) shown in FIGS. 15A–B and 23A–B includes an aorta isolation assembly that includes only one balloon (461) having a shape when expanded that forms distinct distal and proximal regions (463, 469) which are separated by intermediate region (465) that is located along isolation region (462). More specifically, similar to distal and proximal balloons (420, 440) shown in FIGS. 14A–B and 22A–B, distal and proximal regions (463, 469) of balloon (460) are expandable to radially expanded positions having first and second expanded outer diameters that are sufficient to engage upstream and downstream regions (475, 477) of aorta (470), respectively. Intermediate region (465) is shown also expanded when the balloon is in the radially expanded condition, except only to an outer diameter which is substantially less than the outer diameters of the distal and proximal regions (463, 469) engaged to aorta (470) and insufficient to engage aorta (470) along the proximal anastomosis site (472). Accordingly, a similar isolation of proximal anastomosis site (472) is achieved with the FIG. 15B and FIG. 23B assembly as that shown in FIGS. 14B and 22B. Moreover, the limited range of expansion along intermediate region (465) of balloon (460) relative to proximal and distal regions (463, 469) allow aperture (473) to be punched at the isolated anastomosis site (472) and a graft to be sutured, stapled, or otherwise anastomosed there without compromising the inflated balloon (460).

FIGS. 14B and 15B also show in shadow view distal internal valves (406, 456), respectively, and proximal internal valves (407, 457), also respectively, in order to illustrate that the internal flow lumen of the assemblies in those Figures may be constructed to incorporate the various novel aspects of the cardiac bypass embodiments previously described above by reference to FIGS. 1A–8D and 11–13. For example, either of aorta isolation assemblies (410, 460) may also be used as shunt valves in a stopped-heart cardiac bypass procedure as previously described above merely by closing the flow lumens in the respective catheters with either of distal internal valves (406, 456), respectively. Moreover, the distal balloons shown for assemblies (410, 460) include funneled distal shapes in a similar construction to the various embodiments provided above for the shunting cardiac bypass aspect of the invention, thereby enhancing the fluid dynamics of pressurized blood flowing from the aortic root as it is shunted into the internal catheter flow lumen. Accordingly, this combination construction provides one catheter which may provide endolumenal proximal anastomosis isolation in either a beating heart or a stopped heart procedure.

Figure 23A:
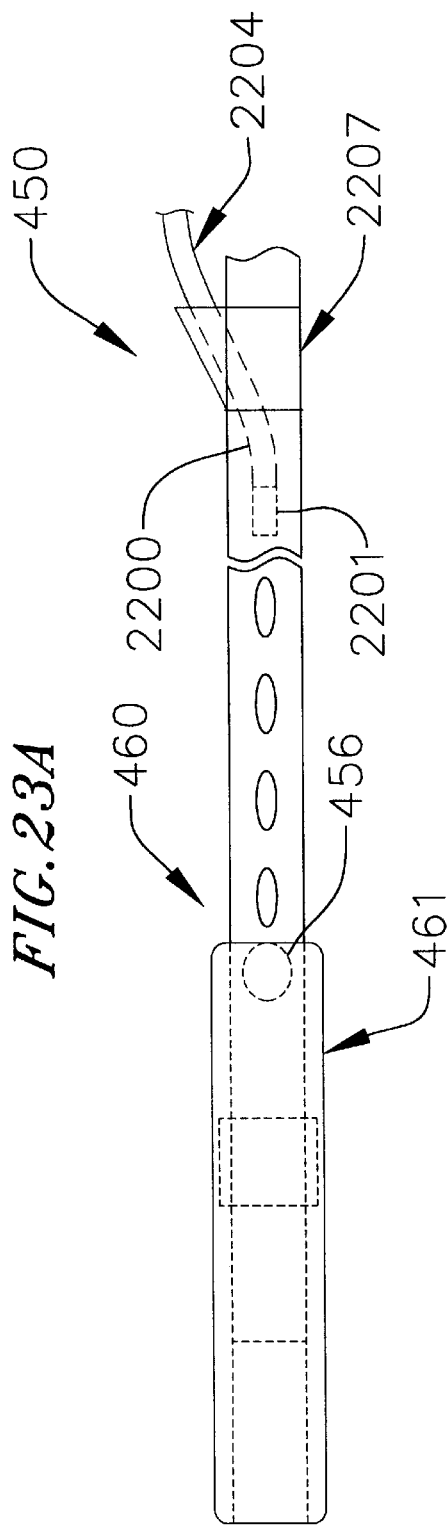
FIG. 23A shows a perspective view of the distal end portion of another endolumenal aortic isolation catheter adapted for use in a "beating heart" endolumenal aortic isolation procedure.
Figure 23B:
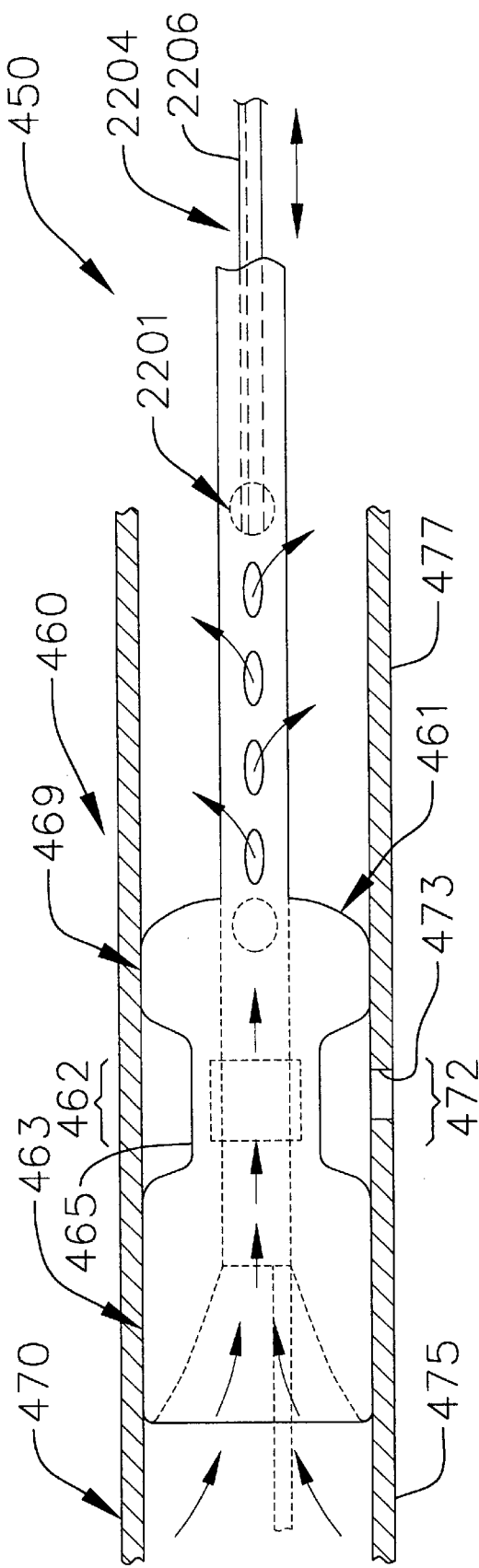
FIG. 23B shows a perspective view of the endolumenal aortic isolation catheter shown in FIG. 15A, except showing the catheter during one mode of use when isolating a proximal anastomosis site along an aorta.

By referring to FIGS. 22A–23B another embodiment can be seen that utilizes a movable internal valve member (2200) to control antegrade and retrograde blood flow in the internal lumen of elongate body (402). The movable internal valve member may consist of an expandable region (2201) positioned at or near the distal tip (2203) of cannula (2204). As can be seen in FIGS. 22B and 23B, cannula (2204) is movable within the flow lumen and can be selectively positioned to permit endolumenal proximal anastomosis isolation in either a beating heart or stopped heart procedure. The cannula (2204) can be advanced or retracted within the flow lumen to position expandable region (2201) proximally of apertures 406 to permit antegrade flow from a beating heart; or positioned distally of aperatures 406 to permit flow from the by-pass pump when the heart is stopped. The expandable region (2201) of cannula (2204) may be an inflatable balloon (2201') which is expandable by a fluid delivered through a delivery lumen (2206) contained within cannula (2204).

Although the expandable region as above described may be inflated by a fluid to occlude the flow lumen, the expandable region may also be expanded by a construction that includes an enclosed volume having a fixed mass of fluid whose shape may be varied mechanically to extend the shape radially against the flow lumen wall so as to occlude the flow lumen. Such a mechanical system would eliminate the need for a delivery lumen to deliver fluid under pressure in order to inflate a balloon.

As can be seen in FIGS. 22A and 23B, the cannula may be externally introduced into the flow lumen through a sealed connector (2207). Visualization of the expandable region (2201) for positioning it within the flow lumen may be accomplished by radiopaque and visible x-ray fluoroscopy or the expandable region may be visualized by the use of ultra sound or other techniques well-known in the prior art.

One specific construction which is believed to be sufficient for forming a balloon such as balloon (460) just described by reference to FIGS. 15A–B is shown in FIG. 16. More specifically, FIG. 16 shows intermediate region (485) of balloon (480) to have a different material construction than distal and proximal regions (483, 489) of balloon (480). In one aspect of this assembly, the intermediate region (485) may be constructed to be less compliant than the distal and proximal regions (483, 489), thereby yielding the expansion characteristic with varying outer diameters as shown. In one specific aspect of this varied compliance, a series of different tubings constructed of different materials may be spliced together to form balloon (480). Or, balloon (480) may be constructed at first of one continuous material along these regions which is modified along the intermediate region (485) to yield the variable compliance along the balloon. In one aspect of such a construction, the balloon wall may be thicker along the intermediate region (485) than at distal and proximal regions (483, 489). Also, the balloon material along either the intermediate region (485) or the distal and proximal portions (483, 489) may be specially treated apart from the other regions, such as by radiation or chemical treatment, such that the material essentially changes its expansion characteristics. Furthermore, a composite construction may be provided along the balloon (480), such as for example by using reinforcement fibers similar to the construction previously shown and described by reference to FIGS. 7A–C, though modified in order to yield the shapes shown in FIGS. 16 and 15B. The fiber component according to the specific fiber-reinforced composite construction just described for balloon (480) in FIG. 16 may be considered more broadly as an expansion limiter provided along intermediate region (485). FIG. 17 shows another embodiment wherein an expansion limiter (497) is provided along intermediate region (495) of balloon (490), and more specifically shows the expansion limiter (497) as a cuff which is provided over intermediate region (495) of balloon (490). Such a cuff may be an elastic band simply placed over intermediate region (495), or may be a laminate layer secured to intermediate region (495) in order to modify the overall compliance along that portion of the balloon (490). Moreover, such a cuff in any event may be provided externally of intermediate region (495), or in an alternative construction may be laminated onto an inner surface of intermediate region (495).

The particular balloon embodiments shown in FIGS. 14A–23B are specific illustrations of a more general construction contemplated for the aorta isolation assembly herein described. In this regard, the aorta isolation assembly provides distal and proximal portions which are separated by an isolation region. The "inflated" or "expanded" conditions shown for the balloon embodiments in FIGS. 14B, 15B, 22B and 23B may be illustrated more broadly in that the distal and proximal portions of the assembly are adjustable to "extended" positions which are extended from the shaft to engage the aorta. As such, other alternative "expandable" or otherwise "extendible" members may be substituted for these specific balloon embodiments herein specified. In addition, it is also to be appreciated that the distal and proximal "portions" of an aortic isolation assembly such as according to the specific embodiments herein shown and described may be adjusted to their respective extended positions either together or separately. For example, the distal and proximal balloons (420, 440) shown in FIGS. 14B and 22B may be either fluidly coupled to separate pressurizeable fluid sources (425, 445) and thus be inflated separately, or may be coupled to a common pressurizeable fluid source. Such common coupling between pressurizeable fluid source (425) and distal and proximal balloons (420, 440) may be achieved via either one common inflation lumen between the balloons, or by separate lumens coupled to the common inflation source, such as shown schematically at lumens (426, 446'). Similarly, the distal and proximal regions (463, 469) for balloon (460) shown in FIGS. 15B and 23B may also be constructed in such a way as to be effectively expanded "separately", such as by varying the construction between these regions in a similar manner described by reference to the intermediate regions of the embodiments shown in FIGS. 16 and 17.

Also, visualization markers are variously shown throughout FIGS. 14A–17 positioned over a tubular member along the isolation region of the respective aorta isolation assembly, such as for example at visualization marker (409) shown in FIG. 14B. These visualization markers may be radiopaque and visible via X-ray fluoroscopy. Or, the visualization markers may be ultrasonically visible, such as by a construction which is ultrasonically opaque, or by providing an ultrasonic energy source which emits a signal that may located and visualized. Furthermore, a light source may be provided as the visualization marker. In any event, other locations than along the isolation region are contemplated for such markers, so long as the isolation region's location is readily identifiable to a user based upon visualizing the marker. For example, according to the embodiment of FIG. 14B, by removing any radiopaque marker from isolation region (430) and inflating distal and proximal balloons (420, 440) with radiopaque contrast fluid, the balloons may provide sufficient markers in that the relatively non-radiopaque isolation region is known to be located along the space between them.

"Direct-Access" Endolumenal Aortic Isolation System

Figure 18:
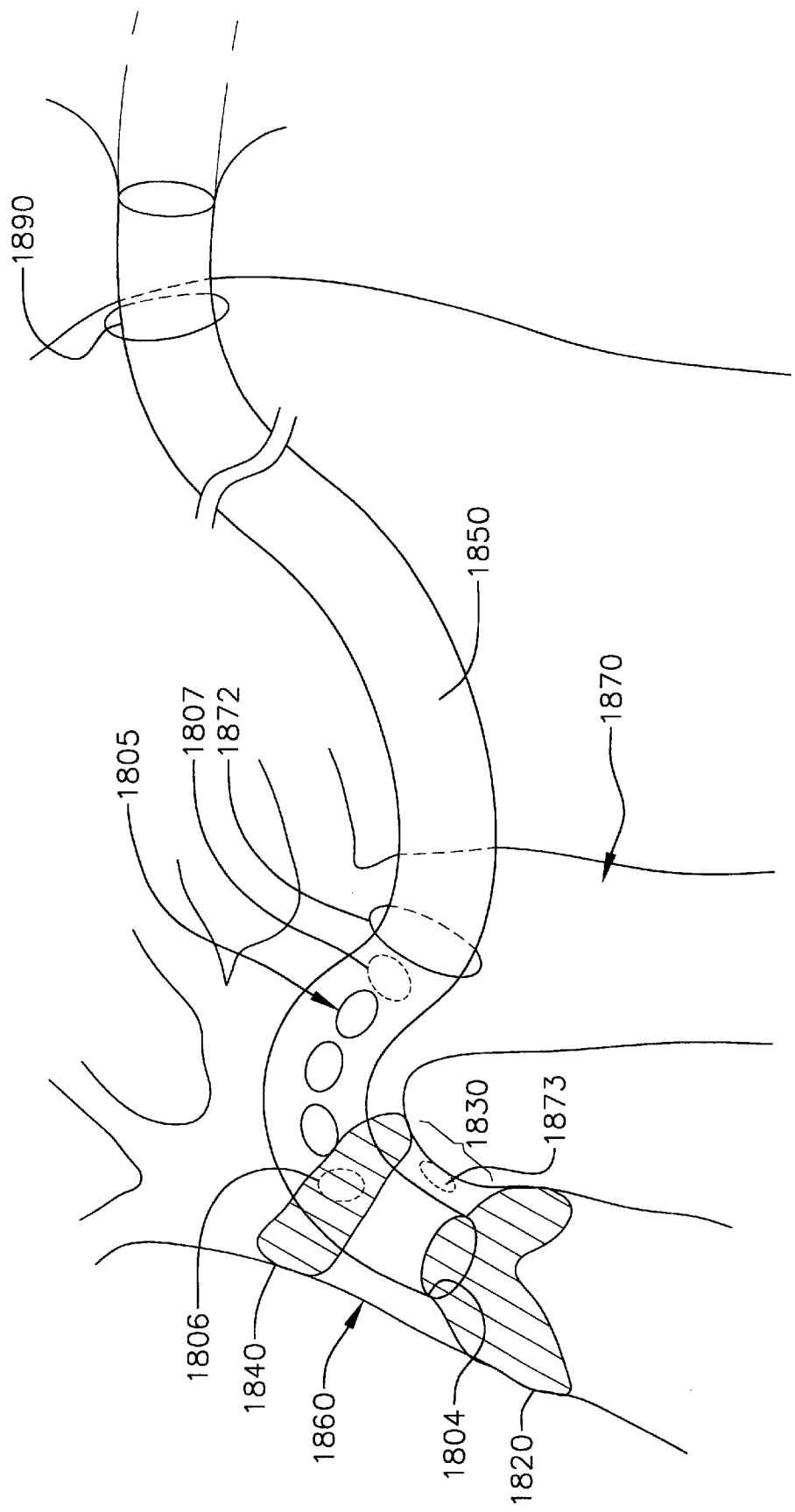
FIG. 18 shows a longitudinal perspective view of an endolumenal aortic isolation catheter with two balloons such as that shown in FIGS. 14A–B, although showing the catheter during one mode of use in a direct access endolumenal aortic isolation procedure.
Figure 21:
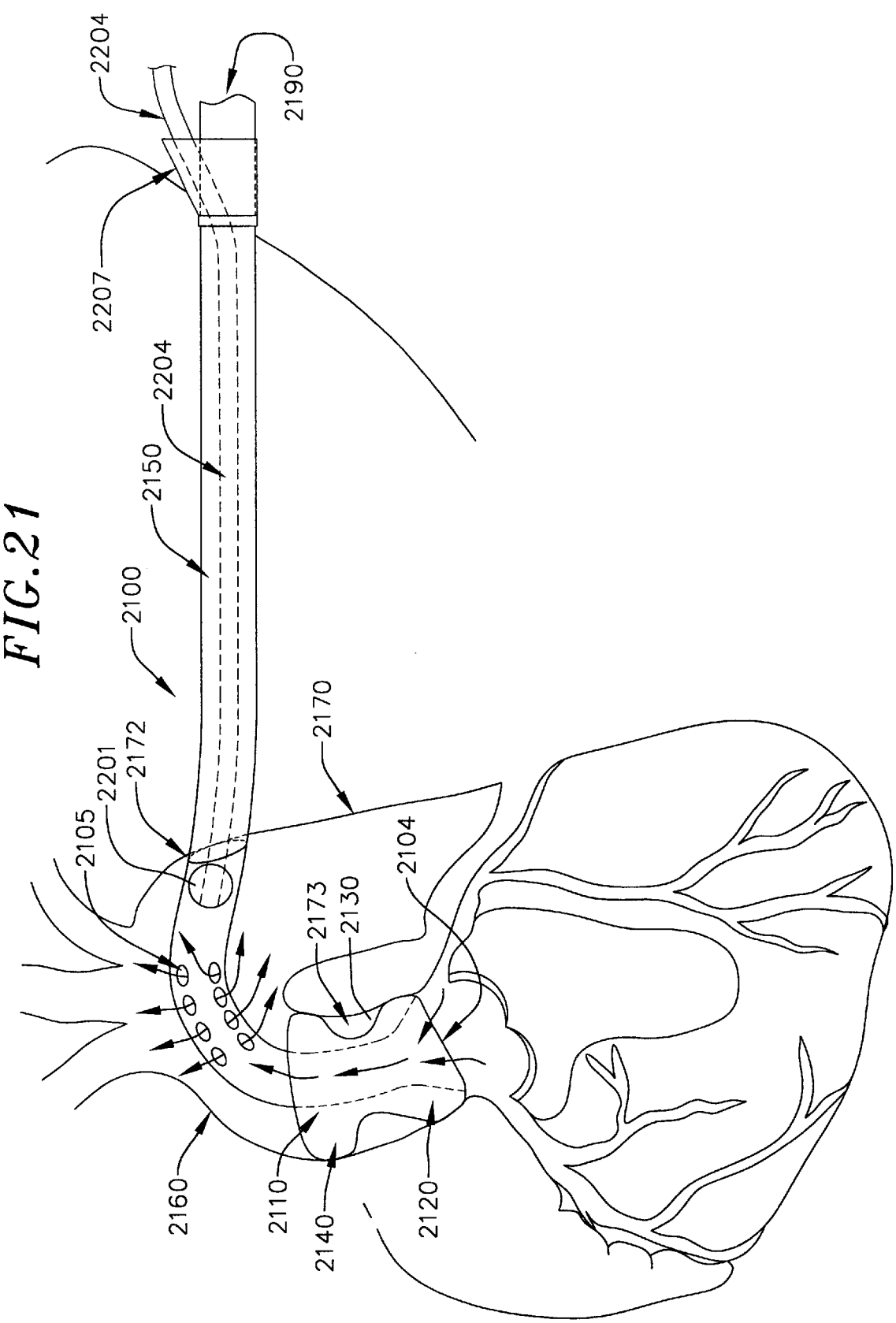
FIG. 21 illustrates a direct access endolumenal aortic isolation catheter having a movable internal valve.

FIGS. 18 and 21 show endolumenal aortic isolation catheter (1800, 2100) during use in a direct access endolumenal aortic isolation procedure according to the invention. More specifically, distal end portion (1804, 2104) is shown extending into aorta (1870, 2170) through an aperture or port (1872, 2172) that is formed along the aortic wall (1860, 2160). External valve assembly (1810, 2110) is shown after being positioned retrogradedly along the aorta and such that intermediate region (1830, 2130) is aligned with a desired intervention site (1873, 2173) between external valve members (1820, 1840) and (2120, 2140) where surgery is to be performed on the aortic wall, such as for example in order to form a proximal anastomosis there in a coronary artery bypass procedure. A lumen (1850, 2150) extends between port (1804, 2104) and port (1890, 2190) and across the external valve assembly (1810, 2110) in order to allow in one mode for a proximal anastomosis procedure to be performed while the heart is still beating and perfusing the systemic arterial circulation downstream of the proximal anastomosis site (1873). As can be seen by comparing FIGS. 18 and 21, the isolation catheter of FIG. 21 differs from the isolation catheter of FIG. 18 in that it utilizes a movable valve (2200) with expandable region (2201) selectively positioned within lumen (1850) by advancing and retracting cannula (2204). Cannula (2204) is shown in detail in FIGS. 22A–23B and described above.

Figure 19A:
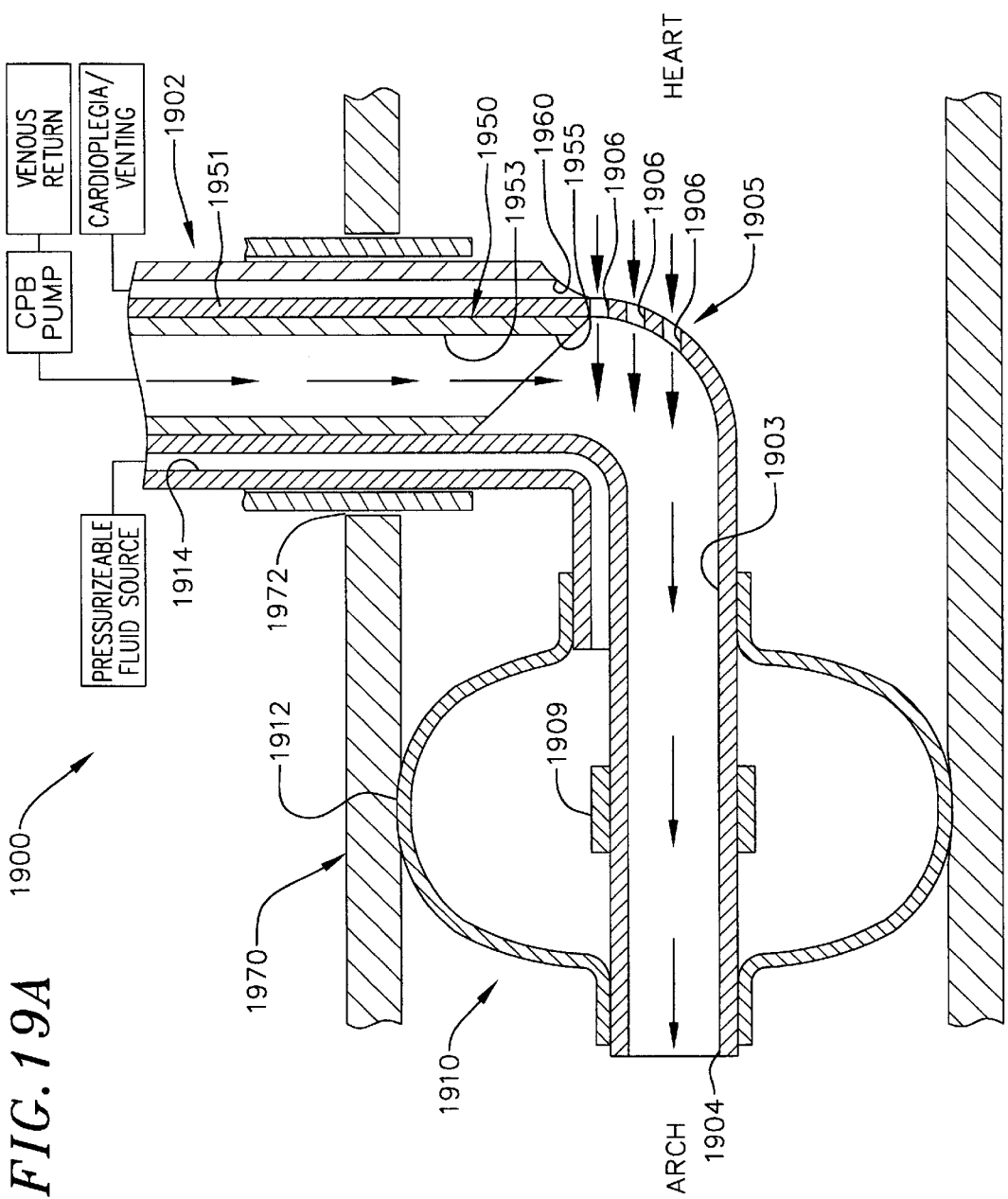
FIG. 19A shows a longitudinally cross-sectioned side view of the distal end portion of a direct access endolumenal aortic isolation catheter during one mode of use which allows the heart to pump blood into the systemic arterial circulation through a distal internal flow lumen provided along the catheter.

Endolumenal aortic isolation catheter (1900) is shown in FIG. 19A after positioning external valve assembly (1910) downstream from aortic introduction site (1972) formed in aorta (1970) and through which distal end portion of catheter (1900) is introduced into the aorta (1970).

External valve assembly (1910) is shown to include an inflatable balloon (1912) that is fluidly coupled along inflation lumen (1914) to inflation source (1914'), though other extendible members otherwise known or herein described may be suitable substitutes. Catheter (1900) also has an internal valve member that includes a wall (1955) that is adjustable from a first position (FIG. 19A) to a second position (FIG. 19B) relative to port (1905). In the specific embodiments shown in FIGS. 19A–D, wall (1955) is provided along the distal end portion of internal valve (1950) that is slideably engaged within passageway (1951) provided along catheter body (1902). According to this embodiment, wall (1955) is adjustable between the first and second positions by adjusting internal valve (1950) along passageway (1951). With external balloon (1912) inflated to engage the interior wall of aorta (1970) and wall (1955) in the first position as shown in FIG. 19A, blood from the heart and aorta upstream of port (1905) is allowed to flow through port (1905) and (1906) through distal internal lumen (1903) and antegradedly across external balloon (1912), and thereafter out into systemic arterial circulation through distal port (1904) as shown in FIG. 19A. By advancing internal valve (1950) along passageway (1951), wall (1955) is adjusted to the second position to obstruct flow through ports (1905) and (1906) and thereby block fluid communication between distal internal flow lumen and the upstream region of the aorta and heart.

Further to the configuration for external valve (1910) and internal valve (1950) as shown by reference to FIG. 19B, the heart and upstream region of the aorta are substantially isolated from the systemic arterial circulation. The patient's systemic arterial circulation may be supported by use of a cardiopulmonary bypass pump which receives venous blood from a venous aspiration catheter and pumps the blood after oxygenation into the systemic arterial circulation through proximate internal flow lumen (1953) and out of distal port (1904).

Further variations of internal valve member (1950) are shown respectively in FIGS. 19C–D. These variations allow for proximate internal flow lumen (1953) to be substantially fluidly isolated from distal internal flow lumen (1903) and therefore also from the cardiopulmonary bypass pump while wall (1955) is in the first position and the heart is perfusing the systemic arterial circulation through ports (1905 and 1906) and distal internal flow lumen (1903). More specifically to the FIG. 19C variation, internal valve member (1950) is expandable into internal flow lumen (1953) in order to selectively open or occlude internal flow lumen (1950). According to one mode of operation with wall (1955) in the first position and the heart perfusing systemic circulation through distal internal flow lumen (1903), expandable member (1955) is adjusted to the closed position to substantially occlude fluid communication from proximate internal flow lumen (1953). In another mode wherein wall (1955) is adjusted to the second position and the upstream aortic regions and heart are isolated from systemic arterial circulation, expandable member (1955) is adjusted to the open position such that proximal internal flow lumen (1953) fluidly communicates with distal internal flow lumen (1903) and systemic arterial circulation may be thereby perfused by use of the by-pass pump. More detail of the specific embodiment of the internal valve member (1950) shown in FIG. 19C is shown in FIG. 19D. More specifically, internal valve member (1955) includes a wall (1957) that borders passageway (1951) that extends along internal valve member (1950) and fluidly couples wall (1955) to a pressurizeable fluid source (not shown). By pressurizing passageway (1960), wall (1955) deflects into proximal internal flow lumen (1953) to substantially occlude flow therethrough. By conversely withdrawing fluid from passageway (1960) and pulling a vacuum, wall (1955) is positioned in an open position such that internal flow lumen (1953) is open to flow.

FIG. 20 shows a similar view of another direct access endolumenal aortic isolation system of the invention as that shown for the system of FIG. 19A, although showing an external balloon valve having an intermediate region with a restricted outer diameter to allow for a surgical procedure to be performed on the arterial wall along that region. The structural features of the various individual catheter embodiments described above should not be limited to use in minimally invasive cardiac bypass assemblies or procedures, and may be adapted according to one of ordinary skill for other medical applications without departing from the scope of the present invention. In particular, systems which utilize one or several of the arterial and venous embodiments described above may be used in either open heart applications, wherein a surgeon uses the catheters provided for isolating the heart but nevertheless performs a sternotomy for direct surgical access to the heart, "port-access" types of procedures, or even still more minimally invasive procedures wherein the heart is isolated by use of the catheters of the present invention and further medical treatment is also performed via percutaneous transluminal assemblies and methods.

In a further example, an external shunt valve which forms an anchor and a funnel for directing flow through an internal catheter lumen, although specifically provided above in catheter embodiments which are adapted for shunting antegrade aortic blood flow into the systemic arterial circulation, may also be modified for applications within other lumens or body spaces and still fall within the scope of the present invention. Furthermore, other catheter applications than those described above for use in an aorta may include the internal valve embodiments herein described for selectively opening or closing an internal flow lumen and still fall within the scope of the present invention.

In still a further example, catheters which are generally adapted to isolate one body space or lumen from another body space or lumen by adjusting a valve member from a first radial position at a discrete location around the catheter's circumference to a radially displaced position which is adjacent to the elongate body of the catheter are considered within the scope of the present invention, notwithstanding the specific description above which provides such a valve member only on a venous catheter in a minimally invasive cardiac bypass system.

Other modifications or combinations of the specific catheter embodiments described above which may become apparent to one of ordinary skill from this disclosure, but which have not been specifically described herein, are also contemplated as falling within the scope of the present invention. In addition, improvements to the embodiments which are not specifically provided for but which may be apparent to one of ordinary skill based upon this disclosure are also included within the invention, such as for example an improvement providing a heparin coating on an external or internal surface on any one of the arterial or venous catheter embodiments.

What is claimed is:

1. An endolumenal aortic isolation system comprising:
    an elongate body with a proximal end portion, a distal end portion, a longitudinal axis, and a flow lumen which extends between a distal port located along the distal end portion of the elongate body and a proximal port located along the proximal end portion of the elongate body, wherein the flow lumen communicates externally of the elongate body through and intermediate port located between the distal and proximal ports;
    a cannula member, having a distal and proximal end and an axis of elongation, removeably and slidably carried relative to said elongate body so as to permit axial movement of said cannula member within said flow lumen, said cannula member comprising an adjustable valve member carried by said cannula adjacent said distal end where said adjustable valve member is selectively positionable in said flow lumen such that upon adjusting said adjustable valve member to a closed position after said adjustable valve member is positioned between said intermediate port and said proximate ports, said flow lumen is open between said distal and intermediate ports and closed between said intermediate and proximate ports, and when said adjustable valve member is adjusted to a closed position after positioning said adjustable valve member between said distal and intermediate ports said flow lumen is open between said proximate and intermediate ports and closed between said intermediate and distal ports;
    an aorta isolation assembly located along the distal end portion of the elongate body with a distal portion located proximally of the distal port, a proximal portion located proximally of the distal portion and distally of the intermediate port, and an intermediate region located between the distal and proximal portions, the distal and proximal portions being adjustable between first and second collapsed positions, respectively, and first and second extended positions, also respectively, which are each adapted to circumferentially engage an aortic wall of an aorta, wherein in the respective first and second extended positions, the distal and proximal portions have first and second outer diameters and the intermediate region has an intermediate outer diameter that is less than the first and second outer diameters and is insufficient to engage the aortic wall; and,
    wherein the aorta isolation assembly is adapted to isolate a proximal anastomosis site along the aortic wall from a volume of pressurized blood at a location in the aorta either distally from the distal portion or proximally from the proximal portion of the aorta isolation assembly with respect to the elongate body by positioning the intermediate region within the aorta along a proximal anastomosis site and adjusting the distal and proximal portions to the first and second extended position, respectively, to thereby engage the aortic wall on upstream and downstream sides of the proximal anastomosis site.

2. The system of claim 1 wherein said adjustable valve member comprises an inflatable balloon and said cannula member contains a pressure lumen communicating with said inflatable balloon.

3. The system of claim 1 wherein said adjustable valve member comprises:
    (a) a flexible container;
    (b) a mass of fluid captively and sealingly contained within said flexible container having a first shape to permit said flexible container to be advanced or retracted axially within said flow lumen; and
    (c) means carried by said cannula member and associated with said flexible container for radial displacement of said mass of fluid to a second position so as to occlude said flow lumen.

4. The system of claim 1, wherein the distal and proximal portions of the aorta isolation assembly are separately adjustable to the first and second extended positions, respectively.

5. The system of claim 4, wherein the distal and proximal portions are adapted to couple to at least one expansion actuator and are radially expandable to the first and second extended positions, respectively.

6. The system of claim 5, wherein the distal and proximal portions are adapted to couple to first and second expansion actuators, respectively.

7. The system of claim 5, wherein the distal and proximal portions comprise distal and proximal balloons, respectively, that are adapted to fluidly couple to at least one pressurizeable fluid source and to inflate to the first and second extended positions, also respectively.

8. The system of claim 7, wherein the distal and proximal balloons are adapted to fluidly couple separately to first and second pressurizeable fluid sources, respectively.

9. The system of claim 7, wherein the elongate body further comprises a distal inflation lumen fluidly coupled to the distal balloon and a proximal inflation lumen fluidly coupled to the proximal balloon, the distal and proximal inflation lumens being adapted to fluidly couple to said at least one pressurizeable fluid source.

10. The system of claim 7, wherein the distal and proximal inflation lumens are adapted to separately couple to first and second pressurizeable fluid sources, respectively.

11. The system of claim 5, wherein the distal and proximal portions are adapted to couple to a common expansion actuator which is adjustable between first and second actuating conditions, the distal portion being expandable to the first extended position when the common actuator is adjustable to the first actuating condition, and the proximal portion being adjustable to the second extended position when the common actuator is adjusted to the second actuating condition.

12. The system of claim 11, wherein the distal and proximal portions comprise distal and proximal balloons, respectively, which are each adapted to fluidly couple to a common pressurizeable fluid source and are inflatable with fluid from the fluid source to the first and second extended positions, respectively, wherein the distal balloon is inflatable to the first extended position when the fluid is adjusted to a first pressure, and wherein the proximal balloon is inflatable to the second extended position when the fluid is adjusted to a second pressure.

13. The system of claim 12, wherein the distal balloon comprises a first material with a first compliance and the proximal balloon comprises a second material with a second compliance which is different from the first compliance.

14. The system of claim 12, the elongate body further comprises a common lumen which is fluidly coupled to the distal and proximal balloons and which is also adapted to couple to the common pressurizeable source of fluid.

15. The system of claim 1, wherein the distal and proximal portions are adjustable together to the first and second extended positions, respectively.

16. The system of claim 15, wherein the distal and proximal portions are adapted to couple to a common actuator which adjusts the distal and proximal portions together to the first and second extended positions.

17. The system of claim 16, wherein the distal and proximal portions comprise distal and proximal regions, respectively, of a balloon and the intermediate region of the aorta isolation assembly is located between the distal and proximal regions wherein the balloon is adapted to fluidly couple to a pressurizeable fluid source and to inflate with fluid from the fluid source to a radially expanded condition which characterizes the first and second positions for the distal and proximal portions, respectively.

18. The system of claim 17, wherein in the radially expanded condition the distal and proximal regions are expanded with first and second expanded outer diameters, respectively, which are sufficient to radially engage the aortic wall, and the intermediate region is expanded with a third expanded outer diameter that is less than the first and second expanded outer diameters and that is insufficient to radially engage the aortic wall along the proximal anastomosis site.

19. The system of claim 18, wherein the distal and proximal regions of the inflatable balloon are constructed to exhibit first and second radial compliances, respectively, when the balloon is being inflated; and the balloon along the intermediate region is constructed to exhibit a third radial compliance that is less than the first and second radial compliances when the balloon is being inflated.

20. The system of claim 19, wherein the balloon along the intermediate region comprises a different material than at least one of the distal and proximal regions of the balloon.

21. The system of claim 19, wherein the balloon comprises a balloon skin constructed at least in part of a material which extends along the intermediate region and at least one of the distal and proximal regions, wherein the balloon skin along the intermediate region has a first wall thickness and along the at least one of the distal and proximal regions has a second wall thickness which is less than the first wall thickness.

22. The system of claim 18, wherein an expansion limiter is provided along the intermediate region and which limits the expansion of the balloon along the intermediate region to the third expanded outer diameter in the radially expanded condition.

23. The system of claim 22, wherein the balloon along the intermediate region comprises a first material; and the expansion limiter comprises a second material which covers the first material.

24. The system of claim 22, wherein the balloon along the intermediate region comprises a first material; and the expansion limiter comprises a second material which forms a composite with the first material.

25. The system of claim 24, wherein the balloon along the intermediate region comprises a first material; and the expansion limiter comprises a second material which is embedded within the first material.

26. The system of claim 24, wherein the balloon along the intermediate region comprises a first material; and the expansion limiter comprises a second material which is laminated with the first material.

27. The system of claim 18, wherein the distal portion is constructed to exhibit a first compliance when the balloon is inflated; and the proximal portion is constructed to exhibit a second compliance when the balloon is inflated that is substantially different than the first compliance such that the distal and proximal regions expand to the first and second extended positions, respectively, at different inflation pressures, whereby controlling the inflation pressure of the balloon the distal and proximal portions may be controllably and sequentially engaged to the aortic wall.

28. The system of claim 1, wherein the intermediate port comprises a plurality of apertures through which the flow lumen communicates externally of the elongate body.

29. The system of claim 1, further comprising a visualization marker provided as a predetermined location relative to the intermediate region, such that the visualization marker and thereby the intermediate region may be located from a position externally of the aorta prior to forming the proximal anastomosis at the proximal anastomosis site.

30. The system of claim 29, wherein the visualization marker comprises a radiopaque material which is visible via X-ray fluoroscopy.

31. The system of claim 29, wherein the visualization marker is ultrasonically visible.

32. The system of claim 31, further comprising an ultrasound imaging system which is adapted to ultrasonically locate the visualization marker from a location externally of the aorta when the visualization marker is positioned within the aorta.

33. The system of claim 29, wherein the visualization marker comprises a light source which is adapted to emit light from within the aorta that which is detectable from a location externally of the aorta.

34. The system of claim 1, wherein the first and second extended positions, the distal and proximal portions are substantially radiopaque and visible using X-ray fluoroscopy, and the intermediate region is substantially non-radiopaque, such that the location of the intermediate region within the aorta may be identified under X-ray fluoroscopy in relation to the respectively spaced locations of the radiopaque distal and proximal portions.

35. The system of claim 1, further comprising:
a proximal anastomosis device assembly which is adapted to anastomose a proximal end of a bypass graft to an aperture formed in the aortic wall at the proximal anastomosis site.

36. The system of claim 1, further comprising:
a distal anastomosis device assembly which is adapted to anastomose a distal end of a bypass graft to an aperture formed in an arterial wall at a distal anastomosis site.

37. The system of claim 1, further comprising:
a support assembly which is adapted to engage a heart of the patient and to secure the heart such that at least one of a proximal anastomosis along the proximal anastomosis site and a distal anastomosis along a distal anastomosis site of a cardiac artery may be formed with an arterial by-pass graft while the heart is beating.

38. The system of claim 1, further comprising:
at least one actuator which is adapted to couple to and adjust at least one of the distal and proximal portions to the respectively extended position.

39. The system of claim 1, further comprising:
a venting member with a proximal end portion, a distal end portion, and a venting lumen which extends between a distal venting port along the distal end portion of the venting member and a proximal venting port along the proximal end portion of the venting member, wherein the distal end portion of the venting member is adapted to be positioned upstream from the proximal anastomosis site with the proximal end portion of the venting member positioned externally of the patient when the intermediate region is positioned along the proximal anastomosis site.

40. The system of claim 39, further comprising:
a decompression pump which is adapted to couple to the proximal venting port externally of the patient.

41. The system of claim 1, further comprising:
a cardioplegia member with a proximal end portion, a distal end portion, and a cardioplegia lumen which extends between a distal cardioplegia port along the distal end portion of the cardioplegia member and a proximal cardioplegia port along the proximal end portion of the cardioplegia member,
wherein the distal end portion of the cardioplegia member is adapted to be positioned upstream from the proximal anastomosis site with the proximal end portion of the cardioplegia member positioned externally of the patient when the isolation region is positioned along the proximal anastomosis site.

42. The system of claim 1, further comprising:
a cardiac bypass pump assembly which is adapted to couple to the proximal port and also to circulate oxygenated blood into the flow lumen through the proximal port, such that by adjusting said adjustable valve to the closed position the oxygenated blood may be delivered to the patient from the proximal port, along the flow lumen, and through the intermediate port.

43. A method for anastomosing an arterial bypass graft to a proximal anastomosis site along an aortic wall of an aorta in a patient, comprising:
endolumenally isolating a proximal anastomosis site along an aortic wall from a volume of pressurized blood in the aorta using an aorta isolation assembly provided along a distal end portion of an elongate body; said elongate body having a proximal end portion, a distal end portion, a longitudinal axis, and a flow lumen which extends between a distal port located along the distal end portion of the elongate body and a proximal port located along the proximal end portion of the elongate body, wherein the flow lumen communicates externally of the elongate body through an intermediate port located between the distal and proximal ports;
while the proximal anastomosis site is isolated from the volume of pressurized blood with the aorta isolation assembly, shunting the volume of blood through said flow lumen along the elongate body from such distal port of the flow lumen positioned along an upstream region of the aorta located upstream from the proximal anastomosis site and through a proximal port of the flow lumen positioned along a downstream region of the aorta located downstream from the proximal anastomosis site; and
while the volume of blood is being shunted from the upstream region to the downstream region, positioning a movable cannula having an adjustable valve within the flow lumen between the distal and proximal ports and expanding said adjustable valve within the flow lumen proximally of said intermediate port to a closed position.

44. The method of claim 43, further comprising while the proximal anastomosis site is being isolated from the volume of pressurized blood, and while the volume of pressurized blood is being shunted from the upstream region to the downstream region of the aorta, forming a proximal anastomosis between the arterial bypass graft and the proximal anastomosis site.

45. The method of claim 44, further comprising isolating the proximal anastomosis site in a "beating heart" coronary bypass graft procedure.

46. The method of claim 44, further comprising isolating the proximal anastomosis site in a "semi-beating heart" coronary artery bypass graft procedure.

47. An endolumenal aortic isolation system comprising:
an elongate body with a proximal end portion, a distal end portion, a longitudinal axis, and a flow lumen which extends between a distal port located along the distal end portion of the elongate body and a proximal port located along the proximal end portion of the elongate body, wherein the flow lumen communicates externally of the elongate body through and intermediate port located between the distal and proximal ports;

a cannula member, having a distal and proximal end and an axis of elongation, removeably and slidably carried relative to said elongate body so as to permit axial movement of said cannula member within said flow lumen, said cannula member comprising an adjustable valve member carried by said cannula adjacent said distal end where said adjustable valve member is selectively positionable in said flow lumen such that upon adjusting said adjustable valve member to a closed position after said adjustable valve member is positioned between said intermediate port and said proximate ports, said flow lumen is open between said distal and intermediate ports and closed between said intermediate and proximate ports, and when said adjustable valve member is adjusted to a closed position after positioning said adjustable valve member between said distal and intermediate ports said flow lumen is open between said proximate and intermediate ports and closed between said intermediate and distal ports;

an aorta isolation means located along the distal end portion of the elongate body having a distal portion located proximally of the distal port and a proximal portion located proximally of the distal portion and distally of the intermediate port for engaging an aortic wall of an aorta when extended circumferentially from a collapsed position such that upon engagement with said aortic wall an intermediate region between said distal portion and proximal portion is isolated from a volume of pressurized blood within said aorta upstream and downstream from said distal portion and said proximal portion respectively;

wherein said aorta isolation means is adapted to isolate a proximal anastomosis site along the aortic wall from said volume of pressurized blood at a location in the aorta either distally from the distal portion or proximally from the proximal portion of said aorta isolation means with respect to the elongate body by positioning said intermediate region within the aorta along a proximal anastomosis site and extending said distal and proximal portions to circumferentially engage said aortic wall on upstream and downstream sides of the proximal anastomosis site.

48. The system of claim 47, wherein the distal and proximal portions of the aorta isolation means are separately adjustable to first and second extended positions, respectively.

49. The system of claim 48, wherein the distal and proximal portions are adapted to couple to at least one expansion actuator and are radially expandable to the first and second extended positions, respectively.

50. The system of claim 49, wherein the distal and proximal portions are adapted to couple to first and second expansion actuators, respectively.

51. The system of claim 49, wherein the distal and proximal portions comprise distal and proximal balloons, respectively, that are adapted to fluidly couple to at least one pressurizeable fluid source and to inflate to the first and second extended positions, also respectively.

52. The system of claim 51, wherein the distal and proximal balloons are adapted to fluidly couple separately to first and second pressurizeable fluid sources, respectively.

53. The system of claim 51, wherein the elongate body further comprises a distal inflation lumen fluidly coupled to the distal balloon and a proximal inflation lumen fluidly coupled to the proximal balloon, the distal and proximal inflation lumens being adapted to fluidly couple to said at least one pressurizeable fluid source.

54. The system of claim 51, wherein the distal and proximal inflation lumens are a adapted to separately couple to first and second pressurizeable fluid sources, respectively.

55. The system of claim 49, wherein the distal and proximal portions are adapted to couple to a common expansion actuator which is adjustable between first and second actuating conditions, the distal portion being expandable to the first extended position when the common actuator is adjustable to the first actuating condition, and the proximal portion being adjustable to the second extended position when the common actuator is adjusted to the second actuating condition.

56. The system of claim 55, wherein the distal and proximal portions comprise distal proximal balloons, respectively, which are each adapted to fluidly couple to a common pressurizeable fluid source and are inflatable with fluid from the fluid source to the first and second extended positions, respectively, wherein the distal balloon is inflatable to the first extended position when the fluid is adjusted to a first pressure, and wherein the proximal balloon is inflatable to the second extended position when the fluid is adjusted to a second pressure.

57. The system of claim 56, wherein the distal balloon comprises a first material with a first compliance and the proximal balloon comprises a second material with a second compliance which is different from the first compliance.

58. The system of claim 56, the elongate body further comprises a common lumen which is fluidly coupled to the distal and proximal balloons and which is also adapted to couple to the common pressurizeable source of fluid.

* * * * *